United States Patent
Johnson et al.

(10) Patent No.: US 10,344,005 B2
(45) Date of Patent: Jul. 9, 2019

(54) SYNTHESIS OF CYCLOPHANES FOR A SELF-ASSEMBLY REACTION

(71) Applicant: University of Oregon, Eugene, OR (US)

(72) Inventors: Darren W. Johnson, Eugene, OR (US); Mary Collins, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 15/698,284

(22) Filed: Sep. 7, 2017

(65) Prior Publication Data

US 2017/0369456 A1    Dec. 28, 2017

Related U.S. Application Data

(62) Division of application No. 14/944,584, filed on Nov. 18, 2015, now Pat. No. 9,790,192.

(60) Provisional application No. 62/081,398, filed on Nov. 18, 2017.

(51) Int. Cl.
| | |
|---|---|
| *C07C 321/16* | (2006.01) |
| *C07D 251/24* | (2006.01) |
| *C07D 341/00* | (2006.01) |
| *C07D 495/22* | (2006.01) |

(52) U.S. Cl.
CPC .......... *C07D 251/24* (2013.01); *C07C 321/16* (2013.01); *C07D 341/00* (2013.01); *C07D 495/22* (2013.01)

(58) Field of Classification Search
CPC ............................ C07D 251/24; C07C 321/16
USPC .................................. 544/180, 215; 568/25
See application file for complete search history.

(56) References Cited

U.S. PATENT DOCUMENTS 9,790,192 B2 * 10/2017 Johnson ............... C07D 341/00

OTHER PUBLICATIONS

Brisig et al., "Selection and amplification of a catalyst from a dynamic combinatorial library," *Angewandte Chemie*, vol. 42, No. 11, pp. 1270-1273, 2003. Published Mar. 13, 2003.

Chan et al., "A new one-flask Ramberg-Backlund reaction," *J. Chem. Soc., Chem. Commun.*, pp. 1771-1772, 1994. Published Jan. 1, 1994.
Collins et al., "Pnictogen-directed synthesis of discrete disulfide macrocycles," *Chem. Commun.*, vol. 49, pp. 6588-6601, 2013. Published Jun. 5, 2013.
Gross et al., "Concave Hydrocarbons," *Chem. Eur. J.*, vol. 2, No. 12, pp. 1585-1595, Dec. 1996.
Houk et al., "Structure-reactivity relations for thiol-disulfide interchange," *J. Am. Chem. Soc.*, vol. 109, pp. 6825-6836, 1987. Oct. 1, 1987.
Mitchell et al., "Syntheses and reactions of the first dithia [3.1.3.1] metacyclophanes, [2.1.2.1] metacyclophanes, and [2.1.2.1] metacyclophanedienes," *J. Org. Chem.*, vol. 49, pp. 2534-2540, 1984. Published Jul. 1, 1984.
Montanari, et al., "Mild preparation of functionalized [2.2] paracyclophanes via the Pummerer rearrangement," *Organic & Biomolecular Chemistry*, vol. 9, pp. 5018-5020, 2011. Published Mar. 31, 2011.
Otsubo et al., An alternate route for the conversion of dithia [3.3] cyclophanes to cyclophane-dienes. Reaction with benzyne followed by sulfoxide pyrolysis, *Pergamon Press*, Tetrahedron Letters No. 45, pp. 3881-3884, Sep. 29, 1975.
Otto et al., "Selection and amplification of hosts from dynamic combinatorial libraries of macrocyclic disulfides," *Science*, vol. 297, pp. 590-593, Jul. 26, 2002.
Singh et al., "Comparisons of rate constants for thiolate-disulfide interchange in water and in polar aprotic solvents using dynamic H NMR line shape analysis," *J. Am. Chem. Soc.*, vol. 112, pp. 1190-1197, 1990. Published Jan. 1, 1990.
West et al., "Dynamic combination discovery of a [2]-catenane and its guest-induced conversion into a molecular square host," *JACS Communications*, Feb. 28, 2008.
Yu et al., "Synthesis and ring-opening metathesis of tetraalkoxy-substituted [2.2] paracyclophane-1,9-dienes," *Chem. Eur. J.*, vol. 17, pp. 6991-6997, 2011. Published Jun. 14, 2011.

* cited by examiner

*Primary Examiner* — Venkataraman Balasubramanian
(74) *Attorney, Agent, or Firm* — Klarquist Sparkman, LLP

(57) ABSTRACT

Disclosed herein is a novel method for preparing cyclophanes, comprising forming a disulfide cyclophane by contacting a linker moiety which includes two or more thiol groups, with a metal salt and an oxidant. The disulfide cyclophane is then desulfurized to form a thiacyclophane comprising thioether bridges. This thiacyclophane optionally may be further desulfurized to form an unsaturated hydrocarbon cyclophane, which can then be reduced to form a saturated hydrocarbon cyclophane. The various cyclophanes can be synthesized in a ring form, such as a dimer, trimer or tetramer etc., or they can be synthesized in a tetrahedral or larger structure. Also disclosed are novel cyclophanes formed by the disclosed method.

18 Claims, 8 Drawing Sheets

SYNTHESIS OF CYCLOPHANES FOR A SELF-ASSEMBLY REACTION

CROSS REFERENCE TO RELATED APPLICATIONS

This application is a divisional of U.S. patent application Ser. No. 14/944,584 filed on Nov. 18, 2015, which claims the benefit of the earlier filing date of U.S. Provisional Application No. 62/081,398, filed on Nov. 18, 2014. Both applications are incorporated herein by reference in their entirety.

BACKGROUND

Since the first synthesis of metacyclophane by Pellegrin in 1899 and paracyclophane by Cram et al. in 1951, there has been wide interest in these highly strained systems. The restricted positions of the often distorted aromatic rings in these classes of molecules have allowed many studies of the fundamental properties of aromaticity itself. The well-defined topology and high strain of cyclophanes has also found utility in a number of applications including asymmetric catalysis, insulating plastics, and organic electronics. Unfortunately, the field of cyclophane chemistry has been hindered by a lack of high yielding and functional group tolerant preparative methods for their synthesis.

Previous methods to synthesize cyclophanes have relied on intra-and intermolecular macrocyclizations at high dilution and non-ambient temperatures. In many cases, indiscriminant homocouplings such as Wurtz or McMurry couplings are used where a mixture of oligomers and polymer is the primary product. In some more selective cases, Wittig reactions are used to make mixed macrocycles but these cases still rely on unfavorable ring formation. Despite the significant breadth of applications cyclophanes serve in, their synthesis is still confined to synthetic methods devised more than 40 years ago. These regimens, although generally successful, provide little if any selectivity, low yields, and require difficult purifications.

SUMMARY

Disclosed herein are embodiments of methods providing a route to synthesize cyclophanes in a more efficient and selective way with high, reproducible yields, which is a substantial advancement to conventional cyclophane syntheses. In some embodiments, the method comprises forming a disulfide cyclophane by contacting a linker with a metal salt and an oxidant, the linker comprising an aromatic ring and a plurality of thiol groups, and forming a thiacyclophane by desulfurization of the disulfide cyclophane. In some embodiments, the linker has a formula

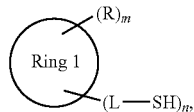

where ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; n is from 2 to 6 and each L independently is a bond, aliphatic, aralkyl, aryl, heteroaryl or heteroaralkyl.

In some embodiments, n is 2, in other embodiments, n is 3 and in further embodiments, n is 6. In some examples, ring 1 is phenyl. In certain embodiments, L is a bond or lower alkyl, and may be CH2. In some embodiments, at least one L is aralkyl. And in some examples, R is alkoxy, and may be methoxy.

In some embodiments, the linker has a formula selected from

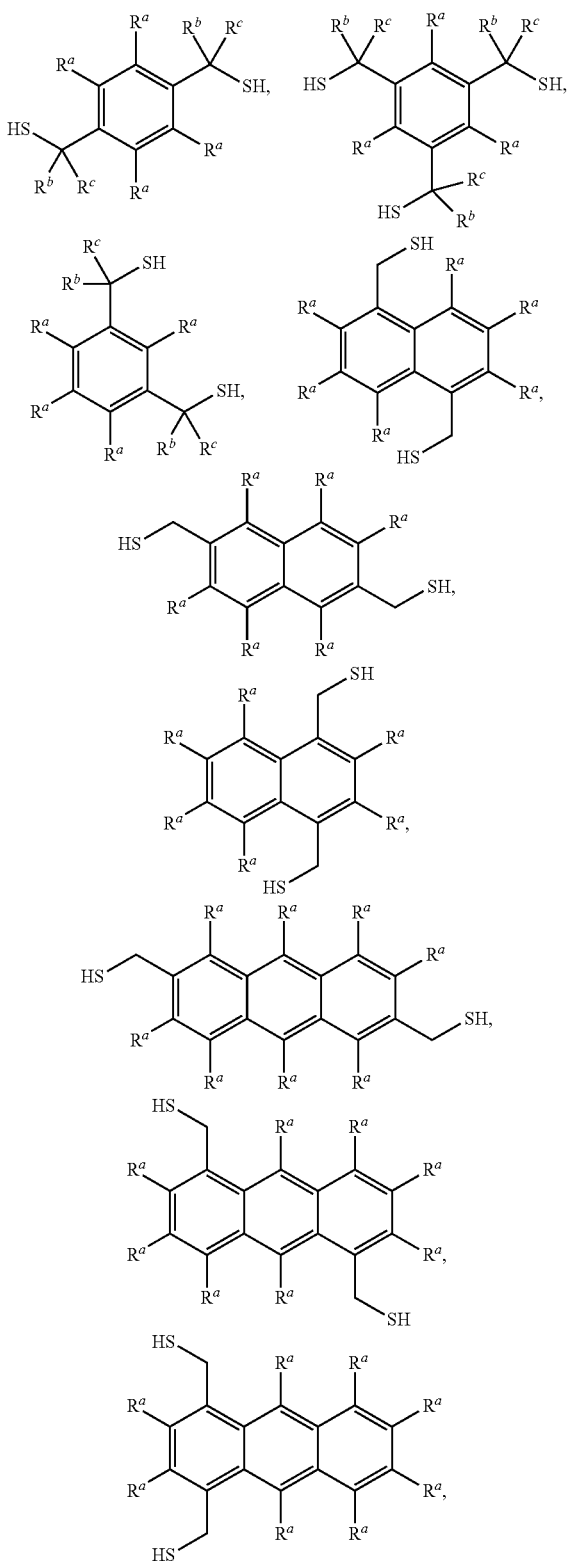

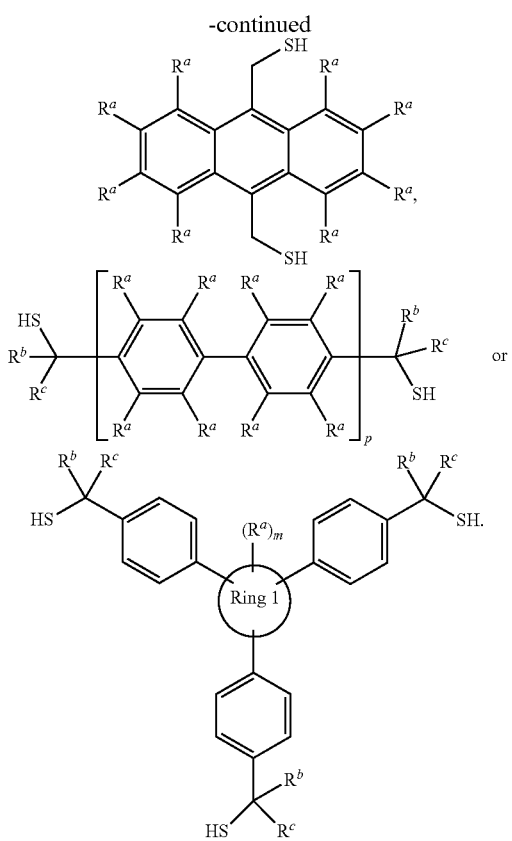

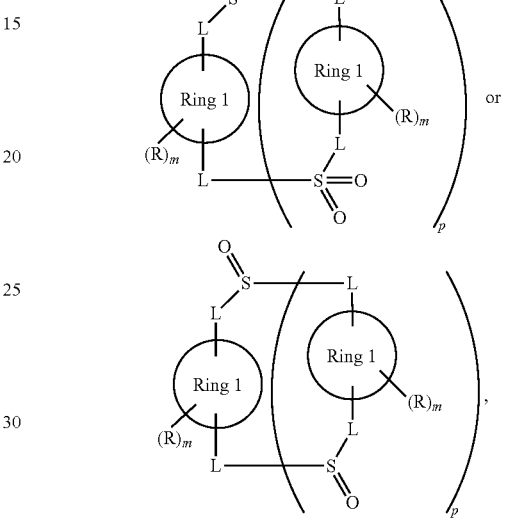

With respect to these formulas, each $R^a$ independently is hydrogen, carboxyl ester, aminocarbonyl, aliphatic, heteroaliphatic, $NO_2$, sulfonyl, amine, protected amine, aryl, heteroaryl, OH or halogen; each $R^b$ independently is hydrogen, aliphatic or heteroaliphatic; each $R^c$ independently is hydrogen, aliphatic or heteroaliphatic; ring 1 is aryl or heteroaryl; m is from 0 to 3; and p is from 1 to 4.

In some embodiments, $R^c$ is hydrogen, and in other embodiments, each $R^a$ independently is selected from hydrogen or alkoxy.

The metal salt may be a metal dihalide, metal trihalide, metal tetrahalide, metal triflate or a combination thereof, and may comprise a pnictogen, transition metal or a combination thereof. In some examples, the metal salt comprises antimony, arsenic, bismuth or zinc, and in particular examples, the metal salt is $SbCl_3$ or $AsCl_3$.

In some embodiments, the oxidant comprises iodine, oxygen, bicarbonate salt, 2,3-dichloro-5,6-dicyano-1,4-benzoquinone (DDQ) or a combination thereof.

In some examples, contacting the linker with a metal salt and an oxidant comprises contacting the linker with less than a stoichiometric amount of the metal salt and/or the oxidant.

The desulfurization of the disulfide cyclophane may comprise contacting the disulfide cyclophane with a phosphoramide, and in some embodiments, the phosphoramide is hexamethylphosphoramide, hexaethylphosphoramide or a combination thereof. In some examples, the desulfurization of the disulfide cyclophane comprises using glassware washed with aqua regia and then oven and/or flame dried. The desulfurization of the disulfide cyclophane may proceed without agitation, without heat above ambient temperature, or a combination thereof.

In some embodiments, the method further comprises forming an unsaturated hydrocarbon cyclophane by desulfurization of the thiacyclophane, and may further comprise forming a saturated hydrocarbon cyclophane by reducing the unsaturated hydrocarbon cyclophane. In some embodiments, the desulfurization of the thiacyclophane comprises contacting the thiacyclophane with dimethoxycarbonium tetrafluoroborate. In other embodiments, the desulfurization of the thiacyclophane comprises contacting the thiacyclophane with an oxidizing agent to form an oxidized intermediate, followed by pyrolysis of the oxidized intermediate or a base-induced elimination such as a Ramberg-Backlund elimination. In some examples, the oxidized intermediate has a formula where ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; p is from 1 to 10; and each L independently is a bond, aliphatic, aralkyl, aryl, heteroaryl or heteroaralkyl.

In some examples, the disulfide cyclophane has a formula selected from

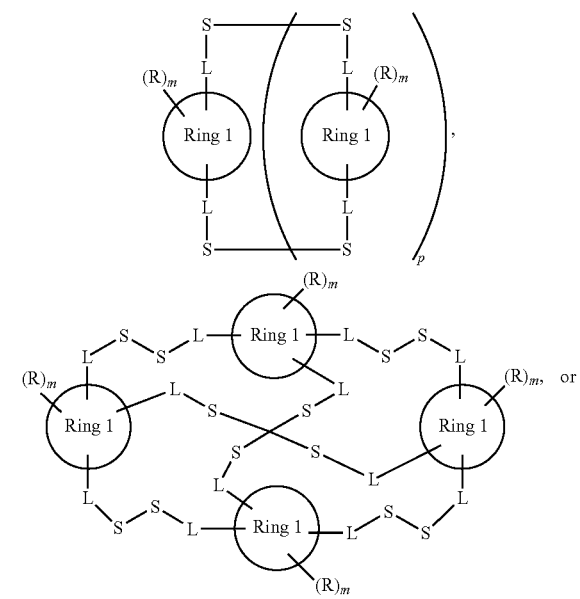

-continued

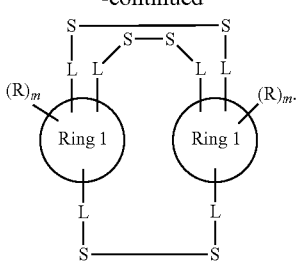

In some embodiments, the thiacyclophane has a formula selected from

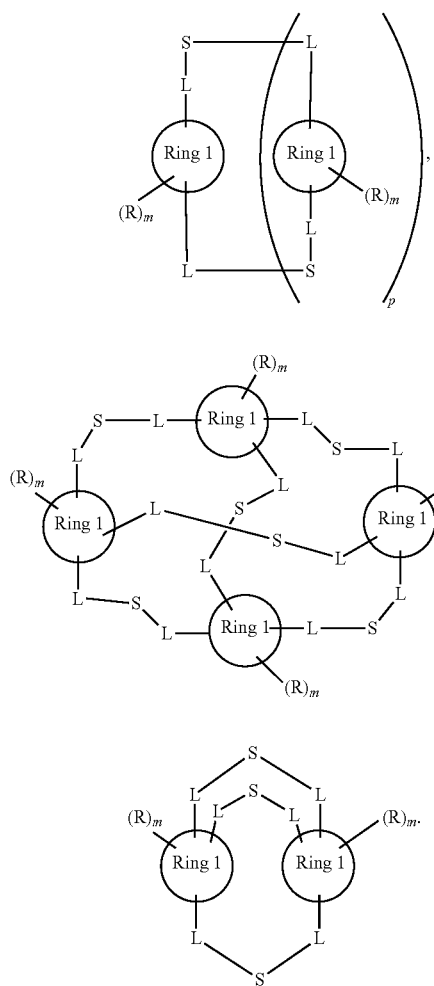

In some embodiments, the unsaturated cyclophane has a formula selected from

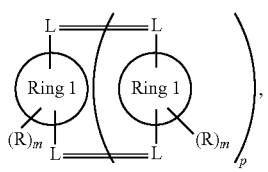

-continued

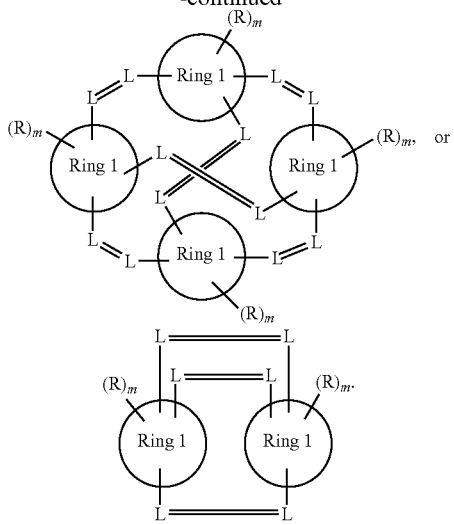

In some embodiments, the saturated cyclophane has a formula selected from

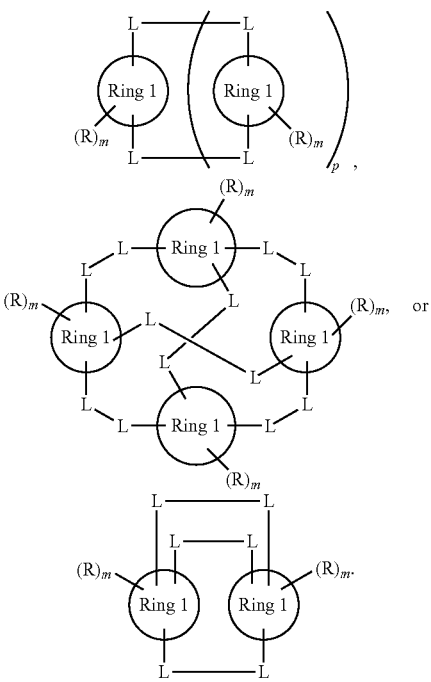

With respect to the formulas above for the disulfide cyclophane, the thiacyclophane, the unsaturated cyclophane and the saturated cyclophane, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; p is from 1 to 10; and each L independently is a bond, aliphatic, aralkyl, aryl, heteroaryl or heteroaralkyl. In certain examples, p is from 1 to 6.

In some embodiments, the method further comprises forming a polymer by contacting the unsaturated cyclophane with a ring-opening reagent or catalyst. In some embodiments, the ring-opening reagent or catalyst is [1,3-bis-(2,4,6-trimethylphenyl)-2-imidazolidinylidene]dichloro(phenylmethylene) (tricyclohexylphosphine)ruthenium, and in some examples, the polymer has a formula

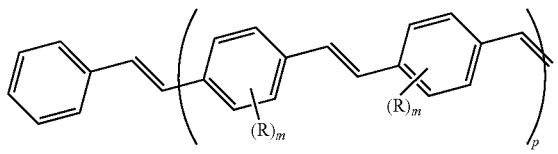

wherein p is from 1 to 10; each R independently is carboxyl ester, aminocarbonyl, aliphatic, heteroaliphatic, $NO_2$, sulfonyl, amine, protected amine, aryl, heteroaryl, OH, oxo or halogen; and m is from 0 to 4.

Also disclosed herein are embodiments of a compound having a formula

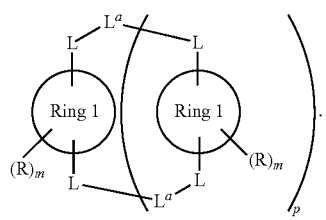

With respect to this formula, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m independently is from 0 to 4; p is from 1 to 10; each L independently is aliphatic, aralkyl, aryl, heteroaryl or heteroaralkyl; and $L^a$ is single bond, double bond, —S—, —S(O)—, —S(O)$_2$—, or —S—S—. Also with respect to this formula, if ring 1 is phenyl, m is 0, p is 1, 2 or 3 and each L is $CH_2$, then $L^a$ is not —S—; if ring 1 is phenyl, m is 0, $L^a$ is —S—S— and each L is $CH_2$, then p is not 1, 2 or 3; if ring 1 is phenyl, m is 0, and each L is $CH_2$, then $L^a$ is not a single bond or a double bond; and if ring 1 is 1,5-naphthyl, m is 0, p is 1 and each L is $CH_2$, then $L^a$ is not —S—S—.

In some examples, m is greater than 0, and/or p is greater than 3. In some embodiments, each R independently is heteroaliphatic, and may be methoxy. Each L independently may be aliphatic or aralkyl, and in some embodiments, at least one L is $CH_2$ or benzyl.

Also disclosed herein are embodiments of a compound having a formula

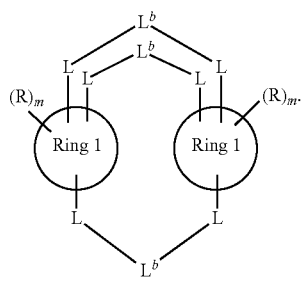

With respect to this formula, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; each L independently is a bond, aliphatic, aralkyl, aryl, heteroaryl or heteroaralkyl; and $L^b$ is —S—, —S(O)—, —S(O)$_2$—, —S—S—, double bond or single bond, provided that if ring 1 is phenyl, m is 0 and each L is $CH_2$, then $L^b$ is not —S—, single bond or double bond. In certain embodiments, ring 1 is phenyl, and in other embodiments, ring 1 is triazine. In some examples, each L is $CH_2$ and in other examples, each L is benzyl.

Also disclosed herein are embodiments of a compound having a formula

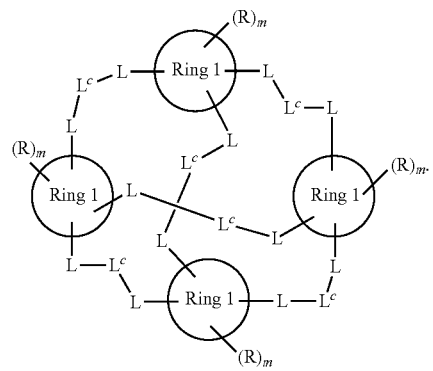

With respect to this formula, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; each L independently is a bond, aliphatic, aralkyl, aryl, heteroaryl or heteroaralkyl; and $L^c$ is —S—, —S(O)—, —S(O)2—, —S—S—, double bond or single bond. Also with respect to this formula, if ring 1 is phenyl, each L is $CH_2$, and m is 0 then $L^c$ is not a single bond, and if ring 1 is phenyl, one L is benzyl and the other two L moieties are $CH_2$, and m is 0, then $L^c$ is not a single bond.

In some embodiments, ring 1 is phenyl. In other embodiments, ring 1 is a heteroaryl, and ring 1 may be a triazine. In some examples, L is $CH_2$ and in certain other examples, each L is benzyl.

The foregoing will become more apparent from the following detailed description, which proceeds with reference to the accompanying figures.

DETAILED DESCRIPTION

I. Definitions

Figure 1:
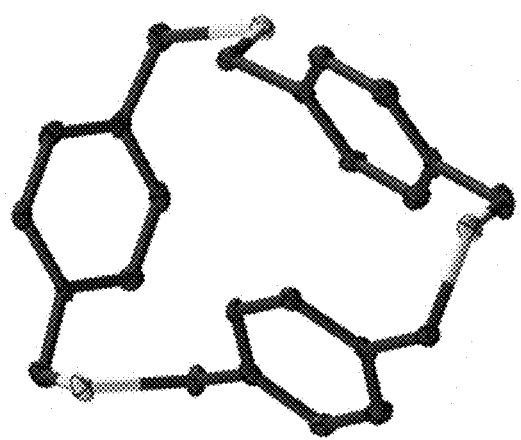
FIG. 1 is a single crystal X-ray structure representation of an exemplary disulfide macrocyclic trimer.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

The abbreviations used herein have their conventional meaning within the chemical and biological arts. The chemical structures and formulae set forth herein are constructed according to the standard rules of chemical valence known in the chemical arts.

The symbol "⌇⌇" denotes the point of attachment of a chemical moiety to the remainder of a molecule or chemical formula.

"Aliphatic" refers to a substantially hydrocarbon-based group, or a radical thereof (e.g., $C_6H_{13}$, for a hexane group), including cyclic versions thereof, such as alkyl, alkenyl, alkynyl, cycloalkyl, cycloalkenyl, and cycloalkynyl, and further including straight- and branched-chain arrangements, and all stereo and position isomers as well. Unless expressly stated otherwise, an aliphatic group contains from one to at least twenty-five carbon atoms ($C_1$-$C_{25}$); for example, from one to fifteen ($C_1$-$C_{15}$), from one to ten ($C_1$-$C_{10}$), from one to six ($C_1$-$C_6$), or from one to four ($C_1$-$C_4$) carbon atoms. A cycloaliphatic group, such as cycloalkyl and cycloalkenyl, contains at least three carbon atoms, such as from three to at least 25 carbon atoms. The term "lower aliphatic" refers to an aliphatic group comprising from one to ten carbon atoms. Unless expressly referred to as an "unsubstituted aliphatic," an aliphatic group can either be unsubstituted or substituted.

"Alkyl" refers to a straight (i.e., unbranched), branched or cyclic saturated hydrocarbon chain. Unless expressly stated otherwise, an alkyl group contains from one to at least twenty-five carbon atoms ($C_1$-$C_{25}$); for example, from one to fifteen ($C_1$-$C_{15}$), from one to ten ($C_1$-$C_{10}$), from one to six ($C_1$-$C_6$), or from one to four ($C_1$-$C_4$) carbon atoms. A cycloalkyl contains from three to at least twenty-five carbon atoms ($C_1$-$C_{25}$); for example, from three to fifteen ($C_1$-$C_{15}$), from three to ten ($C_1$-$C_{10}$), from three to six ($C_1$-$C_6$). The term "lower alkyl" refers to an alkyl group comprising from one to ten carbon atoms or three to ten for a cycloalkyl. Unless expressly referred to as "unsubstituted alkyl," an alkyl group can either be substituted or unsubstituted. Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. Examples of cycloalkyl groups include, but are not limited to, cyclopropyl, cyclobutyl, cyclopentyl, cyclohexyl and the like.

"Alkoxy" refers to the group —O-alkyl.

"Amino" refers to the group —NR'R", wherein R' and R" independently are selected from hydrogen, aliphatic, or heteroaliphatic, or where R' and R" are optionally joined together with the nitrogen bound thereto to form a cycloamino group such as a heterocyclic, heteroaryl group comprising at least one ring nitrogen. Exemplary cycloamino groups include, but are not limited to, pyrrolidine, pyrrole, imidazole, triazole, tetrazole, piperidine, triazinane, piperazine, morpholine, azepane, diazepane, azocane, diazocane, azonane or azecane. In some embodiments, R' and/or R" may be an amine protecting group, as understood by a person of ordinary skill in the art, thereby forming a "protected amino" group. Exemplary amine protecting groups include, but are not limited to, tert-butyloxycarbonyl (Boc), benzyl, benzoyl, or benzoyloxycarbonyl (Cbz). Additional information concerning protecting groups is provided by Greene and Wuts, *Protective Groups in Organic Synthesis;* 3rd Ed.; John Wiley & Sons, New York, 1999, which is incorporated herein by reference.

"Aminoalkyl" refers to a chemical functional group -alkyl-amino, where alkyl and amino are as defined herein.

"Aminocarbonyl" refers to a chemical functional group —C(=O)-amino, where amino is as defined herein. A primary aminocarbonyl is —CONH$_2$.

"Cyano" refers to the chemical functional group —CN.

"Cyclophane" is a molecule that comprises an aromatic unit and an aliphatic or heteroaliphatic chain or bridge connecting two non-adjacent positions of the aromatic ring. In some embodiments, a cyclophane molecule comprises a plurality of aromatic units and bridges between the aromatic units, and may form a cage-like structure. In some embodiments, the units are in sequence and form a ring-like structure. In other embodiments, the units form a cage molecule such as a tetrahedron-like structure or larger cage molecule such as a structure comprising 12 or 24 linker units. As used herein, a "disulfide cyclophane" is a cyclophane that comprises bridges between the aromatic units that include a disulfide bond (—S—S—); a "thiacyclophane" is a cyclophane that comprises a thioether in the bridges (—S—); an "unsaturated hydrocarbon cyclophane" or "unsaturated cyclophane" comprises hydrocarbon bridges that include at least one double bond; and a "saturated hydrocarbon cyclophane" or "saturated cyclophane" comprises saturated hydrocarbon bridges.

"Carboxyl," "carboxylic acid" or "carboxy" refers to the chemical functional group —CO$_2$H.

"Carboxyl ester," "carboxylic acid ester," or "carboxy ester" refers to the chemical functional group —CO$_2$R where R is aliphatic, heteroaliphatic, aryl or heteroaryl.

"Acyl" refers to —C(O)R where R is aliphatic, heteroaliphatic, aryl or heteroaryl.

"Aryl" or "Ar" refers to a monovalent aromatic carbocyclic group of from 6 to 15 carbon atoms having a single ring (e.g., phenyl) or multiple condensed rings (e.g., naphthyl or anthryl) in which at least one of the condensed rings is aromatic (e.g., 2-benzoxazolinone, 9,10-dihydrophenanthrene, and the like), provided that the point of attachment is through an atom of the aromatic aryl group. Unless otherwise specified, the aryl group may be optionally substituted. Preferred aryl groups include phenyl and naphthyl.

"Aryloxy" refers to the group —O-aryl.

"Arylthio" refers to the group —S-aryl.

"Aralkyl" refers to the group -alkyl-aryl. Exemplary aralkyl groups include benzyl and phenethyl.

"Heteroaliphatic" refers to an aliphatic compound or group, having at least one heteroatom, i.e., one or more carbon atoms has been replaced with an atom having at least one lone pair of electrons, typically nitrogen, oxygen, phosphorus, silicon, or sulfur. Typically, a heteroaliphatic group contains from two to at least twenty-five carbon or heteroatoms (referred to as a $C_2$-$C_{25}$ heteroaliphatic although at least one of the carbon atoms has been replaced by a heteroatom); for example, from two to fifteen ($C_2$-$C_{15}$), from two to ten ($C_2$-$C_{10}$), from two to six ($C_2$-$C_6$), or from two to four carbon or heteroatoms ($C_2$-$C_4$). Heteroaliphatic compounds or groups may be substituted or unsubstituted, branched or unbranched, cyclic or acyclic, and include "alkoxy", "alkylthio", "heterocycle", "heterocyclyl", "heterocycloaliphatic", or "heterocyclic" groups. A heterocyclic group contains at least three atoms, such as from three to at least twenty five, referred to as $C_3$-$C_{25}$ (although at least one of the carbon atoms has been replaced by a heteroatom). Examples of heteroaliphatic groups include methoxy, ethoxy, propoxy, butoxy, PEG, such as PEG2, PEG, 3, PEG 4, PEG 5, PEG 6, PEG 7, PEG 8, PEG 9 or PEG 10, methoxymethyl or methylthiomethyl. Examples of heterocycles include morpholino, tetrahydrofuranyl and piperidinyl.

"Halo", "halide" or "halogen" refers to fluoro, chloro, bromo, and iodo.

"Heteroaryl" refers to an aromatic group having from 1 to 15 carbon atoms and at least one, and more typically 1 to 4, heteroatoms selected from oxygen, nitrogen or sulfur within the ring. Unless otherwise specified, the heteroaryl group may be optionally substituted. Such heteroaryl groups can have a single ring (e.g., pyridinyl, imidazolyl or furyl) or multiple condensed rings (e.g., indolizinyl, quinolinyl, benzimidazolyl, benzopyrazolyl or benzothienyl), wherein at least one of the condensed rings is aromatic and may or may not contain a heteroatom, provided that the point of attachment is through an atom of an aromatic ring. In one embodiment, the nitrogen and/or sulfur ring atom(s) of the heteroaryl group are optionally oxidized to provide N-oxide (N→O), sulfinyl, or sulfonyl moieties. Preferred heteroaryls include pyridinyl, pyrrolyl, indolyl, thiophenyl, benzopyrazolyl and furanyl.

"Heteroaryloxy" refers to the group —O-heteroaryl.

"Heteroarylthio" refers to the group —S-heteroaryl.

"Heteroaralkyl" refers to the group -alkyl-heteroaryl. Exemplary heteroaralkyl groups include picolyl and furfuryl.

"Hydroxy" and "hydroxyl" refer to the group —OH.

"Mercapto" and "thiol" refer to the group —SH.

"Oxo," refers to an oxygen that is double bonded to a carbon atom.

"Sulfonamide" refers to the group —SO$_2$-amino, where amino is as defined herein. A primary sulfonamide is —SO$_2$NH$_2$.

"Sulfonyl" refers to the group —SO$_2$—R, where R is aliphatic, heteroaliphatic, aryl or heteroaryl. Sulfonyl includes groups such as —SO$_2$-methyl, —SO$_2$-phenyl, —SO$_2$-thiophene, —SO$_2$-cyclohexyl, —SO$_2$-benzyne and —SO$_2$-(4-methylphenyl).

As used herein, a group can be substituted with one or more substituents (up to two substituents for each methylene [—CH$_2$—] carbon, such as in an saturated aliphatic or heteroaliphatic chain or ring, or up to one substituent for each carbon of a —C═C— double bond such as in an aryl group, heteroaryl group or an unsaturated aliphatic or heteroaliphatic chain or ring, or up to one substituent for a carbon of a terminal methine group). Exemplary substituents include, but are not limited to, aliphatic, heteroaliphatic, amino, aminocarbonyl, sulfonamide, halo, cyano, carboxy, hydroxyl, mercapto, trifluoromethyl, alkyl, alkoxy, alkylthio, arylalkyl, heteroaryl, alkylamino, dialkylamino, aryl, aryloxy, heteroaryloxy, heterocyclic, arylthio, heteroarylthio, oxo, NO$_2$, sulfonyl or other functionality. In a preferred embodiment, a group that is substituted has 1 substituent, 1 or 2 substituents, 1, 2, or 3 substituents or 1, 2, 3 or 4 substituents.

Also, it is understood that the above definitions are not intended to include impermissible substitution patterns. Such impermissible substitution patterns are understood by a person having ordinary skill in the art.

Additionally, it is understood by a person of ordinary skill in the art that if an atom does not appear to have sufficient specific bonds to satisfy valence requirements, such as an apparent trivalent carbon, there are sufficient implicit hydrogens present to satisfy those valence requirements.

"Desulfurization" means to remove one or more sulfur atoms from a molecule, via a chemical reaction or process. For example, desulfurization of a disulfide bond (CH$_2$—S—S—CH$_2$) to form a thioether (CH$_2$—S—CH$_2$), or desulfurization of a thioether to form a hydrocarbon.

II. Compounds

Disclosed herein are embodiments of a compound having a formula I

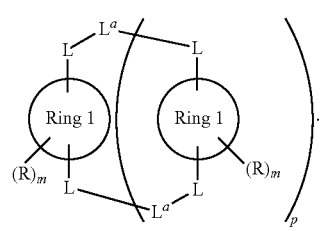

I

With respect to formula I, ring 1 is aryl or heteroaryl, each R independently is carboxyl ester, aminocarbonyl, aliphatic, heteroaliphatic, NO$_2$, sulfonyl, amine, protected amine, aryl, heteroaryl, OH, oxo or halogen, m independently is from 0 to 4, p is from 1 to 10, each L independently is aliphatic, aralkyl, aryl, heteroaryl or heteroaralkyl, and $L^a$ is single bond, double bond, —S—, —S(O)—, —S(O)$_2$— or —S—S—.

Also with respect to formula I, the following provisos may apply:

if ring 1 is phenyl, m is 0, p is 1, 2 or 3 and each L is CH$_2$, then L$^a$ is not —S—;

if ring 1 is phenyl, m is 0, L$^a$ is —S—S— and each L is CH$_2$, then p is not 1, 2 or 3;

if ring 1 is phenyl, m is 0, and each L is CH$_2$, then L$^a$ is not a single bond or a double bond;

if ring 1 is 1,3-disubstituted phenyl, m is 0, L$^a$ is —S—S—, and each L is CH$_2$, then p is not 1 if ring 1 is 1,5-naphthyl, m is 0, p is 1 and each L is CH$_2$, then L$^a$ is not —S—S—.

In some embodiments where L$^a$ is —S—S—, if ring 1 is a 1,4-disubstituted phenyl, m is 0 and each L is CH$_2$, then p is not 1, 2 or 3; and if ring 1 is 1,5-naphthyl, m is 0 and each L is CH$_2$, then p is not 1.

In some embodiments, ring 1 is aryl, and in certain embodiments, ring 1 is phenyl, naphthyl or anthracenyl. In other embodiments, ring 1 is heteroaryl.

In some embodiments, at least one L is aliphatic, and in certain embodiments, at least one L is alkyl. In particular embodiments, at least one L is CH$_2$. In some examples, at least one L is aralkyl, and in certain examples, at least one L is benzyl, or [1,1'-biphenyl]-4-ylmethyl.

In some embodiments, m is greater than 0, such as 1, 2, 3 or 4. In other embodiments, p is 1, 2 or 3. In other examples, p is greater than 3, such as 4, 5, 6, 7, 8, 9 or 10.

In certain embodiments, each R is heteroaliphatic, including, but not limited to alkoxy, such as methoxy or ethoxy, or PEG, such as a PEG 2, PEG 3, PEG 4 PEG, 5 PEG 6 PEG, 8 or PEG 10. In particular embodiments, each R is methoxy.

In some embodiments, ring 1 is a six-membered ring, and the two L moieties are para to each other. In alternative embodiments, the two L moieties are meta to each other.

In some embodiments, the

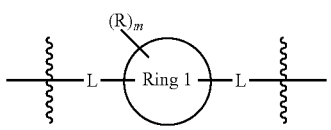

moiety is selected from

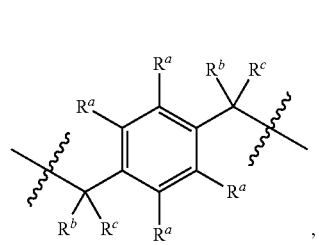

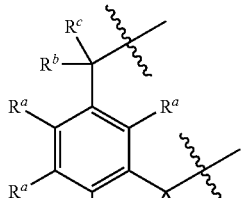

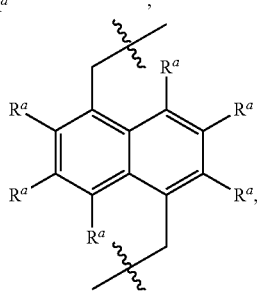

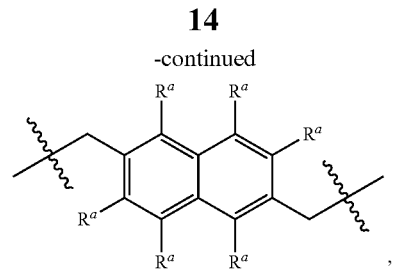

-continued

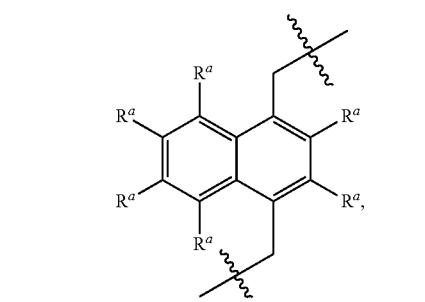

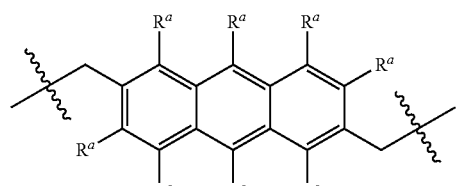

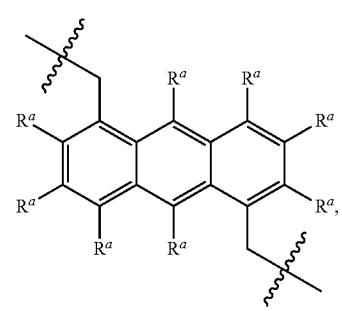

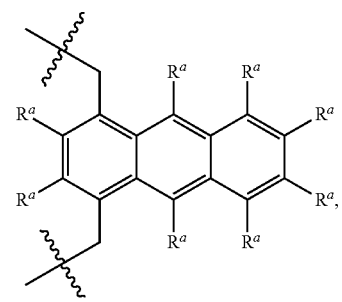

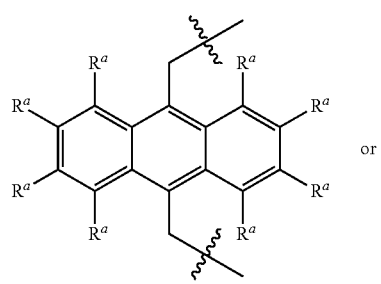

or

-continued

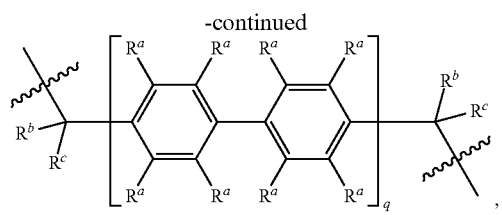

where each $R^a$ independently is hydrogen, carboxyl ester, aminocarbonyl, aliphatic, heteroaliphatic, $NO_2$, sulfonyl, amine, protected amine, aryl, heteroaryl, OH or halogen; each $R^b$ independently is hydrogen, aliphatic or heteroaliphatic; each $R^c$ independently is hydrogen, aliphatic or heteroaliphatic; and q is from 1 to 4. In some embodiments, $R^c$ is hydrogen, and in others $R^c$ is alkyl. In some examples, each $R^a$ independently is hydrogen or alkoxy.

In some embodiments, the compounds have a formula selected from

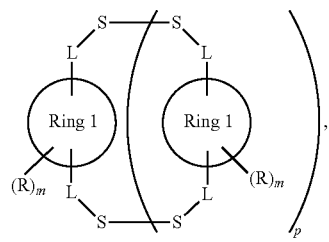

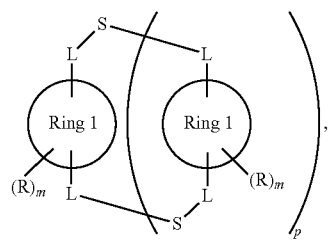

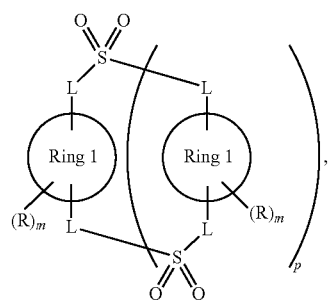

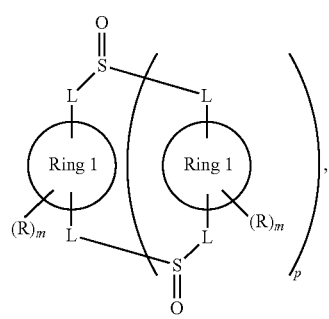

-continued

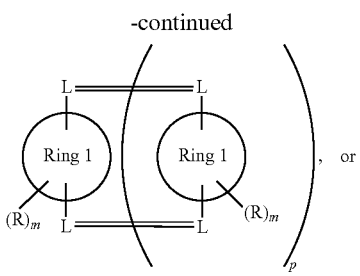, or

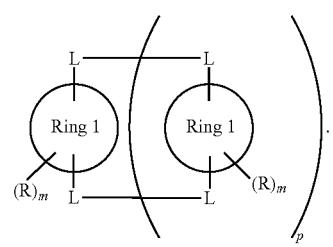.

In some embodiments, ring 1 is phenyl, leading to compounds having a formula Ia

Ia

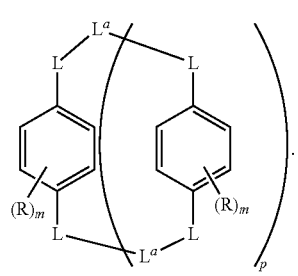.

In certain embodiments of formula Ia, compounds have a formula selected from

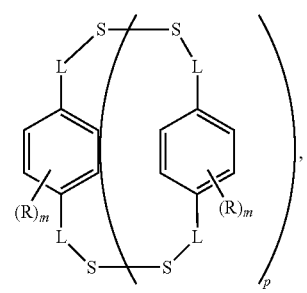,

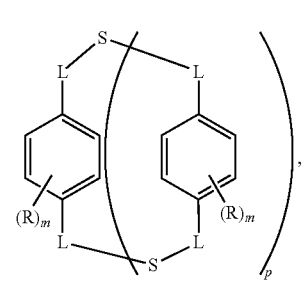,

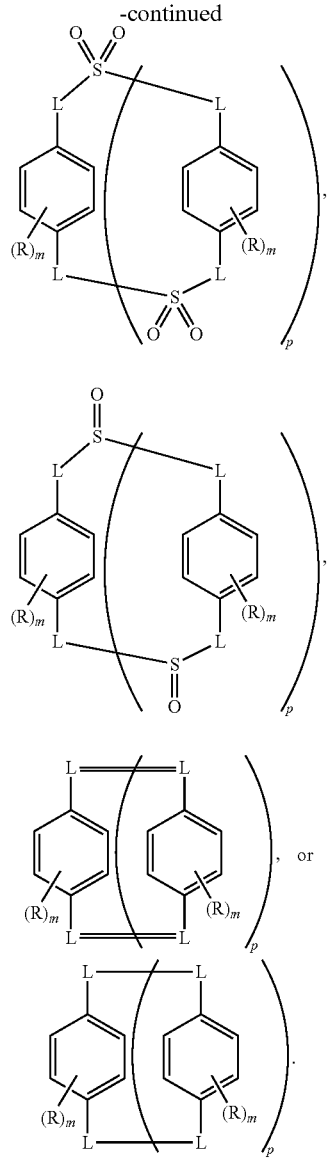

In some embodiments, each m is zero. In other embodiments, each R independently is alkoxy, particularly methoxy. In certain embodiments, each m is 2 and R is methoxy. In particular embodiment, the compounds have a formula Ib In certain embodiments of formula Ia, compounds have a formula selected from

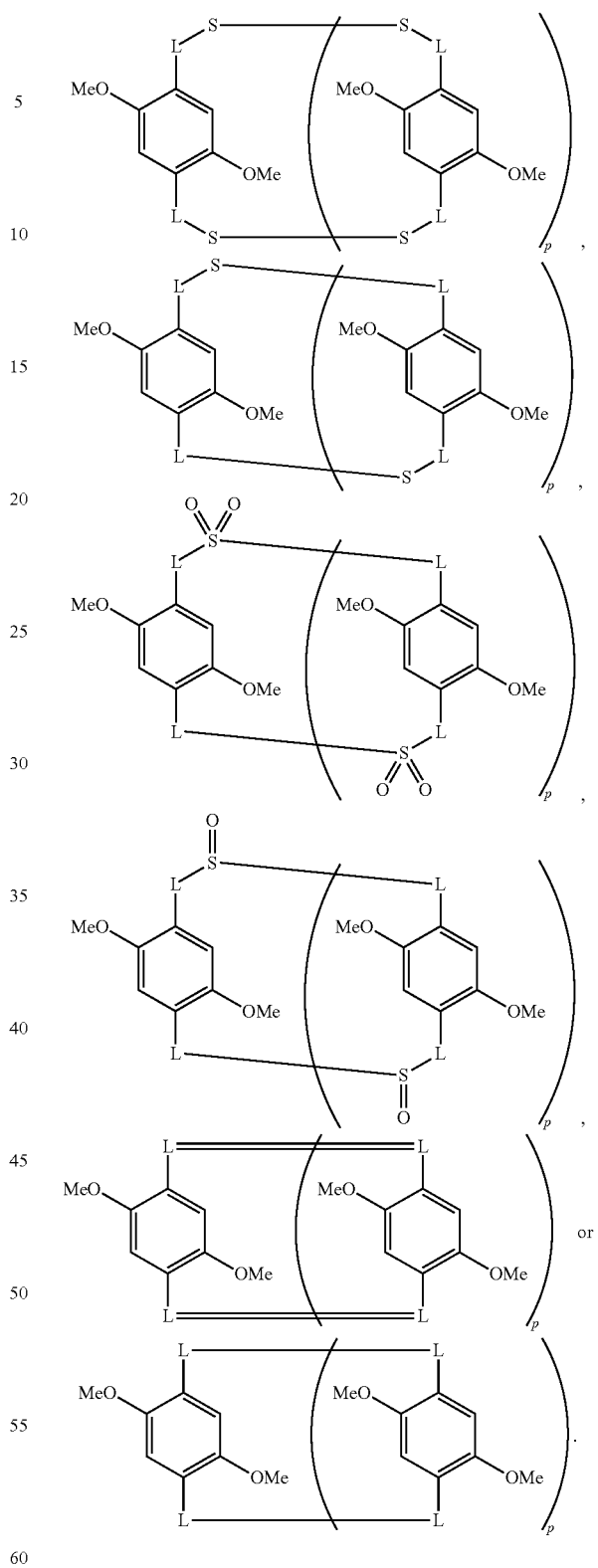

In some embodiments of formulas Ia and Ib, at least on L is CH₂, and in certain embodiments, all L's are CH₂. In some embodiments, p is 1, 2 or 3. In other examples, p is greater than 3, such as 4, 5, 6, 7, 8, 9 or 10.

Also disclosed herein are embodiments of a compound having a formula II

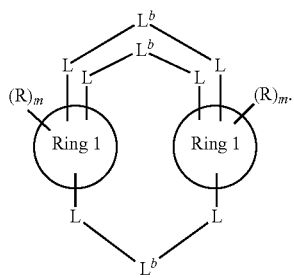

II

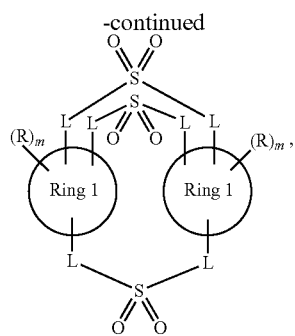

With respect to formula II, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; each L independently is a bond, aliphatic, aralkyl, aryl, heteroaryl or heteroaralkyl; and $L^b$ is —S—, —S(O)—, —S(O)$_2$, —S—S—, double bond or single bond. Also with respect to formula II, if ring 1 is phenyl, and each L is $CH_2$, then m is not 0.

In some embodiments of formula II, ring 1 is aryl, such as phenyl or naphthyl, but in other embodiments, ring 1 is heteroaryl, such as pyridine, triazine, imidazole, pyrazole, thiophene, furan, pyrrole or triazole. In certain embodiments, ring 1 is a triazine.

In some embodiments, at least one L is $CH_2$ and in certain examples, each L is $CH_2$. In other embodiments, at least one L is benzyl. In a particular embodiment, ring 1 is a triazine and each L is benzyl.

In some embodiments of formula II, the compounds have a formula selected from

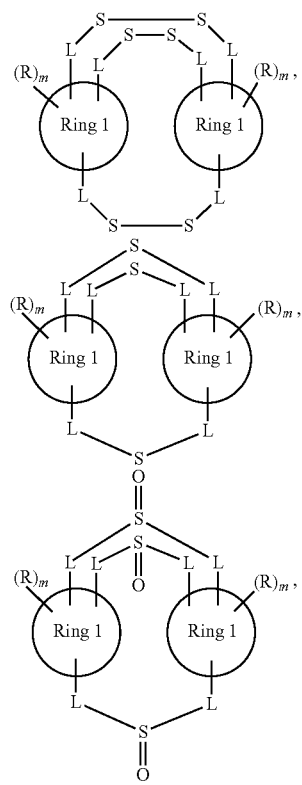

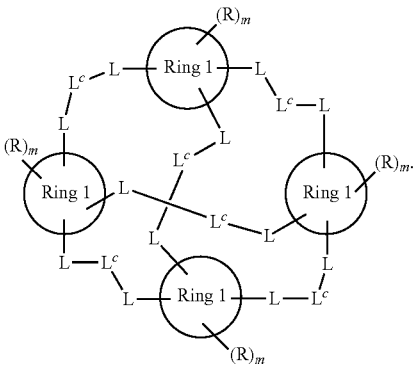

Compounds having a formula III are also disclosed herein

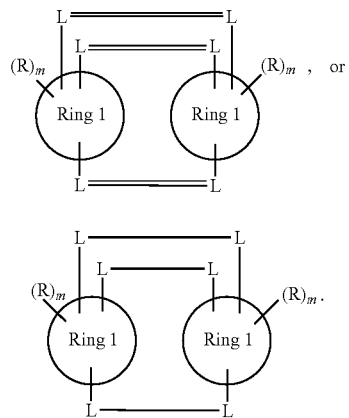

III

With respect to formula III, ring 1 is aryl or heteroaryl; each R independently is carboxyl ester, aminocarbonyl, aliphatic, heteroaliphatic, $NO_2$, sulfonyl, amine, protected amine, aryl, heteroaryl, OH, oxo or halogen; m is from 0 to 4; each L independently is a bond, aliphatic, aralkyl, aryl, heteroaryl or heteroaralkyl; and $L^c$ is —S—, —S(O)—, —S(O)$_2$, —S—S—, double bond or single bond. Also with respect to formula III, if ring 1 is phenyl, each L is $CH_2$, and m is 0 then $L^c$ is not a single bond, and if ring 1 is phenyl, one L is benzyl and the other two L moieties are $CH_2$, and m is 0, then $L^c$ is not a single bond. In some embodiments, ring 1 is aryl, such as phenyl, naphthyl or anthracenyl, but in other embodiments, ring 1 is heteroaryl, such as pyridine, triazine, imidazole, pyrazole, thiophene, furan, or triazole. In some examples, each L is $CH_2$, and in other embodiments, each L is benzyl. In particular embodiments, ring 1 is triazine or phenyl and each L is benzyl.

In some embodiments of formula III, the compounds have a formula selected from
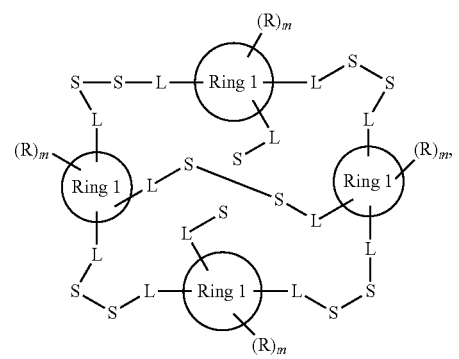
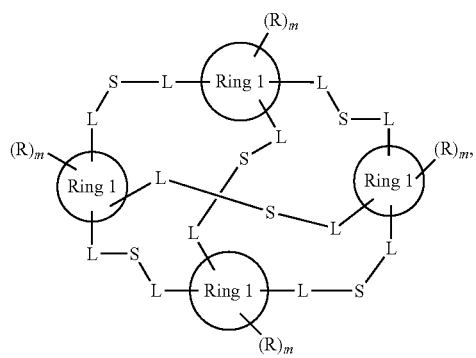
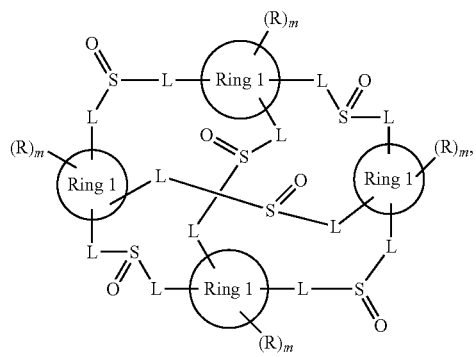
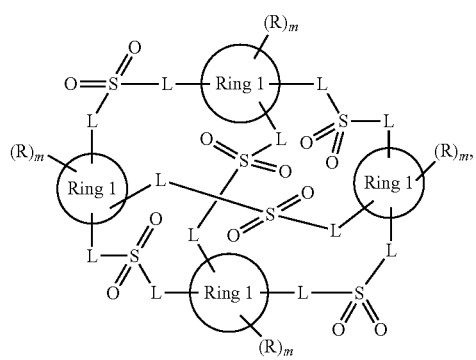
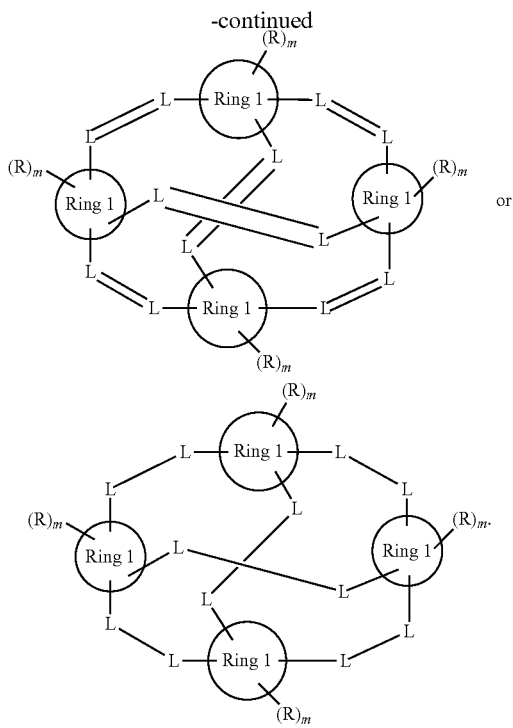
In certain embodiments of formula II and formula III, the
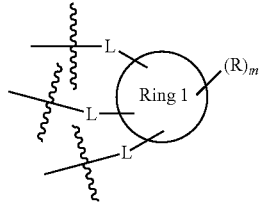
moiety has a formula selected from
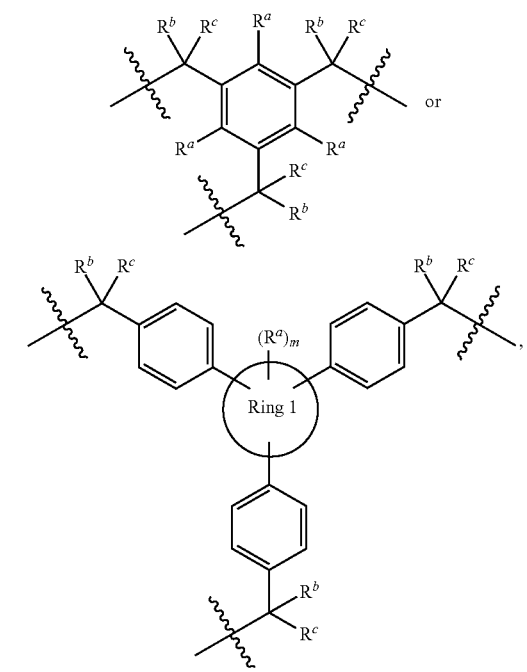
Wherein ring 1, $R^a$, $R^b$, and $R^c$ are as defined above, and m is from 0 to 3.

In some embodiments, compounds comprising the
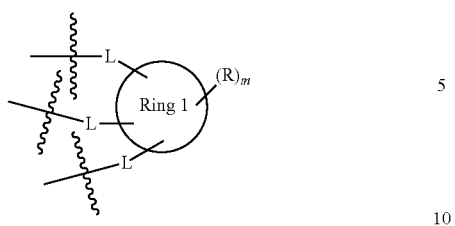
moiety have a cage-like structure larger than a tetrahedron, such as comprising 6, 8, 10, 12, 14, 16, 18, 20, 22, 24 or more linker moieties. In certain embodiments, the cage-like structure comprises 12 or 24 linker moieties.
In certain embodiments, the compound is selected from
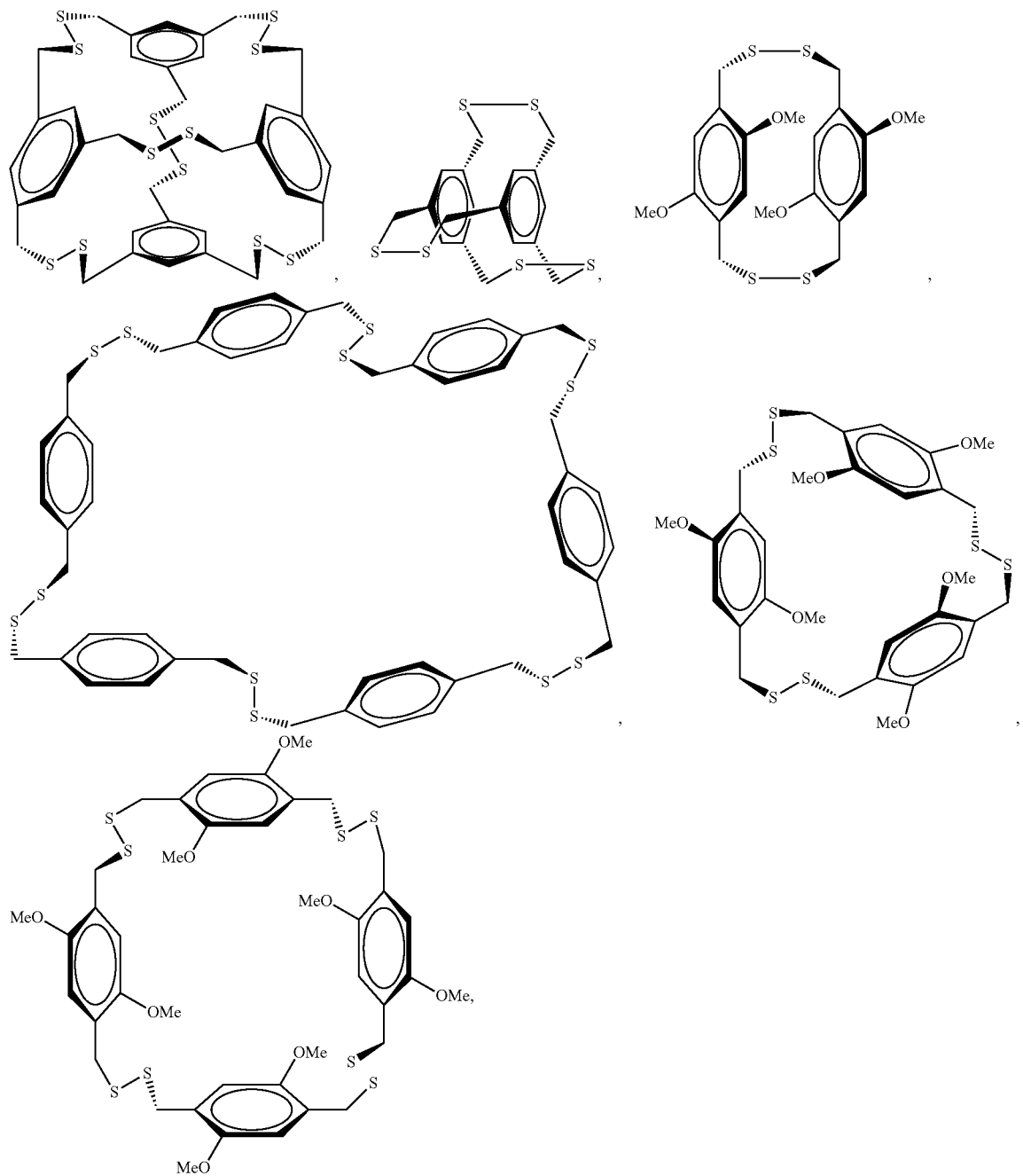

-continued
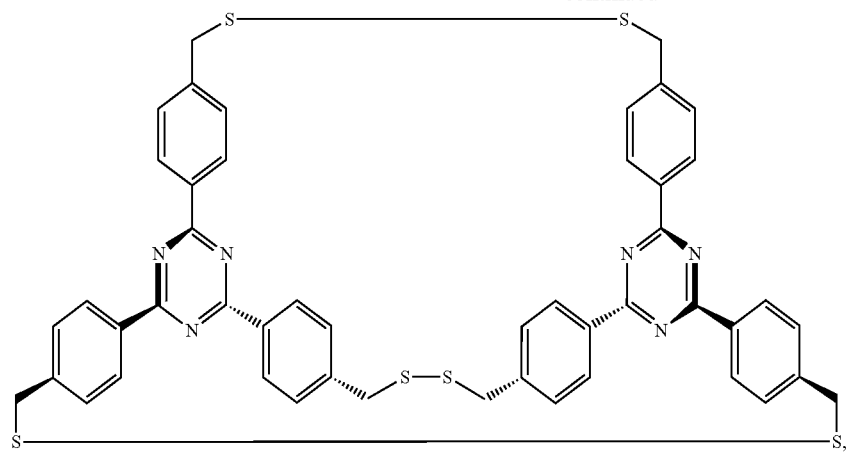
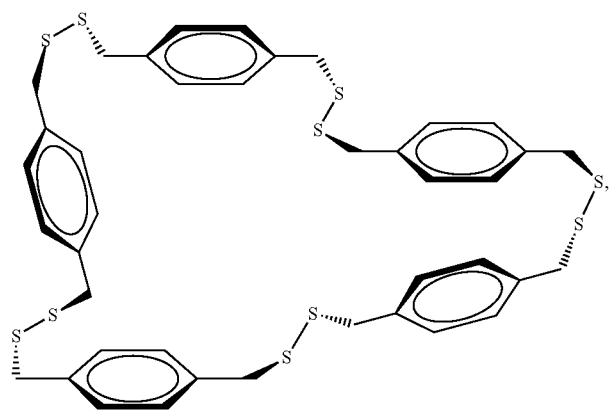
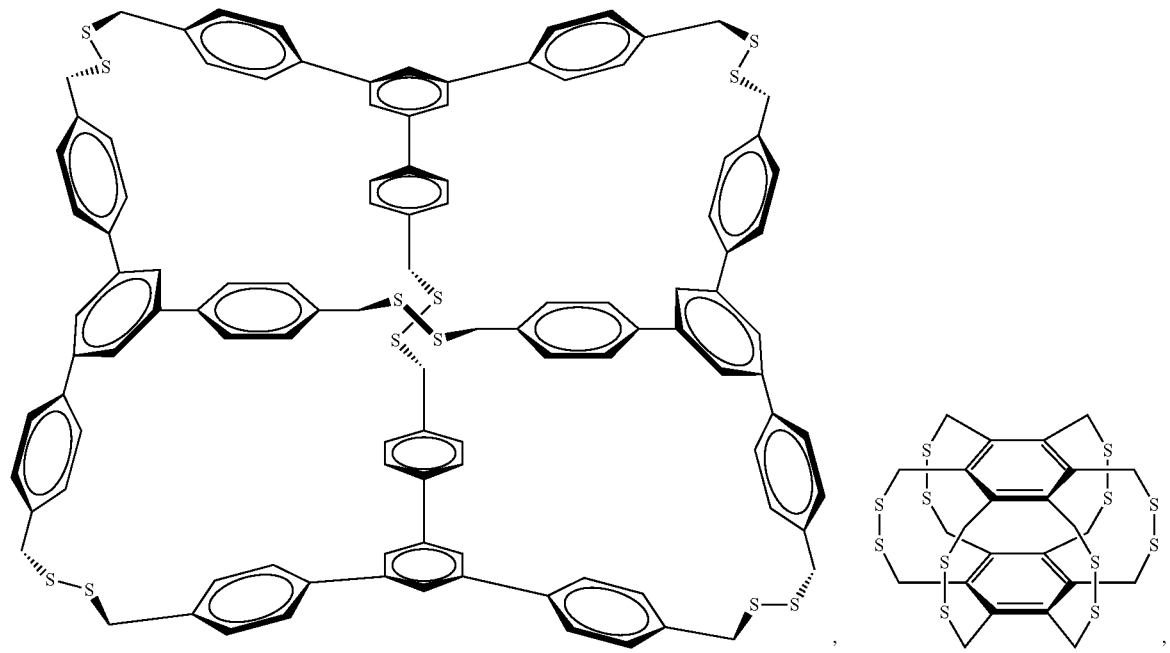

-continued
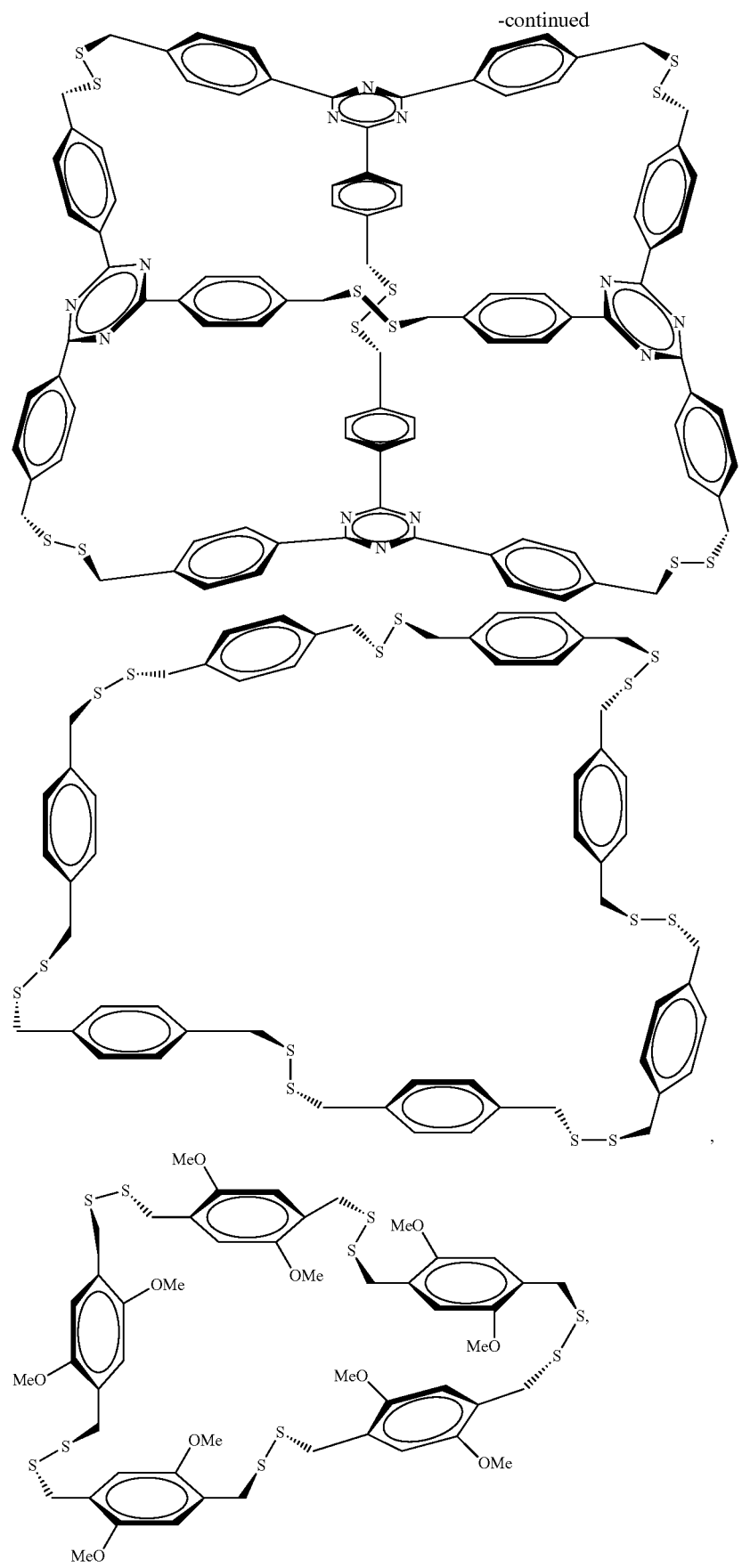

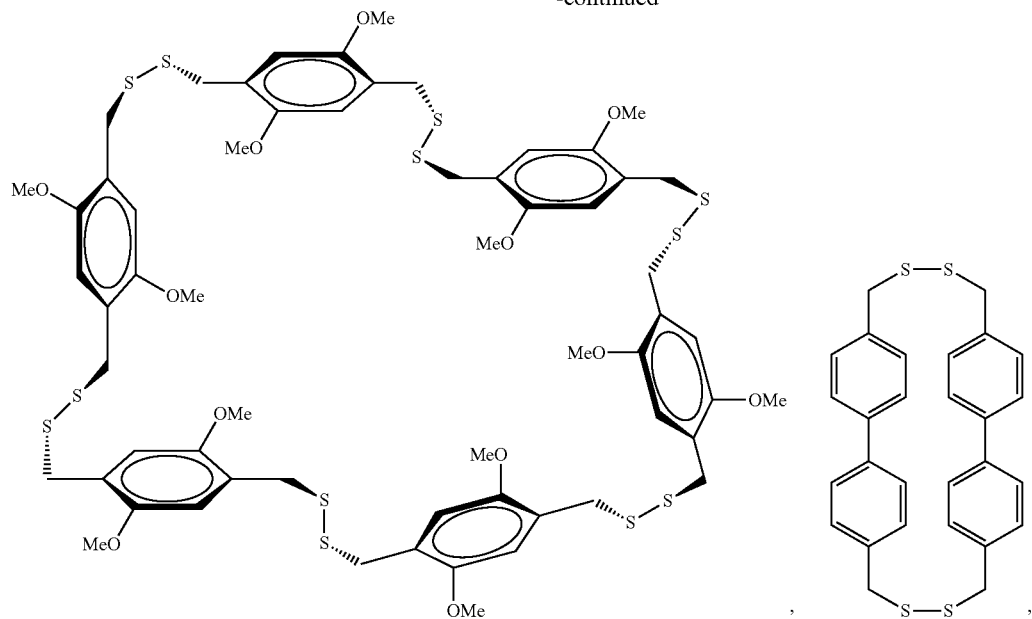
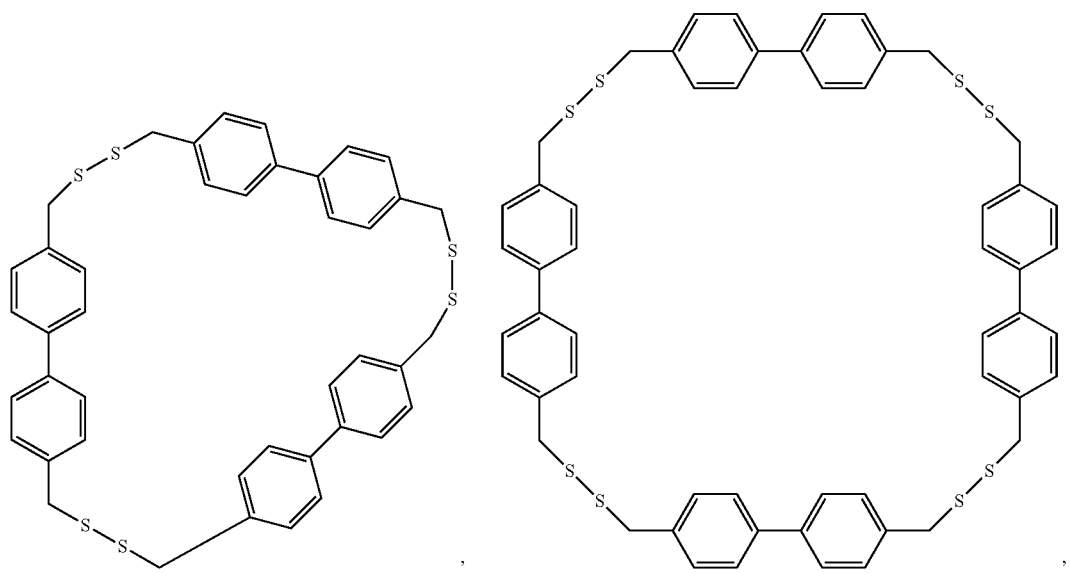
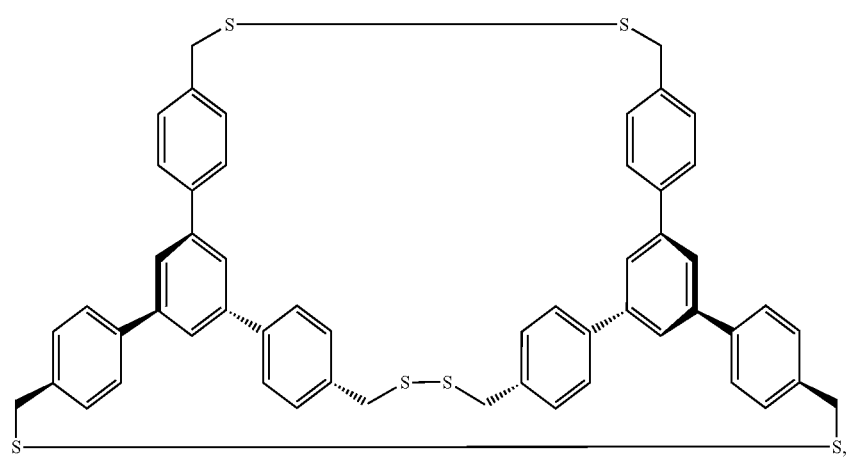

-continued
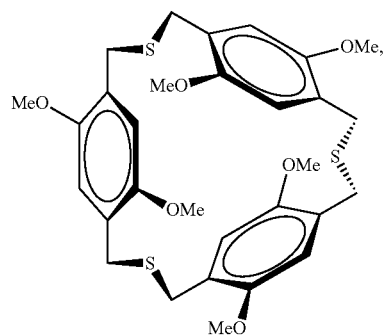
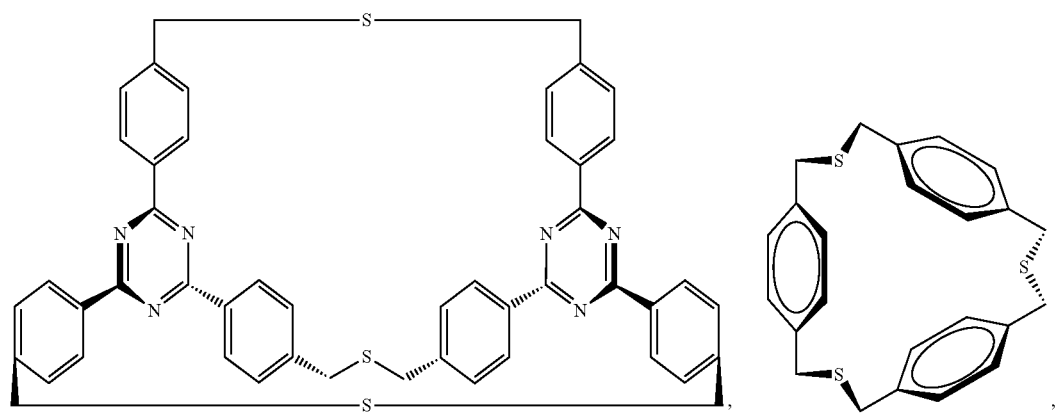
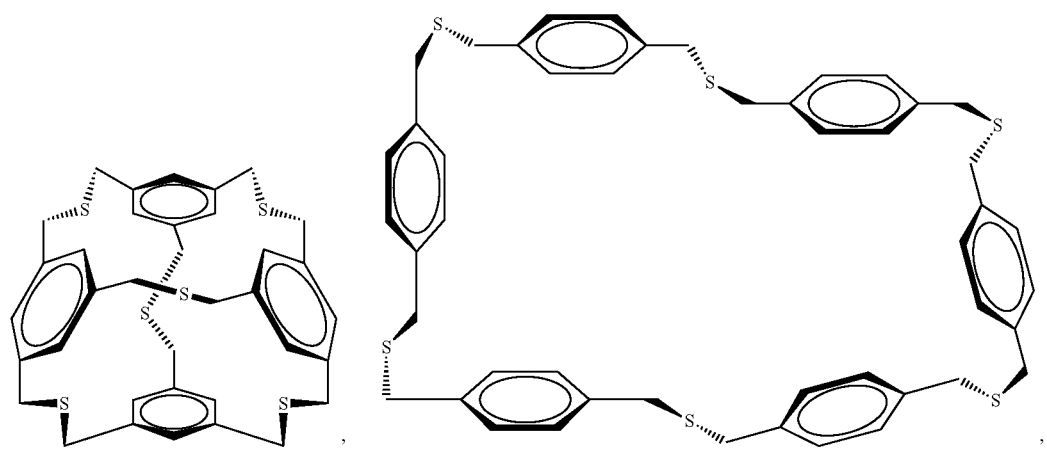
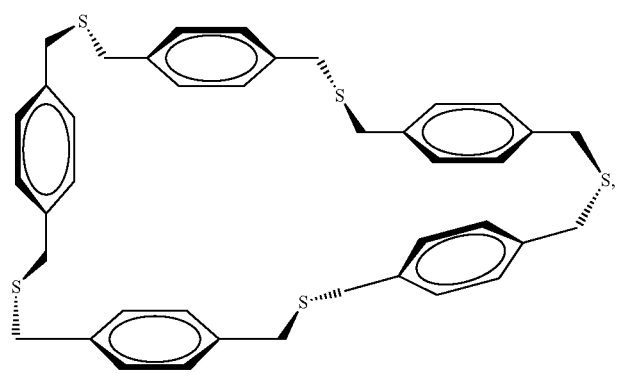

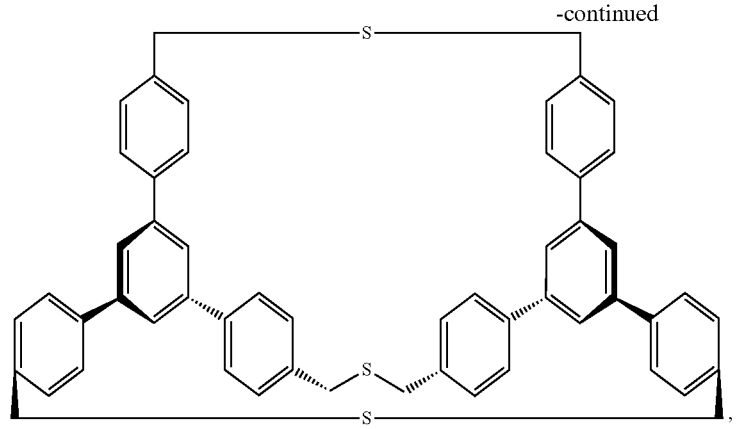
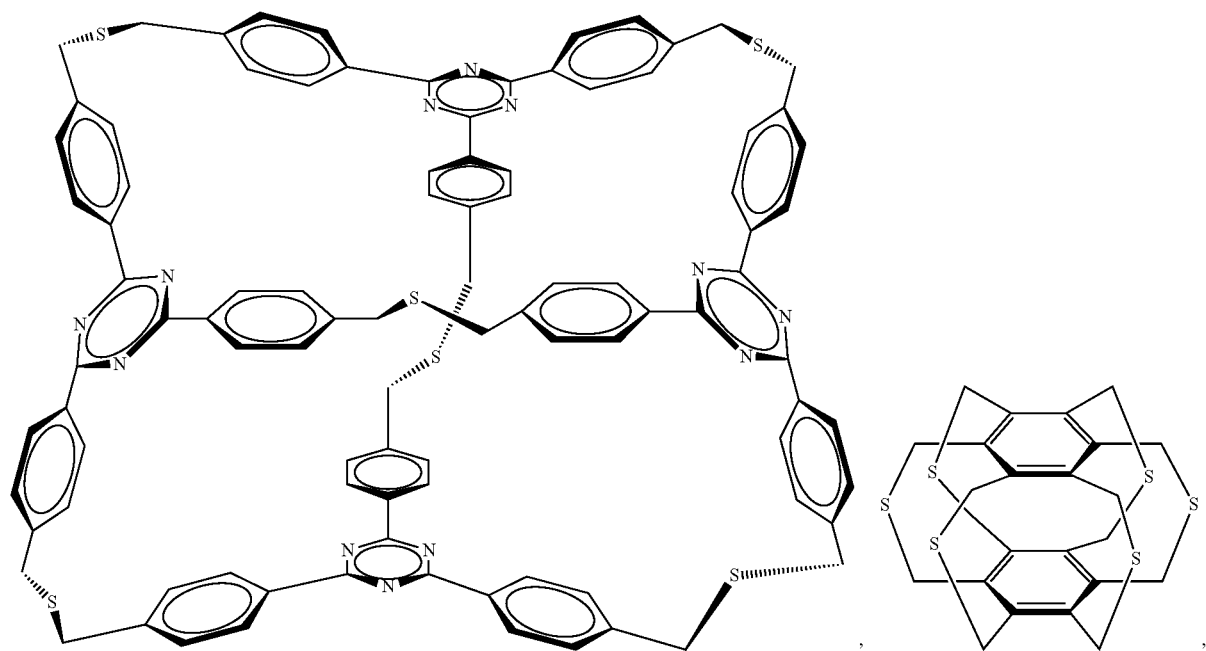
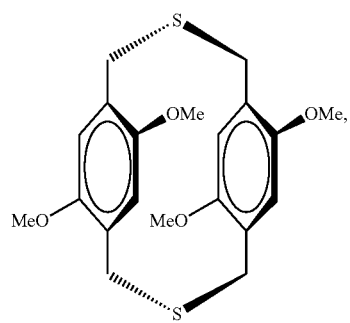

-continued
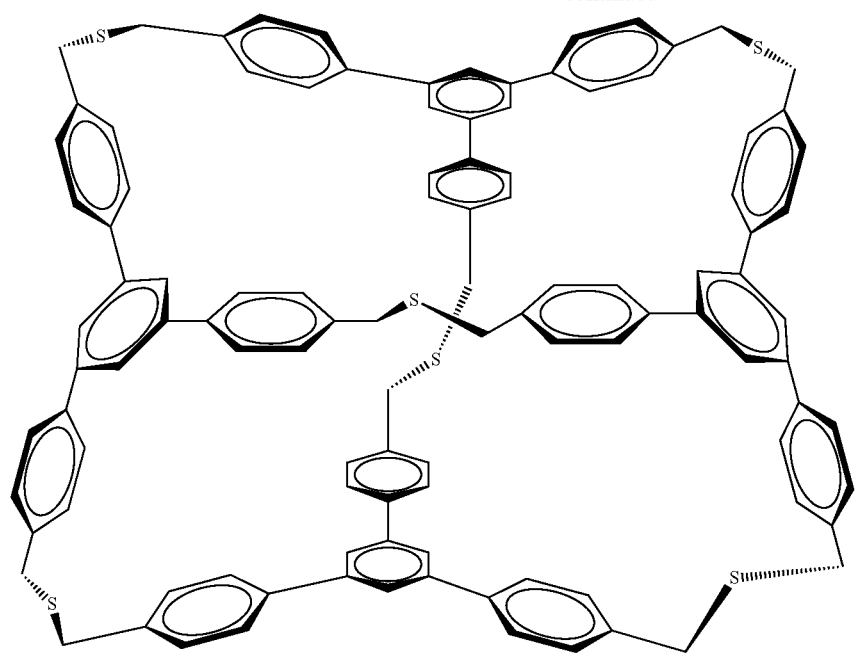
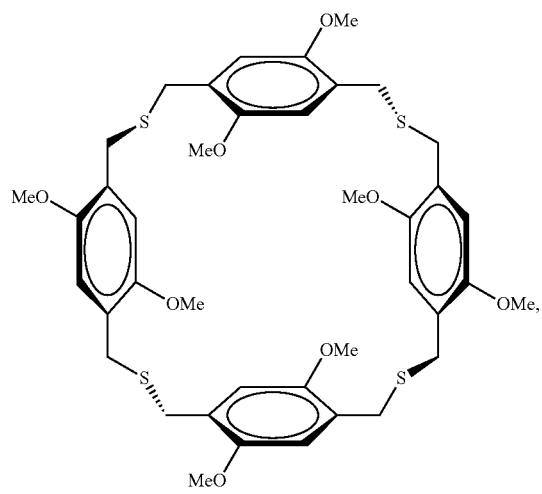
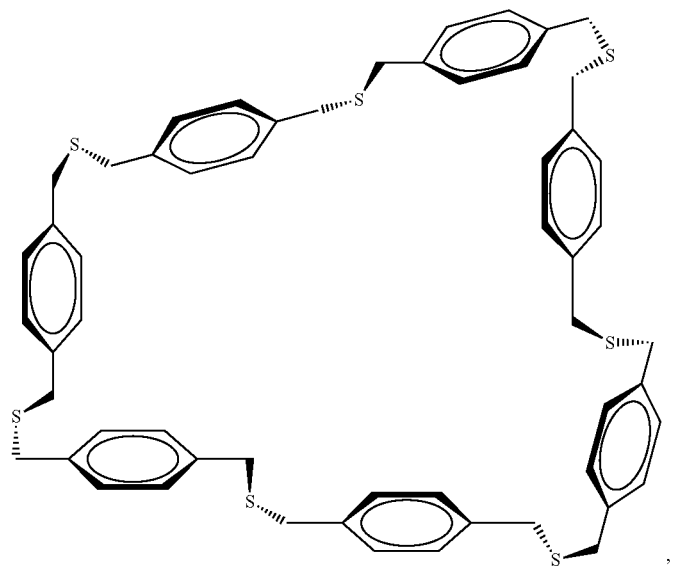

-continued
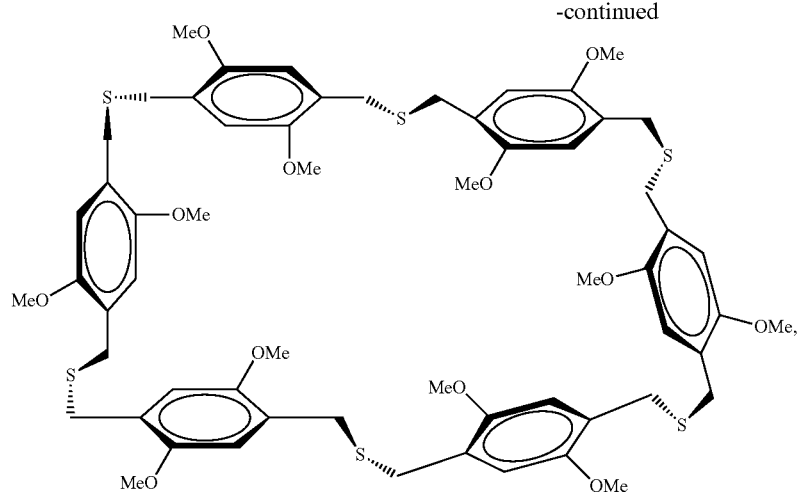
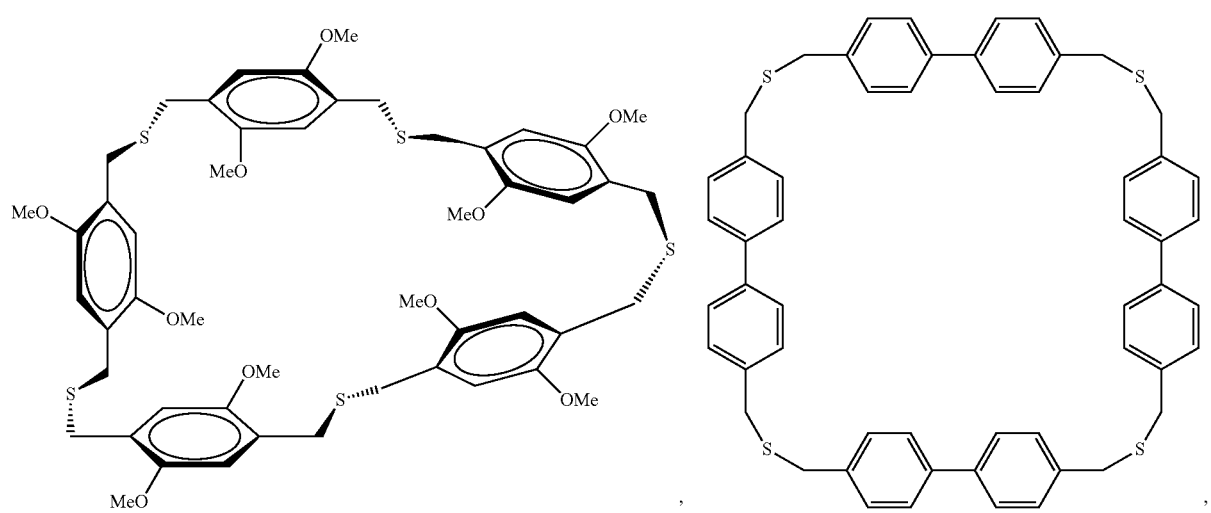
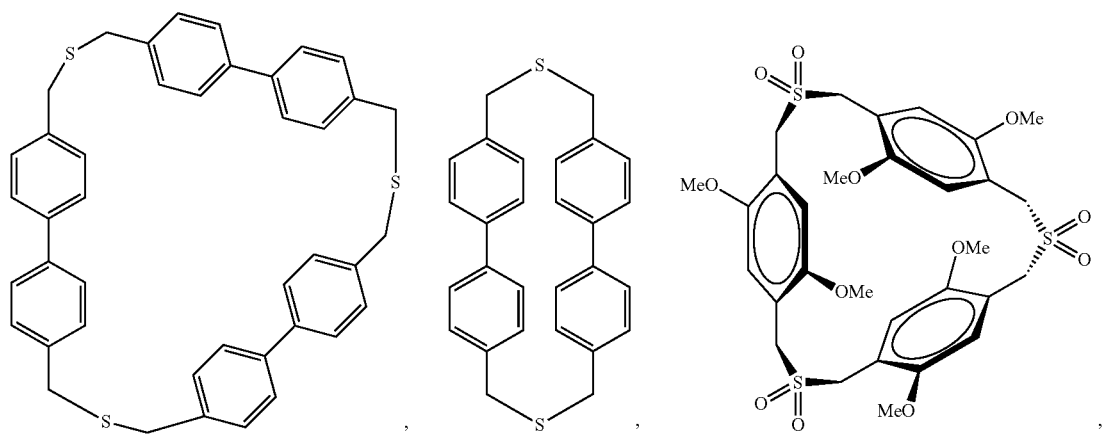

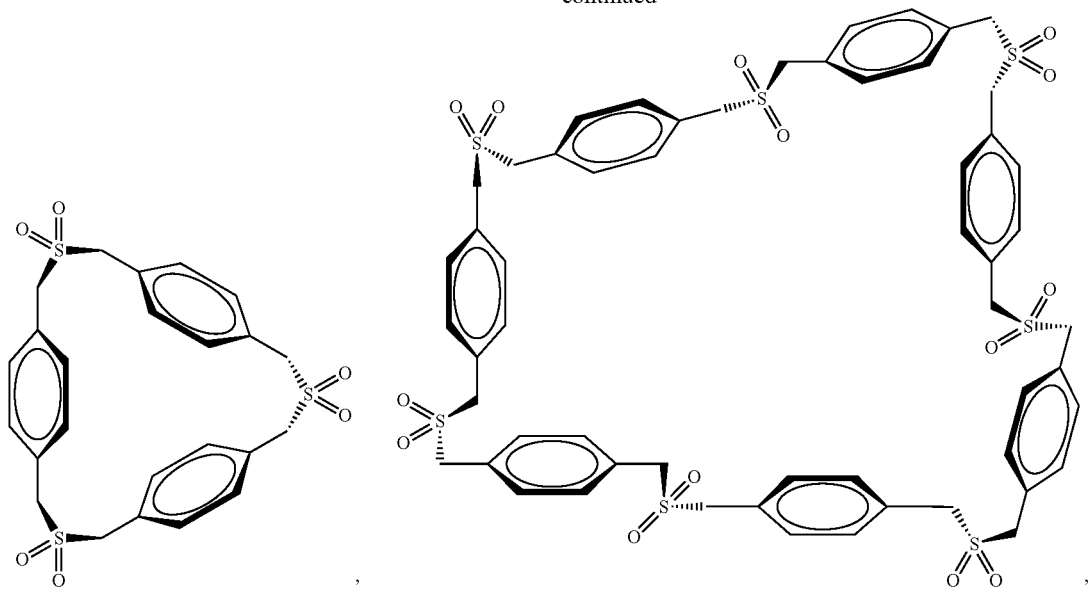
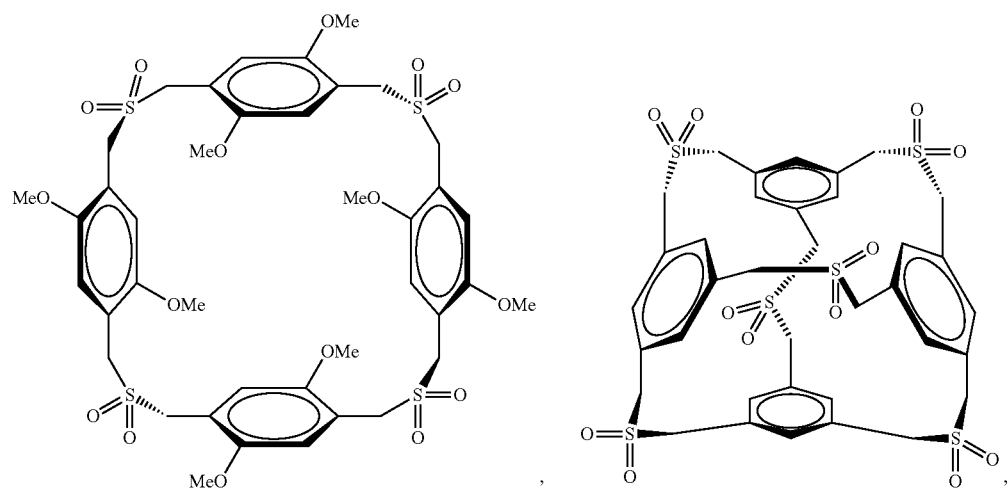
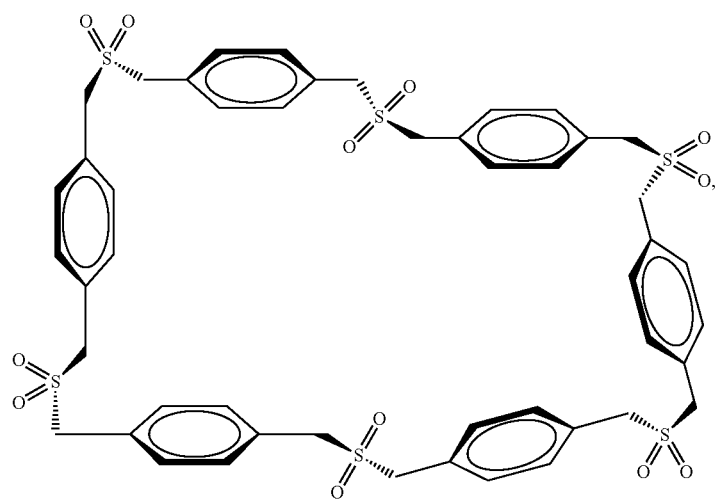

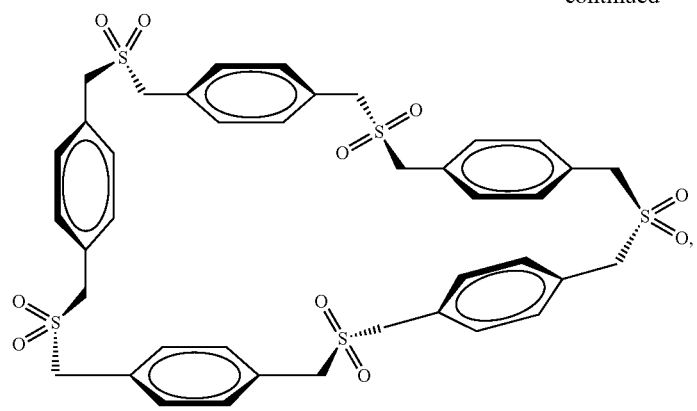
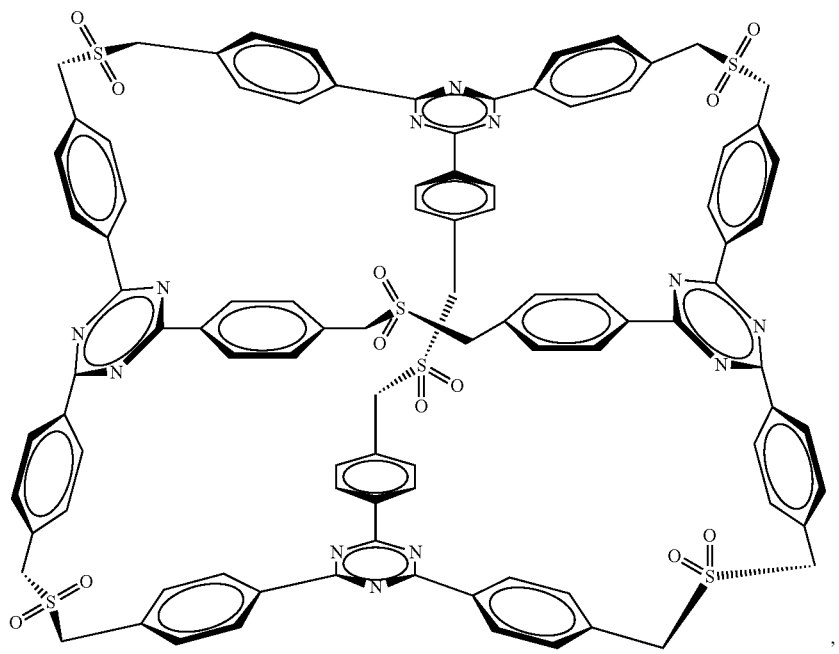
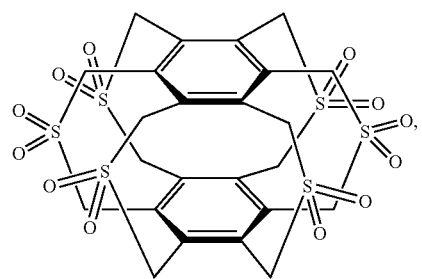

-continued
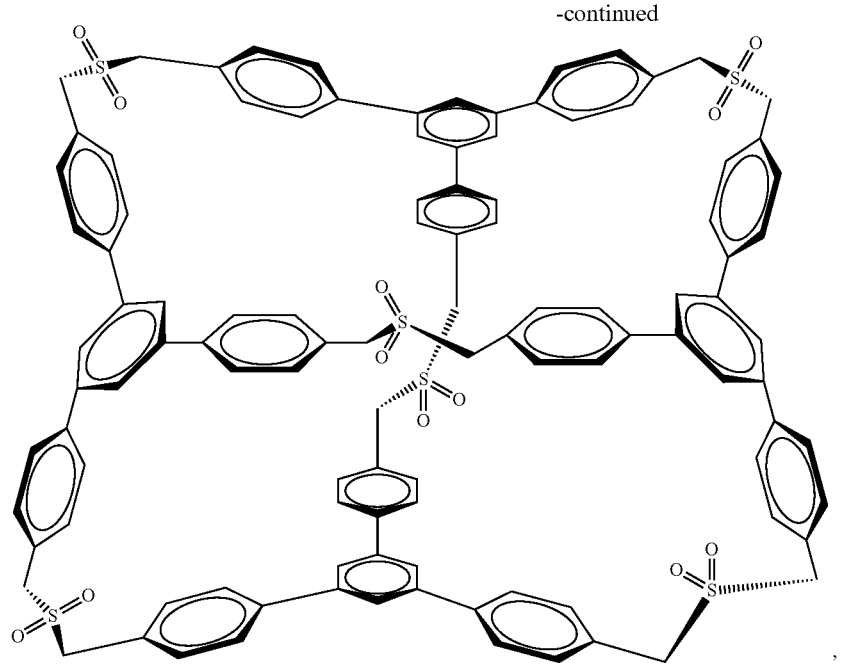
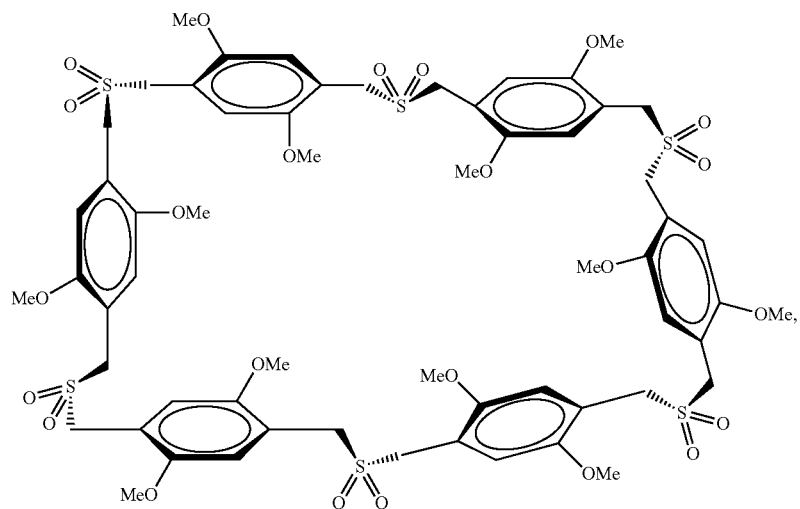
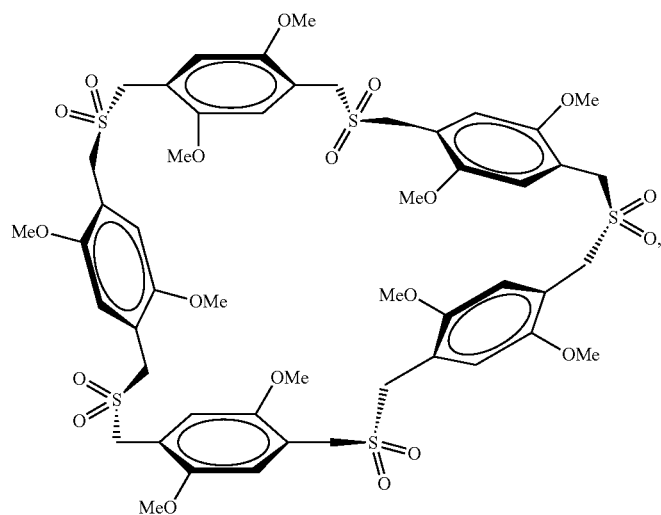

-continued
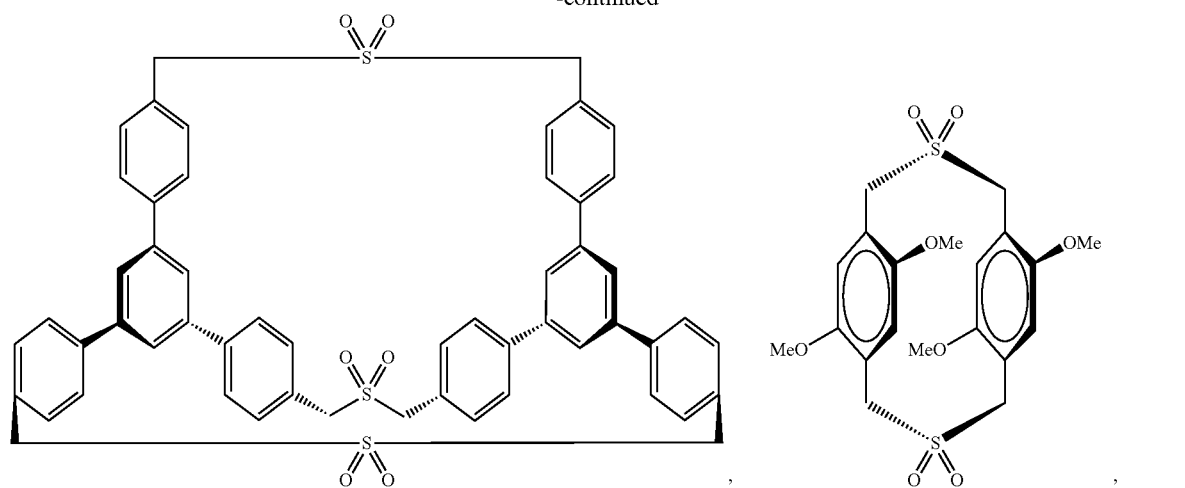
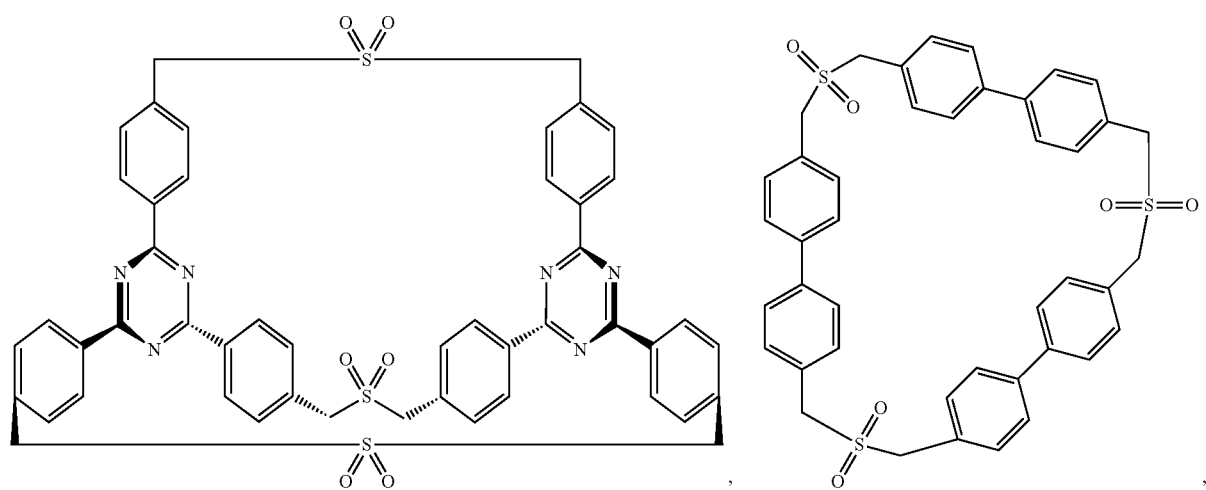
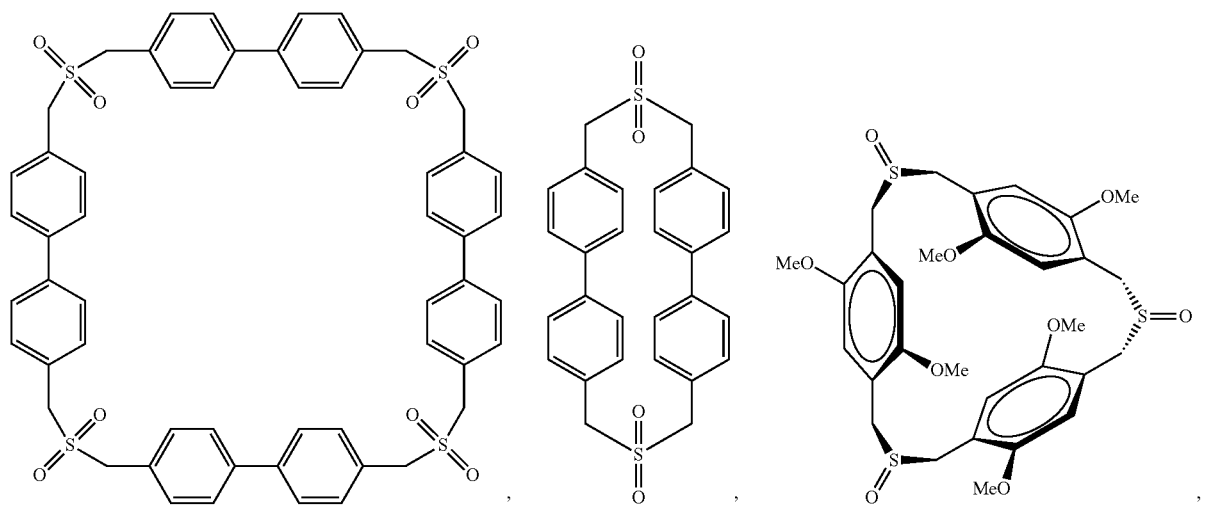

-continued
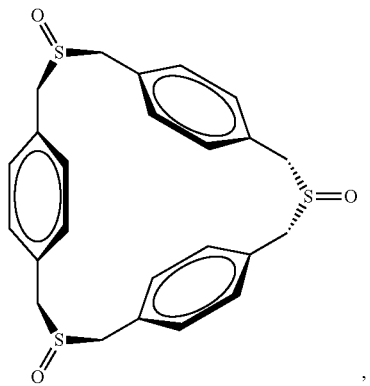
,
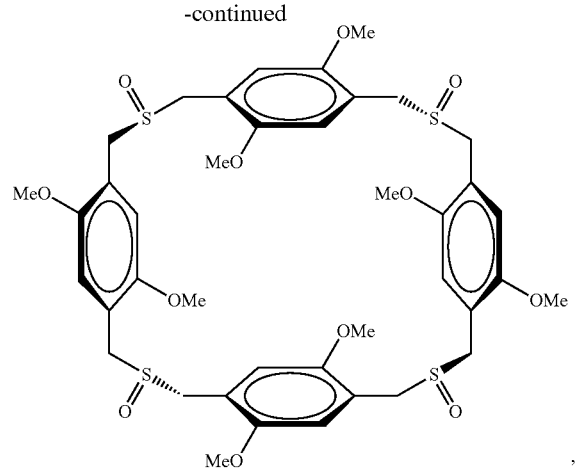
,
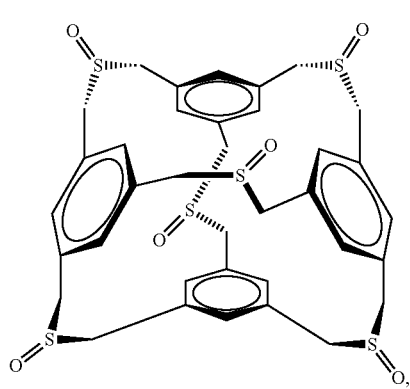
,
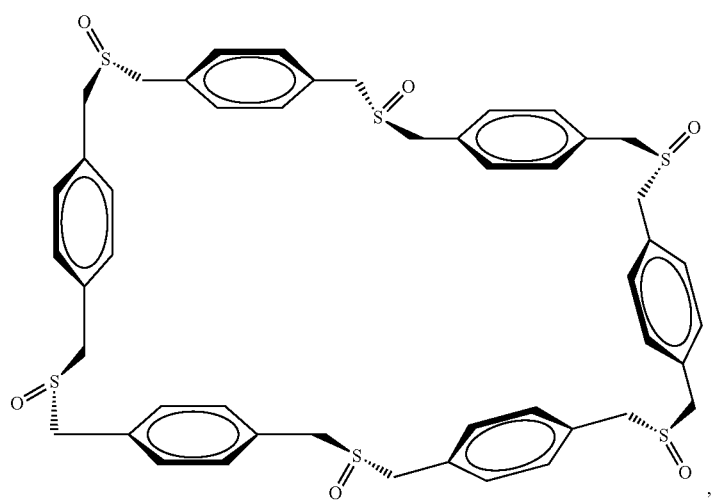
,
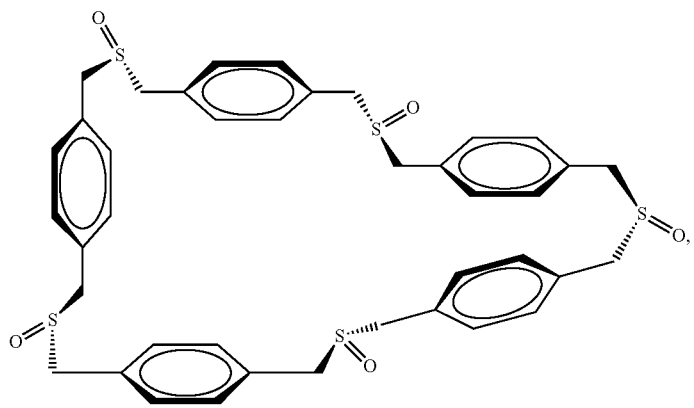

-continued
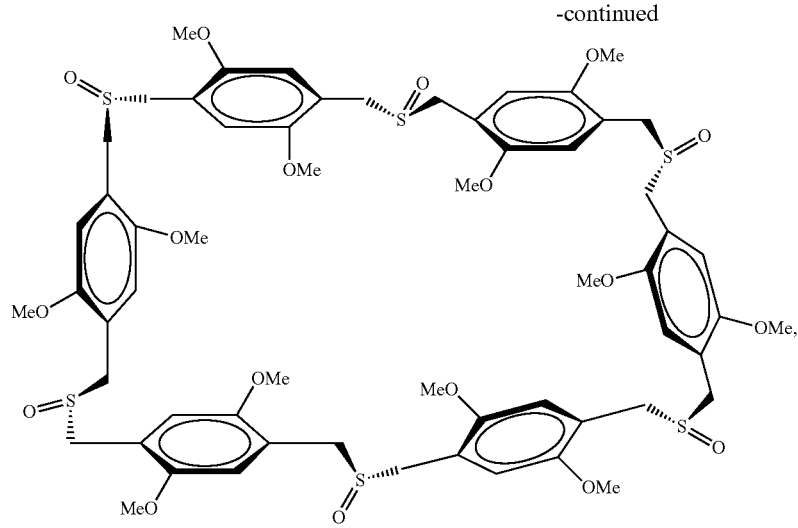
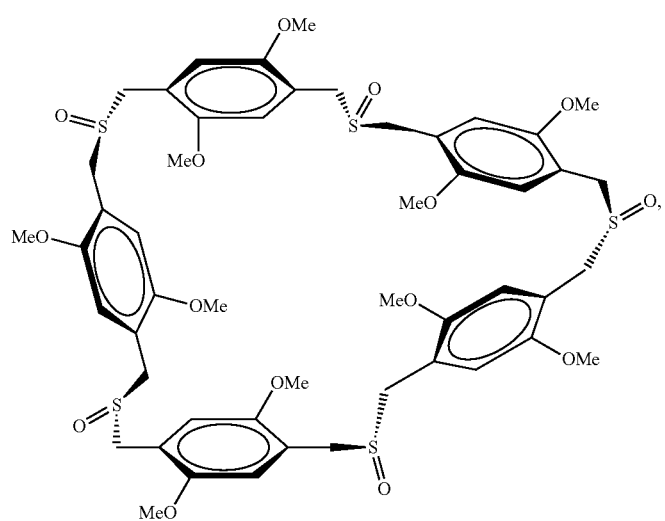
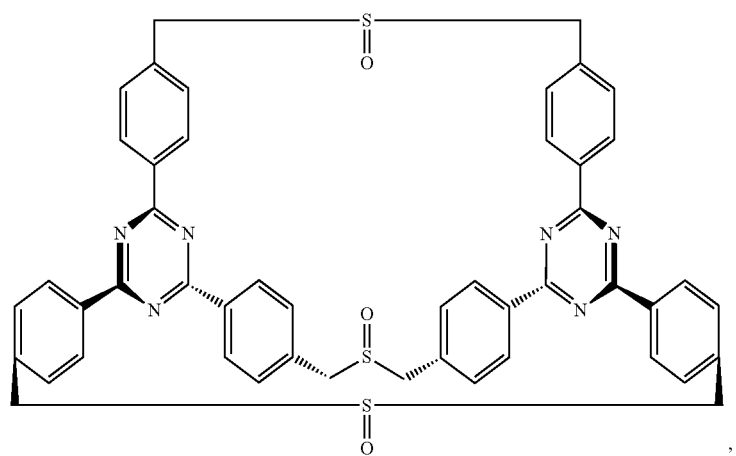
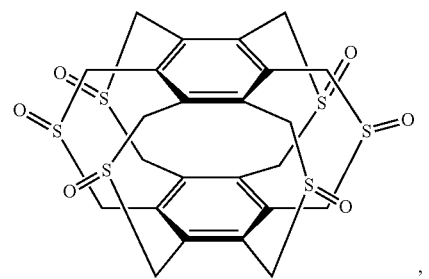

-continued
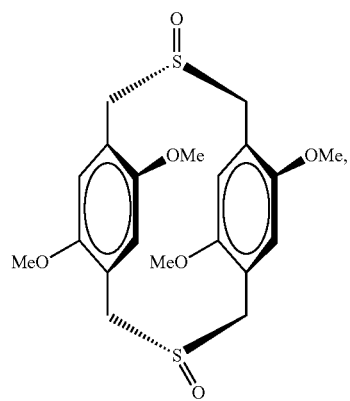
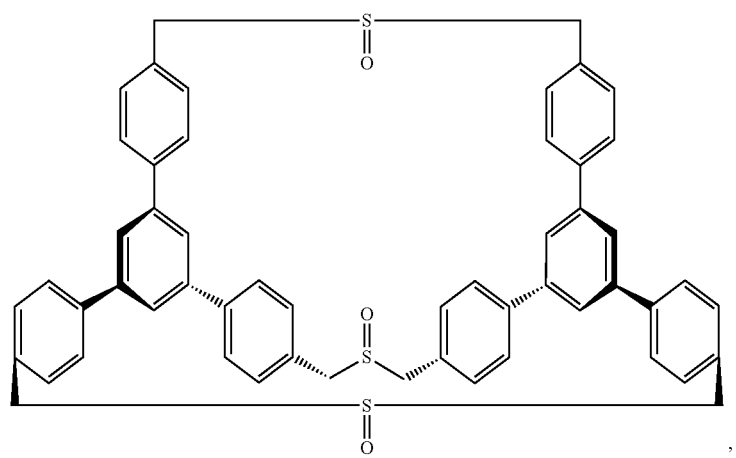
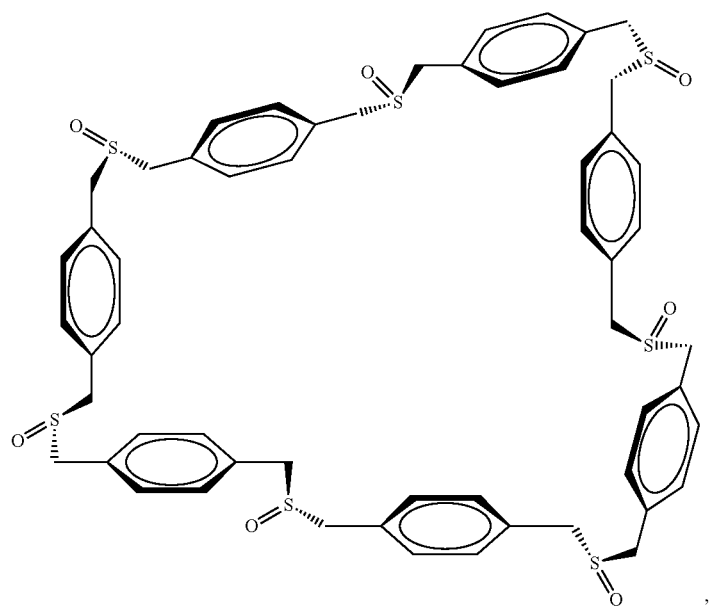

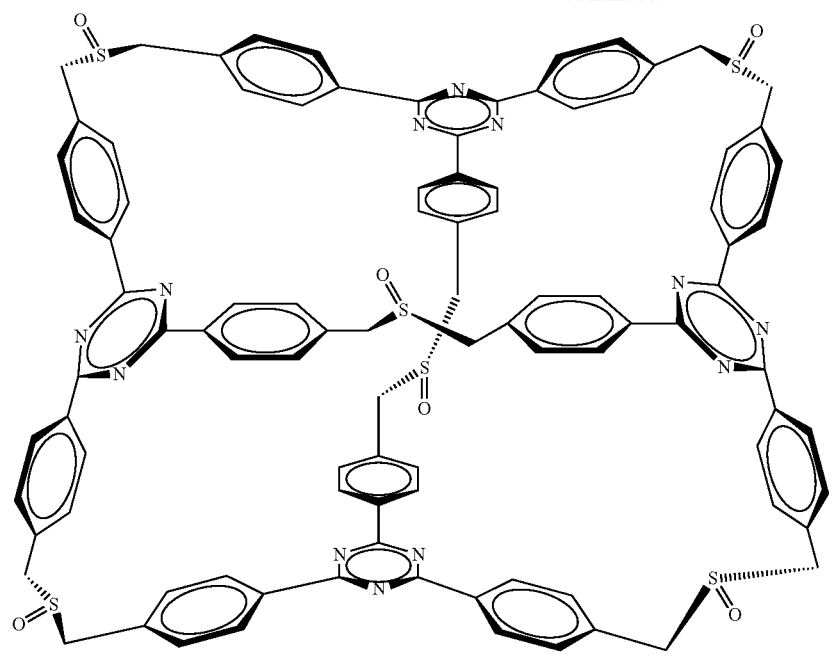
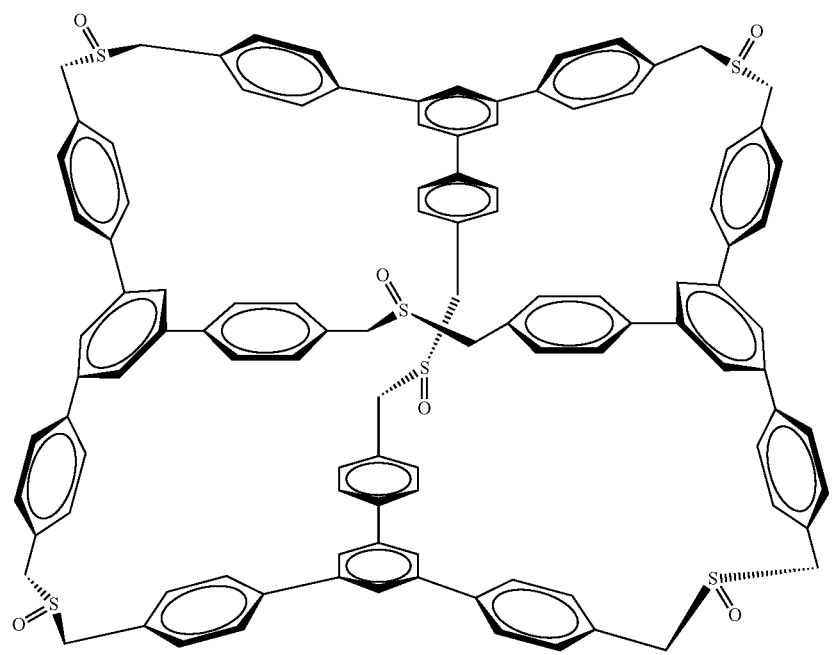
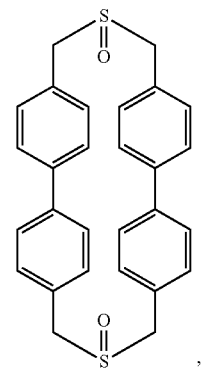

-continued
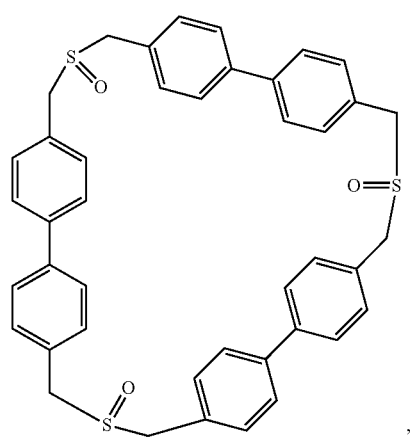
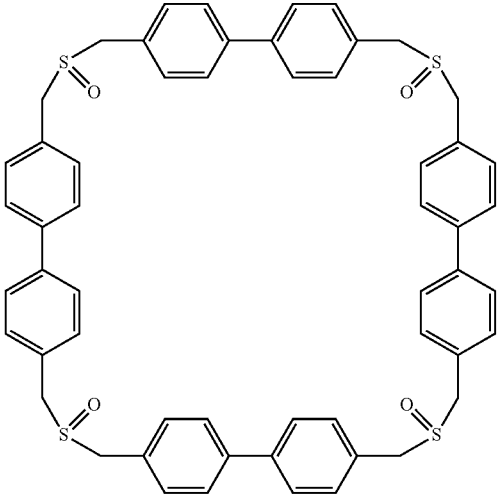
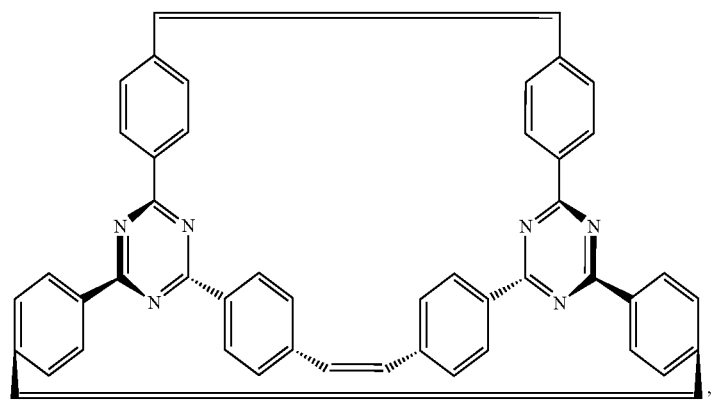
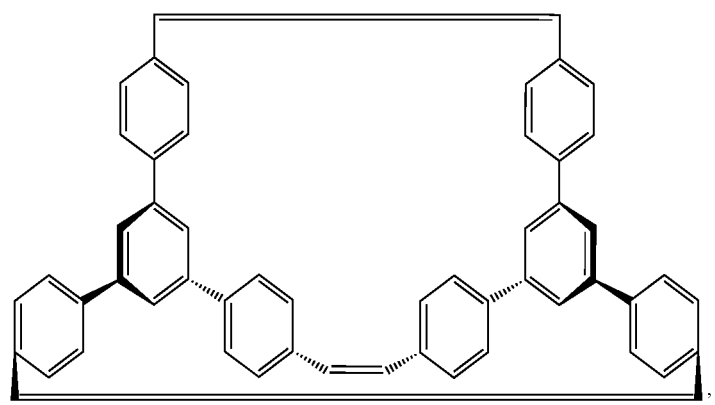
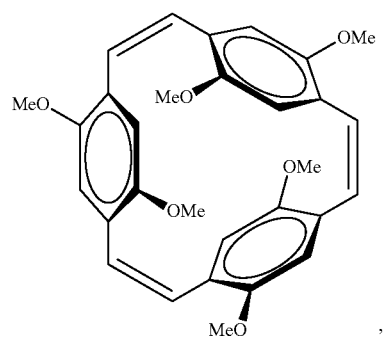
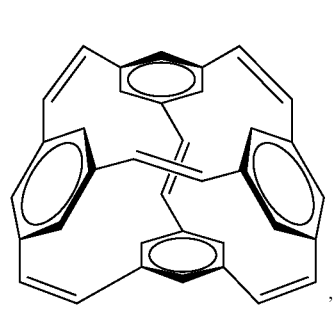
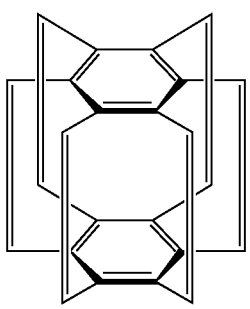
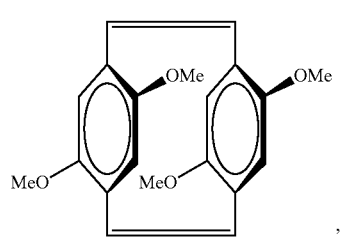

57
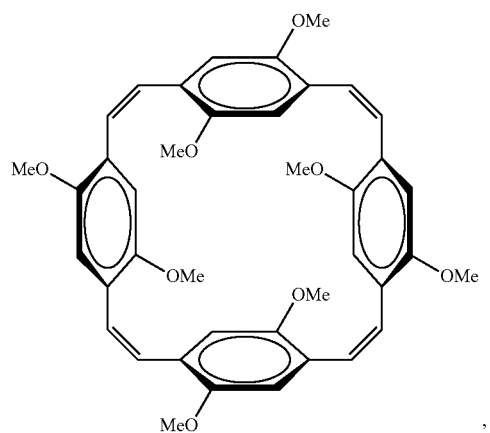
,
58
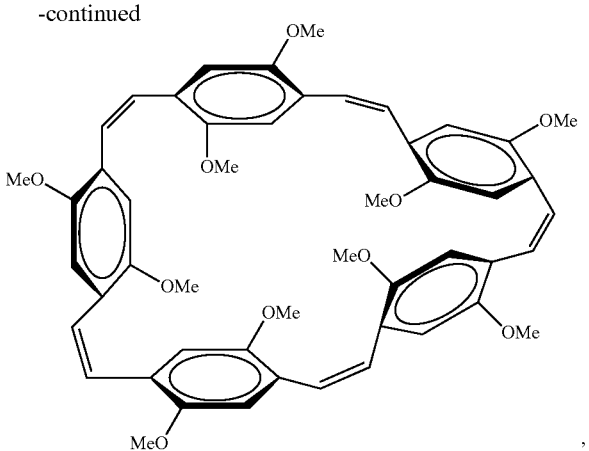
,
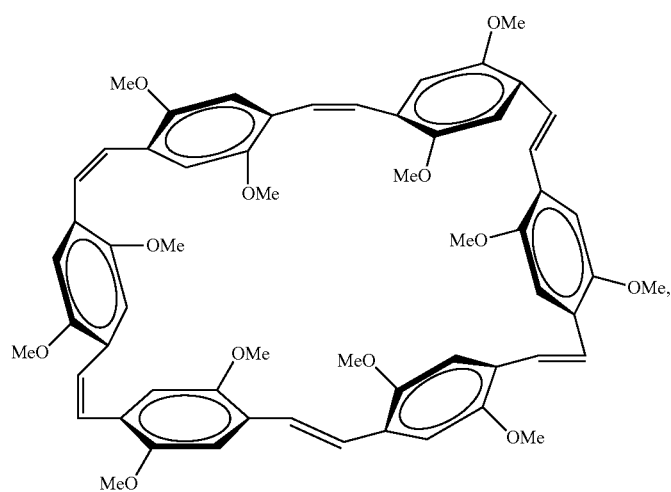
,
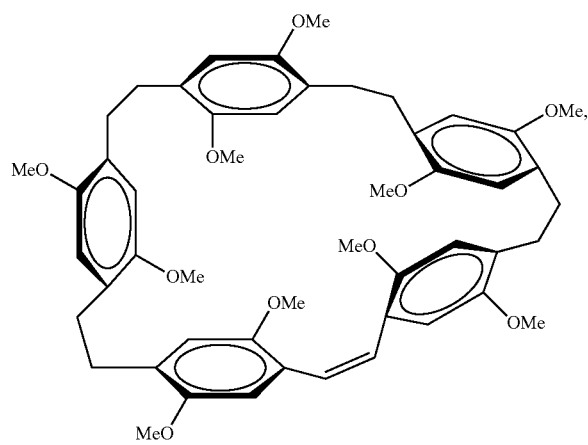

-continued
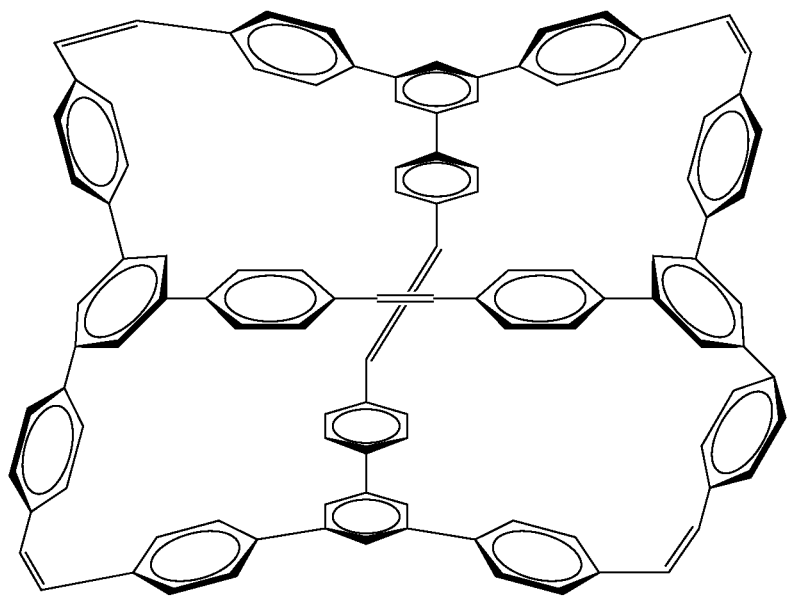
,
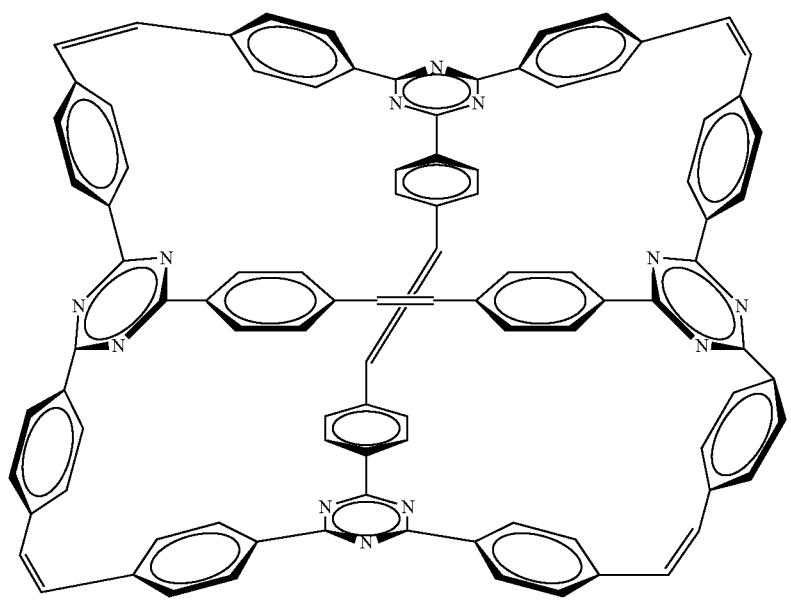
,
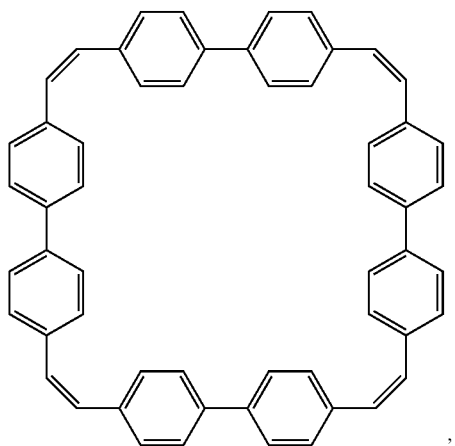
, 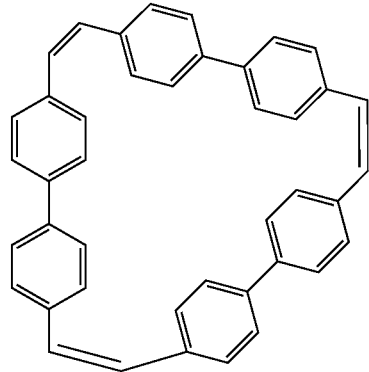, 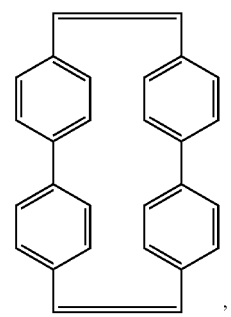,

61
-continued
62
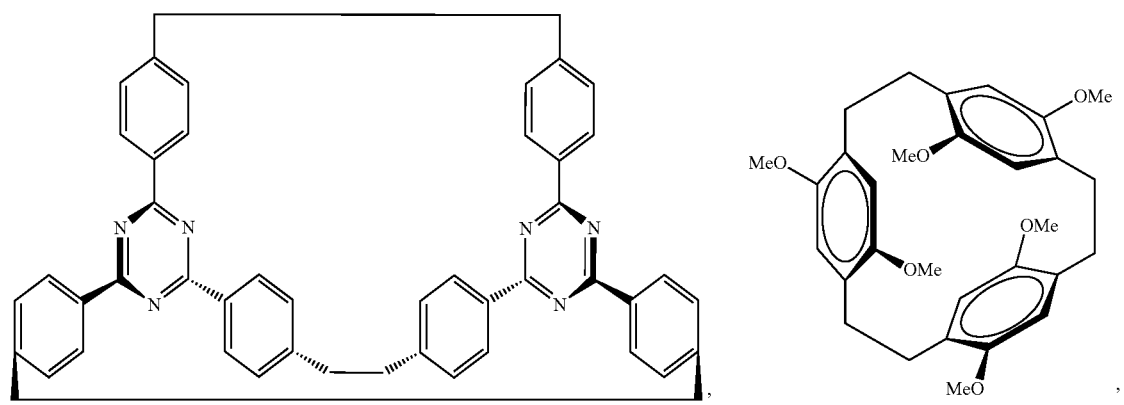
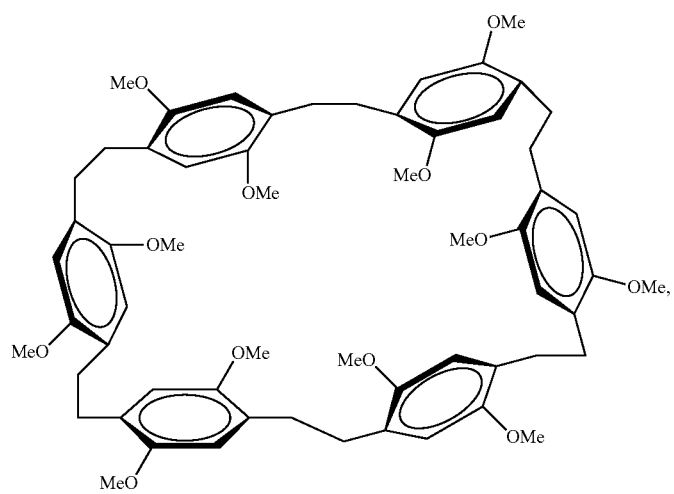
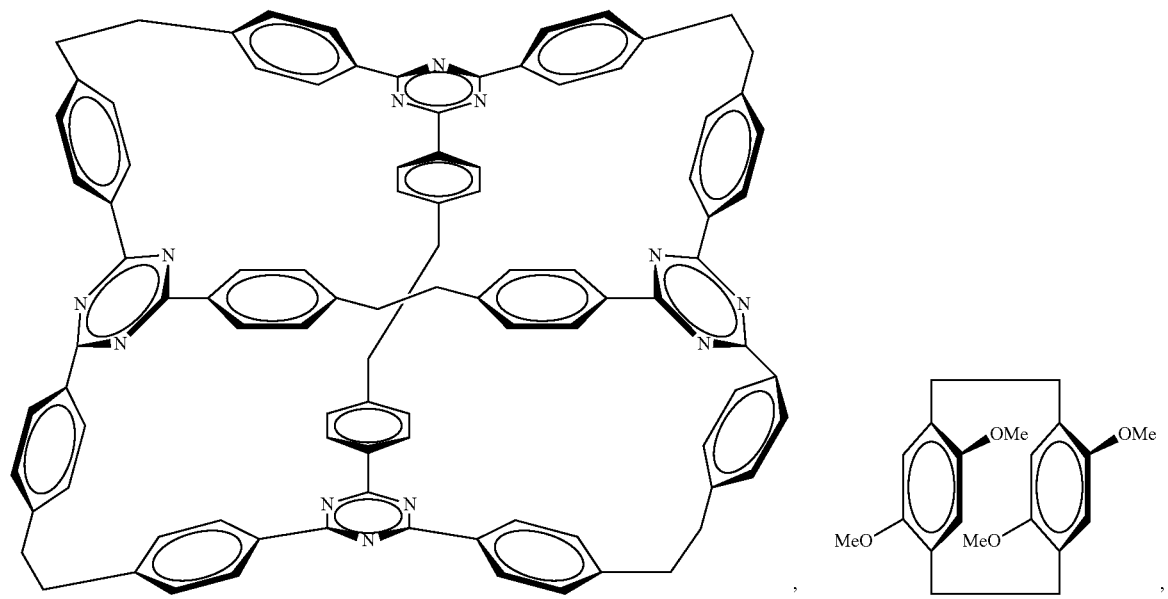

-continued

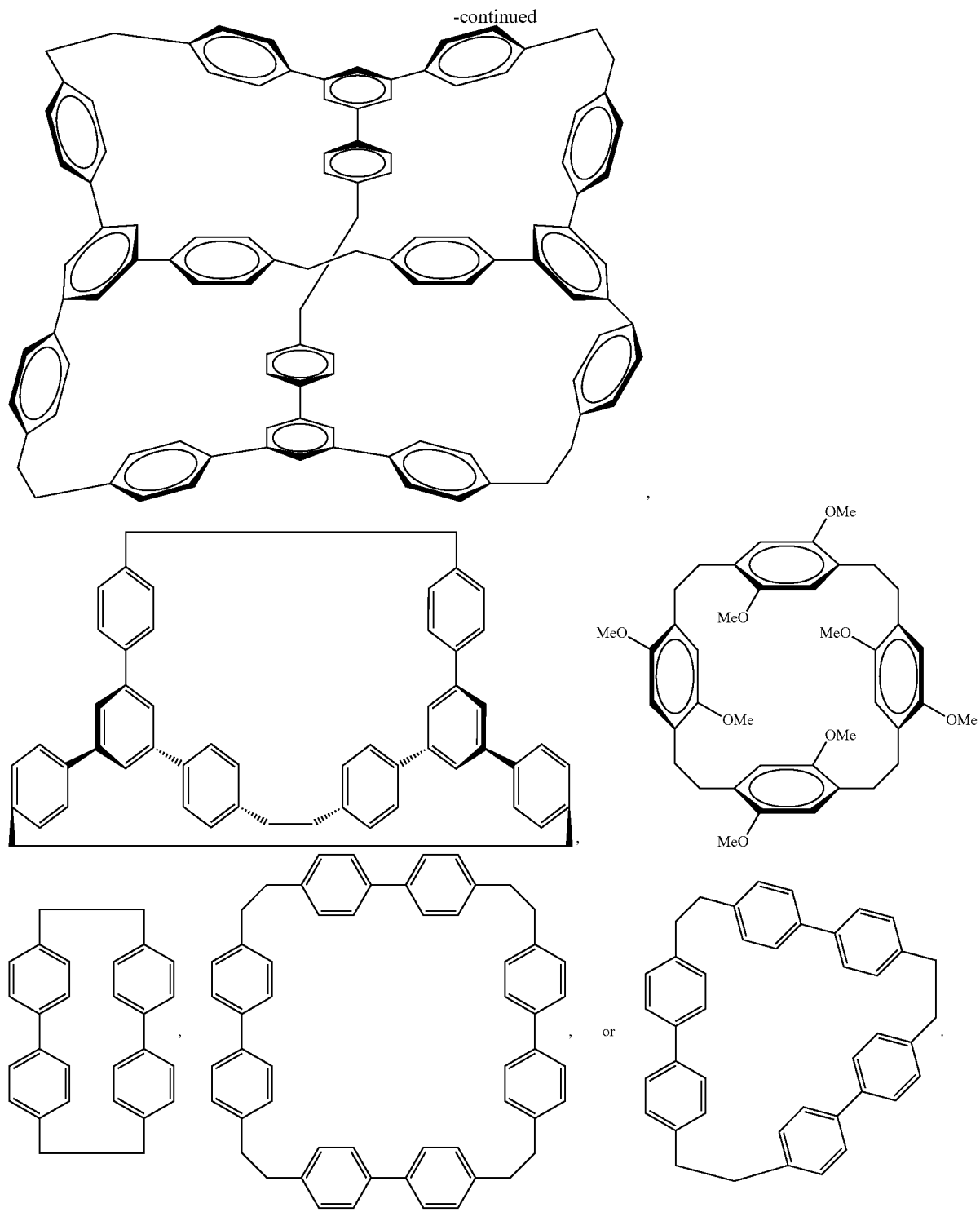

III. Methods of Making the Compounds

A general method of making the disclosed compounds comprises forming a disulfide cyclophane by contacting a linker with a metal salt, and an oxidant, the linker comprising an aromatic ring and a plurality of thiol groups, and then forming a thiacyclophane by desulfurization of the disulfide cyclophane. The linker can be any suitable linker that comprises at least one aromatic unit, such as an aryl ring, heteroaryl ring, or a combination thereof, and two or more thiol groups. The thiol groups may be attached directly to the aromatic unit, or they may be attached to an aliphatic or heteroaliphatic chain or ring, which is in turn attached to the aromatic unit. Suitable aromatic units include, but are not limited to, phenyl, naphthyl, biphenyl, terphenyl, quaterphenyl, 1,3,5-triazinyl or 2,4,6-triphenyl-1,3,5-triazinyl. The thiol-containing groups may be attached at any positions suitable to form the desired cyclophane. In some embodiments, the thiol-containing groups are attached to the aromatic units at any suitable non-adjacent positions, such as at positions 1 and 3, or 1 and 4 on a phenyl ring. Suitable thiol-containing groups include, but are not limited to, —SH, —CH$_2$SH and —CH(CH$_3$)SH. In certain embodiments, the linker comprises two thiol-containing groups, and in other embodiments, the linker comprises three thiol-containing groups.

In some embodiments, the linker has a formula selected from

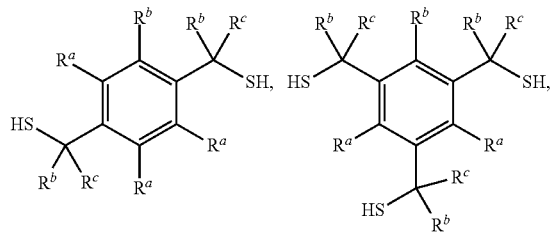

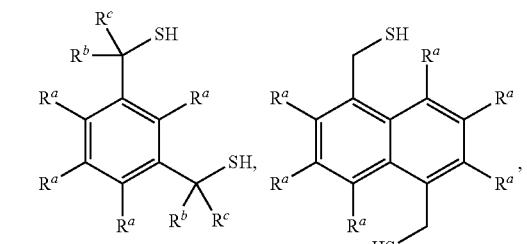

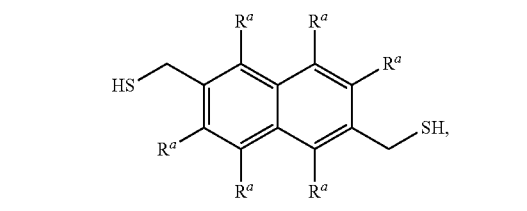

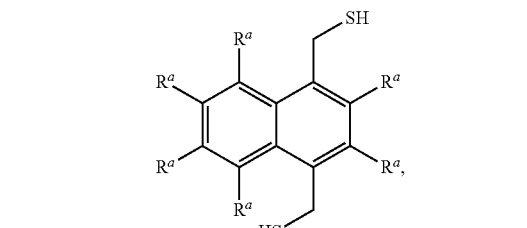

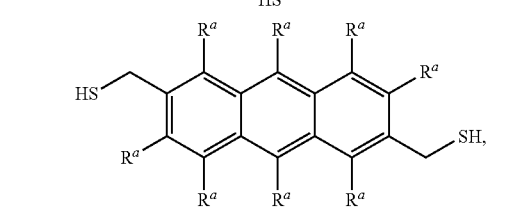

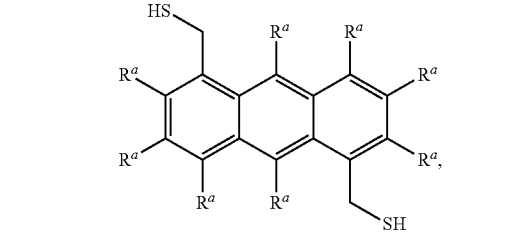

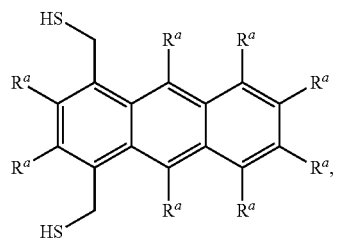

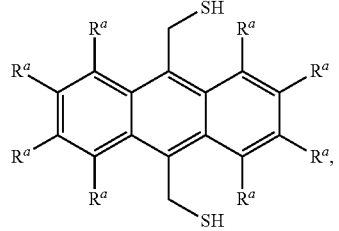

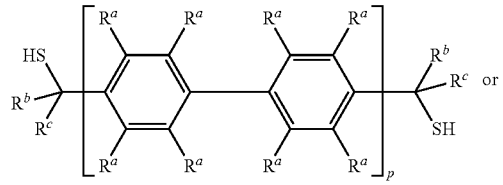

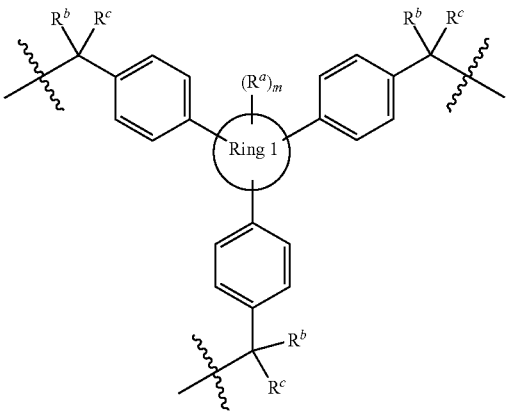

where each $R^a$ independently is hydrogen, carboxyl ester, aminocarbonyl, aliphatic, heteroaliphatic, NO$_2$, sulfonyl, amine, protected amine, aryl, heteroaryl, OH, oxo or halogen; each $R^b$ independently is hydrogen, aliphatic or heteroaliphatic; each $R^c$ independently is hydrogen, aliphatic or heteroaliphatic; p is from 1 to 4; ring 1 is aryl or heteroaryl and m is 0 to 3. In certain embodiments, at least one RC is hydrogen, and in other embodiments, at least one $R^c$ is alkyl. In particular embodiments, each $R^c$ is hydrogen or each $R^c$ is alkyl.

In some embodiments, each $R^a$ independently is hydrogen or heteroaliphatic, and in particular embodiments, each $R^a$ independently is hydrogen or alkoxy, such as methoxy.

In other embodiments, the linker is selected from

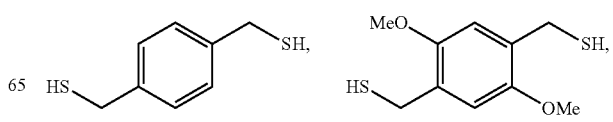

-continued

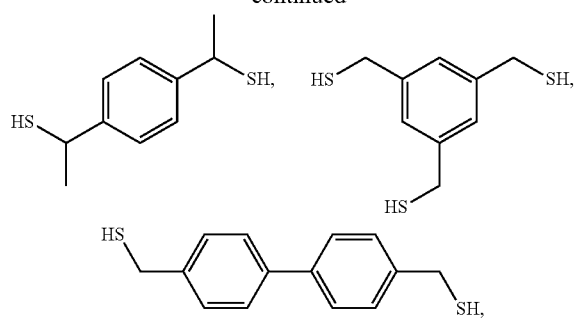

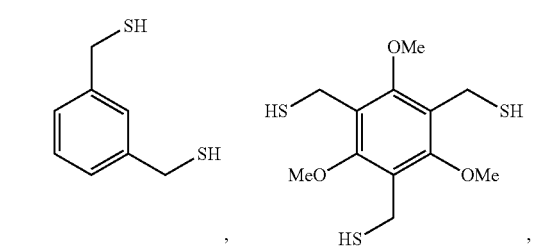

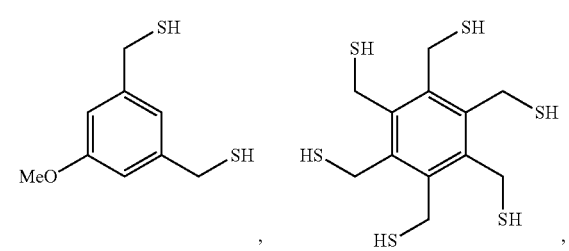

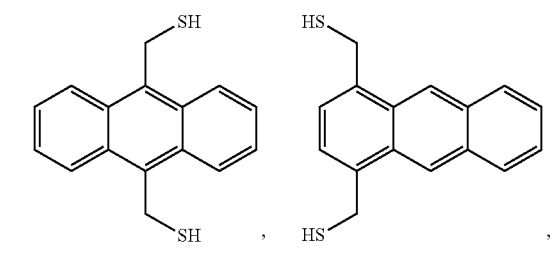

-continued

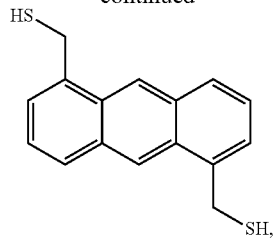

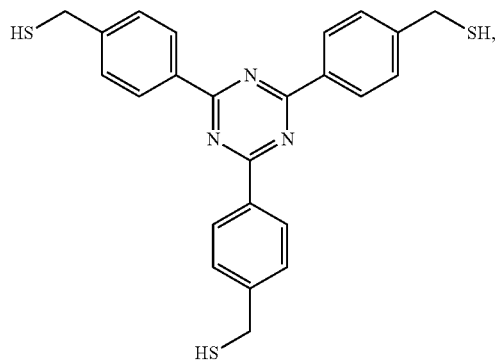

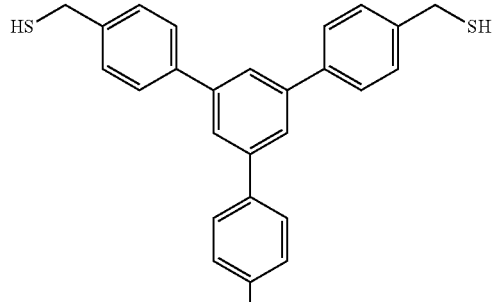

or

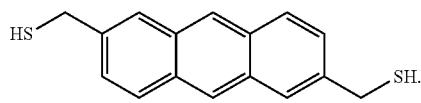

The metal salt can be any metal salt that will facilitate the reaction to form the disulfide bond. Suitable salts include, but are not limited to, triflates and halides, such as F, Cl, Br or I, and may be monohalides, dihalides, trihalides or tetrahalides. Suitable metals include, but are not limited to, transition metals and pnictogens. Exemplary metals include but are not limited to, antimony, arsenic, bismuth or zinc. In particular embodiments, the metal salt is $SbCl_3$ or $AsCl_3$. In some embodiments, a stoichiometric amount of the metal salt is used or an excess of the metal salt is used. However, in other embodiments, less than a stoichiometric amount of the metal salt is used.

The oxidant can be any oxidant that facilitates the formation of the disulfide bond. Suitable oxidants include, but are not limited to, oxygen, iodine, bicarbonate, 2,3-dichloro-5,6-dicyano-1,4-benzoquinone (DDQ) or combinations thereof.

The reaction is performed in any solvent suitable to facilitate formation of the desired disulfide cyclophane(s). Suitable solvents are typically aprotic solvents including, but not limited to, benzene, toluene, acetone, tetrahydrofuran (THF), chlorinated solvents such as dichloromethane, chloroform, tetrachlorethane, and dichloroethane, or combination thereof. Deuterated solvents are also suitable, such as $CdCl_3$, $(CD_3)_2CO$ and $C_6D_6$. In some embodiments, a certain solvent or solvent mixture is selected such that the reaction results in a desired amount of a desired cyclophane. For example, in some embodiments, a reaction performed in $CDCl_3$ results in an excess of a disulfide cyclophane trimer, over other macrocycles formed such as the dimer and tetramer, whereas a reaction performed in THF-$d_8$ gave an excess of a disulfide cyclophane tetramer, and a reaction performed in $(CD_3)_2CO$ resulted in an excess of a disulfide cyclophane dimer. Concentration may also have an effect. For example, when the linker has three thiol groups and the disulfide-forming reaction results in a mixture of tetrahedron-like compounds and dimers of the linker, low concentrations of the linker in the reaction favor the formation of the dimer, whereas higher concentrations result in a higher ratio of the tetrahedron-like structure.

In some embodiments, the desulfurization of the disulfide cyclophane to form a thiacyclophane is performed by contacting the disulfide cyclophane with a suitable phosphoramide in a suitable solvent. In some examples, the glassware used for the reaction is prepared by washing with aqua regia and then oven and/or flame dried. Suitable phosphoramides are any phosphoramides that can remove a sulfur from the disulfide bond to form a thioether, and include, but are not limited to, hexamethylphosphoramide (HMPT), and hexaethylphosphoramide (HEPT). Suitable solvents for the desulfurization include, but are not limited to, chlorinated solvents such as chloroform and dichloromethane. In some embodiments, the reaction is performed in an inert atmosphere, such as under nitrogen or argon. In some examples, after gently mixing the reagents, the desulfurization reaction left to sit without agitation, such as without stirring, swirling or shaking. The desulfurization reaction may also proceed without external heating, such as at or below the ambient temperature.

The thiacyclophanes can undergo further desulfurization to form an unsaturated hydrocarbon cyclophane. The desulfurization reaction is performed in the presence of a suitable reagent. In some embodiments, the desulfurization reaction is performed in the presence of a methylating compound and a base. Any suitable methylating agent can be used, such as, but not limited to, methyl iodide, trimethyloxonium tetrafluoroborate, dimethoxycarbonium tetrafluoroborate, dimethyl carbonate, diazomethane or combinations thereof. Suitable bases include any base that will facilitate the desulfurization reaction. Suitable bases include, but are not limited to, a hydride base such as sodium hydride or potassium hydride, a hydroxide salt such as sodium hydroxide, lithium hydroxide, potassium hydroxide or cesium hydroxide, a tertbutoxide, such as potassium tertbutoxide, or combinations thereof. The reaction is performed in a suitable solvent, such as an aprotic solvent. Suitable solvents include, but are not limited to, THF, ether, or MTBE. Treatment with the methylating agent initially forms a methylated species that can then undergo further methylation with the same methylating agent or a different methylating agent, followed by treatment with the same base, or a different base, to form the unsaturated cyclophane. Alternatively, the methylated species can be oxidized by a suitable oxidizing agent, such as bromine and bicarnonate, to form a sulfoxide compound. The sulfoxide compound is then heated such that it undergoes pyrolysis, or heated in a suitable solvent, such as N-methyl-2-pyrrolidinone, for a time effective to form the unsaturated cyclophane. An exemplary synthesis using dimethoxycarbonium tetrafluoroborate, oxidation and pyrolysis is illustrated in Scheme 1.

Scheme 1

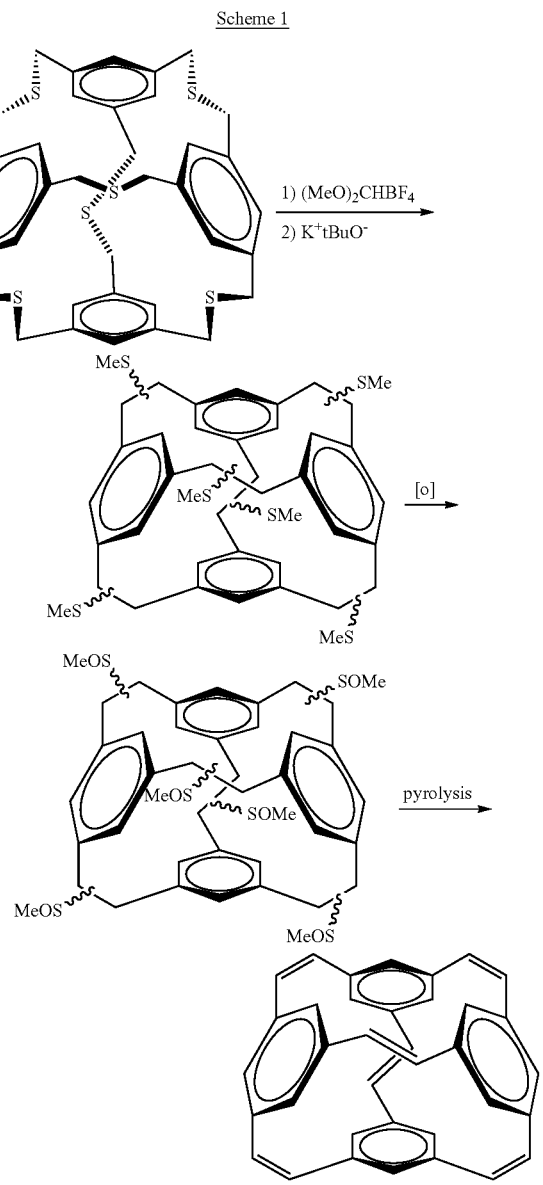

In an alternative embodiment, the thiacyclophane is reacted with n-butyl lithium in a suitable solvent, such as THF, or ether, before being reacted with a methylating agent such as methyl iodide to form a rearranged product. The rearranged product is dissolved in a dry solvent and treated with Borch reagent (($MeO)_2CHBF_4$) to form a dimethylsulfonium salt. Suitable solvents for this reaction include, but are not limited to, chlorinated solvents, such as dichloromethane and chloroform. The dimethylsulfonium salt is then reacted with a strong base, such as potassium tertbutoxide, to form the unsaturated hydrocarbon cyclophane (Scheme 2).

Scheme 2

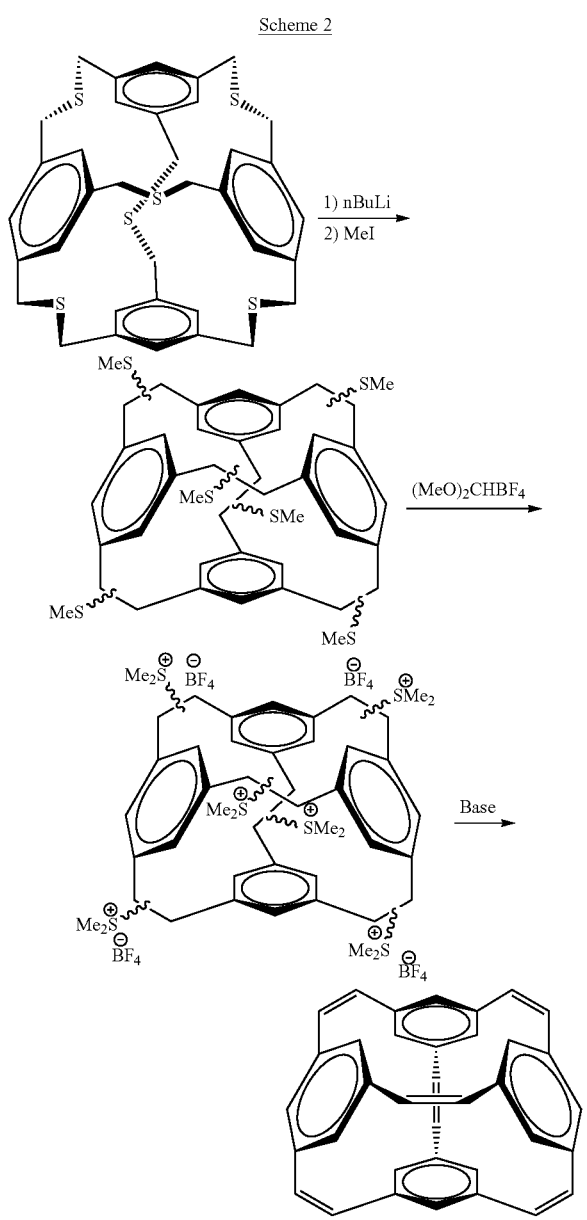

In other embodiments, the desulfurization of the thiacyclophane is performed by first oxidizing the thioether with a suitable oxidizing agent, and then exposing the oxidized cyclophane to pyrolysis to form the unsaturated cyclophane. Suitable oxidizing agents include any oxidizing agent that can oxidize the thioether to a sulfoxide or a sulfonyl (—$CH_2$—S—$CH_2$— to —$CH_2$—SO—$CH_2$— or —$CH_2$—$SO_2$—$CH_2$—), such as, but not limited to, hydrogen peroxide or m-chloroperbenzoic acid (mCPBA). Suitable solvents include any solvent that will facilitate the oxidation of the thioether moiety, such as chloroform, dichloromethane, acetic acid or combinations thereof. Alternatively, a Ramberg-Backlund-type elimination can be performed to form the unsaturated cyclophane from the oxidized cyclophane, by treating the oxidized cyclophane with a suitable base, such as a hydroxide base, in an alcohol such as tert-butanol.

Another alternative to form the unsaturated hydrocarbon cyclophane is to perform a Steven's rearrangement on the thiacyclophane, such as by treating the thiacyclophane with benzyne, the performing oxidation and pyrolysis to form the hydrocarbon cyclophane. An alternative to this approach is to perform a Pummerer rearrangement, such as by treating the thiacyclophane with an oxidizing agent such as meta-chloroperoxybenxoic acid, followed by acetic anhydride treatment and elimination. Additional information concerning these method can be found in Tetrahedron Letters 1975, No. 45: 3881-3884, and Organic and Biomolecular Chemistry, 2011, 9: 5018-5020, both of which are incorporated herein by reference.

In alternative embodiments, over-desulfurization with the phosphoramide can occur, thereby forming the hydrocarbon cyclophane directly from the disulfide cyclophane.

The unsaturated hydrocarbon cyclophanes may then be converted to a saturated hydrocarbon cyclophanes by reducing the double bond to a single bond. Reactions to reduce unsaturated hydrocarbons to for saturated hydrocarbons are well known to persons of ordinary skill in the art, and include, but are not limited to, hydrogenation in the presence of a metal catalyst such as palladium on carbon or a nickel catalyst. An alternative is to form a saturated hydrocarbon cyclophane directly from the thiacyclophane, such as by treating the thiacyclophane with Raney nickel, and optionally additional hydrogen gas, to desulfurize the thiacyclophane and form the saturated hydrocarbon cyclophane in one reaction.

IV. Applications

The well-defined topology and high strain of cyclophanes has found utility in a number of applications including asymmetric catalysis, insulating plastics, protecting barriers in chemical deposition processes, organic electronics, and host-guest chemistry and molecular recognition. For example, paracyclophane is used in the Parylene process for making a barrier coating for electronic and medical devices.

Cyclophanes are particularly useful for host-guest interactions and molecular recognition applications because the ring size and shape of the cyclophane can be easily designed to fit a desired molecule or ion. By selecting a particular linker molecule, the cyclophanes can be synthesized to accommodate the guest molecule or ion. This flexibility allows a chemist great control over the properties of the interior, hydrophobic cavity, and also over the possible binding opportunities to the aromatic rings via cation-π and polar-π interactions. The cyclophanes can also be modified to increase or decrease solubility in water and/or organic solvents as required.

The host-guest properties of cyclophanes mean that they are of interest as drug delivery systems and for separation applications. These include fluid purification, where a cyclophane is designed to remove contaminants such as organic molecules, from water or other fluids. Cyclophanes can also be used in solid-liquid extraction processes. Another potential application of the host-guest properties of cyclophanes is to remove odorants, such as in an air freshening system.

Another application of the disclosed compounds is in the synthesis of polymers, such as conjugating polymers, conducting polymers and the like. In some embodiments, the polymers are soluble polymers, such as soluble conducting polymers. An unsaturated hydrocarbon cyclophane comprising 2, 3, 4, 5, 6, 7, 8, 9, 10 or more linker units can be synthesized by the disclosed methods, and then be exposed to a ring-opening reagent or catalyst to form the polymer. In an exemplary method, an unsaturated hydrocarbon cyclophane is treated with the second generation Grubbs' catalyst ([1,3-bis-(2,4,6-trimethylphenyl)-2-imidazolidinylidene]dichloro(phenylmethylene) (tricyclohexylphosphine)ruthenium) in a suitable solvent such as THF (Scheme 3). The mixture is heated at from 40° C. to 80° C. for a sufficient time to facilitate the reaction, such as for from 3 hours to 24 hours. The reaction is then quenched, such as by adding the reaction mixture to ethyl vinyl ether.

Scheme 3

Synthesis of 1,4-dimethoxy-[4.4](2,5)-, 1,4-dimethoxy-[4.4.4](2,5)-, 1,4-dimethoxy -[4.4.4.4](2,5)-, 1,4-dimethoxy-[4.4.4.4.4](2,5)-, and 1,4-dimethoxy -[4.4.4.4.4.4](2,5)parabenzenophane ($L^2{}_2$, $L^2{}_3$, $L^2{}_4$, $L^2{}_5$, and $L^2{}_6$ respectively)

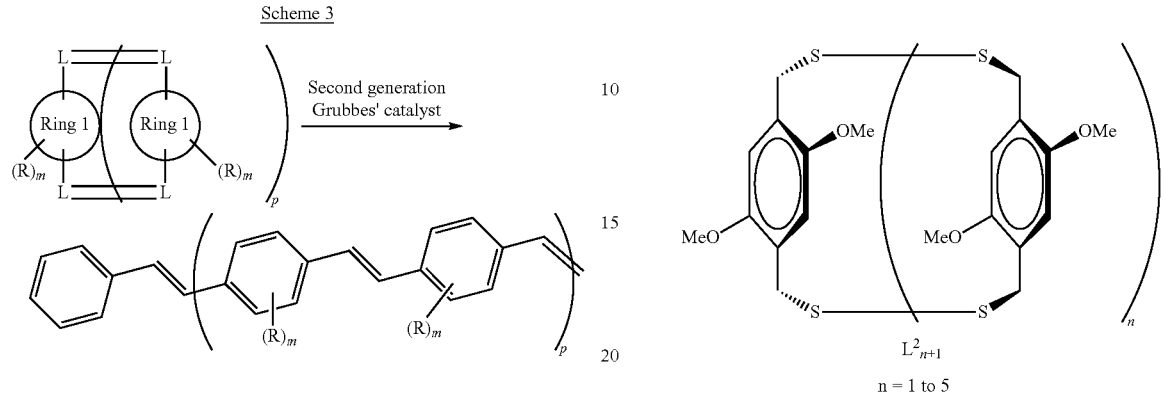

$L^2{}_{n+1}$ n = 1 to 5

V. Examples $^1$H NMR spectra were measured using Varian INOVA-300, 500, and 600 spectrometers and $^{13}$C Varian INOVA-600 spectrometer in CDCl$_3$ and TCE-d$_2$. Spectra were referenced using the residual solvent resonances as internal standards and reported in ppm. Single crystal X-ray diffraction studies were performed on a Bruker SMART10.1055/s-0030-1259306 APEX diffractometer. Commercially available reagents were used as received. The reported yields are for isolated samples. 1,4-mercaptomethyl benzene [H$_2$L$^1$], 1,4-dimethoxy-2,5-bis(mercaptomethyl)benzene [H$_2$L$^2$] and 2,3,12,13-tetrathia[4.4]parabenzenophane [L$^1{}_2$], 2,3,12,13, 22,23-hexathia[4.4]parabenzenophane [L$^1{}_3$], and 2,3,12,13, 22,23,33,34-octathia[4.4]parabenzenophane [L$^1{}_4$] were prepared by the methods of Collins, et al., Chem. Commun., 2013, 49:6599-6601.

Synthesis of 1,3,5-benzenetrimethanethiol [H$_3$L$^3$]

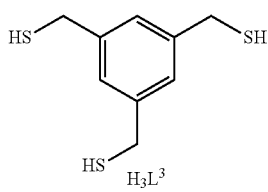 [SMILES: SCc1cc(CS)cc(CS)c1]

H$_3$L$^3$ 1,3,5-tris(bromomethyl)benzene (5.0 g, 14.01 mmol) and thiourea (6.40 g, 84.10 mmol) were dissolved in acetone (400 mL) and stirred for 16 hours at 63° C. The thiouronium salt was filtered, placed in a 1 L round bottom flask and purged with N$_2$. Degassed 3 M NaOH (250 mL) was cannulated into the flask and the solution was stirred for 4 hours at 80° C. The reaction mixture was removed from heat and degassed 9 M HCl (200 mL) was cannulated into the flask alternating with degassed CHCl$_3$ (150 mL) until pH 2 was achieved. Product was extracted three times with CHCl$_3$ and the combined extracts were washed with brine. The solution was dried with Na$_2$SO$_4$, and filtered. The filtrate was concentrated to give a yellow oil (84%). $^1$H NMR (300 MHz, CDCl$_3$): δ 7.17 (s, 6H, C$_6$H$_3$), 3.73 (d, 6H, CH$_2$, J=7.6 Hz), 1.79 (t, 3H, SH, J=7.6 Hz)

Under an atmosphere of ambient air, [H$_2$L$^2$] (25 mg, 0.110 mmol) was added to CHCl$_3$ (25 mL) in a flask equipped with a stir bar. A second flask was charged with I$_2$ (56 mg, 0.221 mmol) and SbCl$_3$ (13 mg, 0.055 mmol) in 25 mL CHCl$_3$. The solution of I$_2$ and SbCl$_3$ was then added slowly to the solution of H$_2$L$^2$ while stirring. The dark purple solution was then allowed to stir at ambient temperature for 16 hours. The desired disulfide complexes were obtained by quenching with sodium sulfite followed with washing the chloroform mixture with deionized water (2×). The solution was dried with Na$_2$SO$_4$, filtered and concentrated under reduced pressure to afford a white powder. The powder was then redissolved in 3 mL of chloroform and purified by GPC (93% isolated yield: 37% dimer; 35% trimer, 13% tetramer, 4% pentamer, 4% hexamer).

$^1$H NMR (CDCl$_3$):

$L^2{}_2$: δ=6.422 (bs, 4H, C$_6$H$_2$), 3.758 (s, 12H, CH$_3$), 3.849 (bs, 4H, CH$_2$), 3.279 (bs, 4H, CH$_2$);

$L^2{}_3$: δ=6.527 (s, 6H, C$_6$H$_2$), 3.775 (s, 18H, CH$_3$), 3.586 (s, 12H, CH$_2$);

$L^2{}_4$: δ=6.647 (s, 8H, C$_6$H$_2$), 3.758 (s, 24H, CH$_3$), 3.623 (s, 16H, CH$_2$);

$L^2{}_5$: δ=6.641 (s, 10H, C$_6$H$_2$), 3.754 (s, 30H, CH$_3$), 3.646 (s, 20H, CH$_2$);

$L^2{}_6$: δ=6.657 (s, 12H, C$_6$H$_2$), 3.758 (s, 36H, CH$_3$), 3.677 (s, 24H, CH$_2$).

Synthesis of disulfide [4.4.4.4.4.4](1.3.5) and [4.4.4](1.3.5) cyclophane (L$^3{}_4$ and L$^3{}_2$)

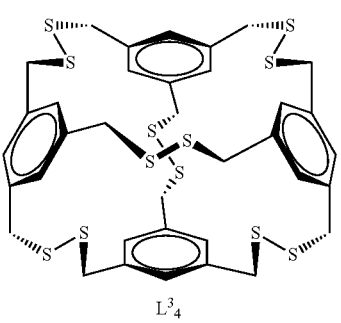

L$^3{}_4$

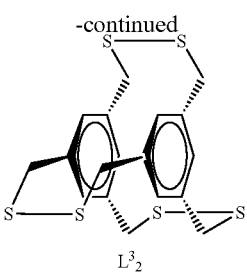

L³₂

Under an atmosphere of ambient air, [H₃L³] (90 mg, 0.416 mmol) was added to CHCl₃ (100 mL) in a flask equipped with a stir bar. A second flask was charged with $I_2$ (317 mg, 1.248 mmol) and $SbCl_3$ (237 mg, 1.040 mmol) in 100 mL CHCl₃. The solution of $I_2$ and $SbCl_3$ was then added slowly to the solution of H₃L³ while stirring. The resulting mixture was then allowed to stir at ambient temperature for 16 hours to afford a clear, dark purple solution. The desired disulfide complexes were obtained by quenching with sodium sulfite followed with washing the chloroform mixture with deionized water (2×). The solution was dried with $Na_2SO_4$, filtered and concentrated under reduced pressure to afford a white powder. The powder was then redissolved in 3 mL of chloroform and purified by GPC (98.5% isolated yield: 69.5% dimer; 28.99% tetrahedron).

L³₄ ¹H NMR (600 MHz, CDCl₃): δ=6.968 (s, 12H, C₆H₃) 3.621 (s, 24H, CH₂); ¹³C{¹H} NMR (150 MHz, CDCl₃): δ=138.666, 129.082, 44.860 ppm;

L³₂ ¹H NMR (600 MHz, CDCl₃): δ=6.806 (s, 6H, C₆H₃), 3.644 (s, 12H, CH₂). ¹³C{¹H} NMR (150 MHz, CDCl₃): δ=138.663, 128.993, 43.686 ppm.

Synthesis of trithia[3.3.3]-paracyclophane (1)

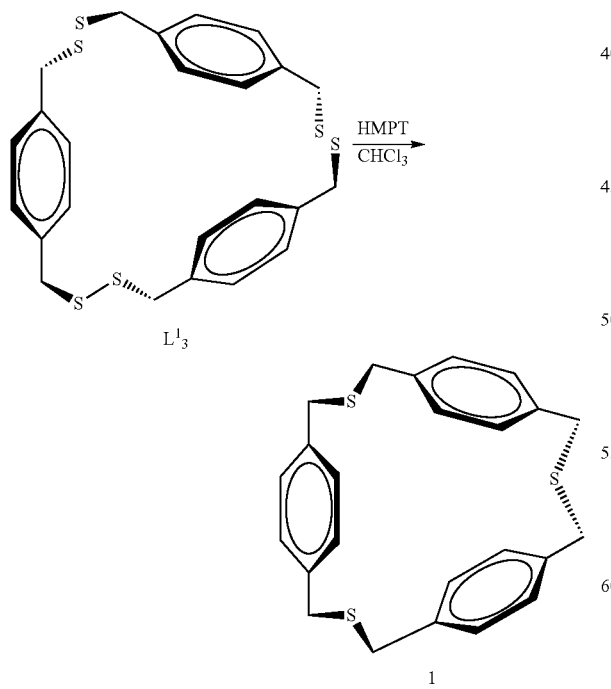

A 100 mL round bottom flask was charged with [L¹₃] (9.17 mg, 0.018 mmol) in 16 mL chloroform dried with 4 Å molecular sieves. The solution was degassed with nitrogen for 1 hour. Under a cone of nitrogen, HMPT (9.90 μL, 0.054 mmol) was added to the flask and the solution was gently swirled to mix. The reaction was allowed to sit under N₂ at ambient temperature for 16 hours. The flask was removed from the nitrogen line and an additional 3 equivalents of HMPT (9.90 μL, 0.054 mmol) was added to the flask, and the solution was left unmoved and without agitation for 5 days. The solution was then concentrated down giving a pearlescent, white solid showing 100% conversion to 1 by ¹H NMR. The solid was redissolved in chloroform and washed with deionized water and brine then concentrated down. To remove HMPA, the solid was sonicated with deionized water, extracted with dichloromethane and passed through a silica plug (70% isolated yield). ¹H NMR (300 MHz, CDCl₃) of (1):67 =6.844 (s, 6H, C₆H₄) 3.621 (s, 12H, CH₂); ¹³C{¹H} NMR (150 MHz, CDCl₃): δ=138.667, 129.083, 44.859 ppm. FIG. 1 provides a single crystal X-ray structure representation of 1.

Synthesis of 1,4-methoxy-trithia [3.3.3]-paracyclophane (2)

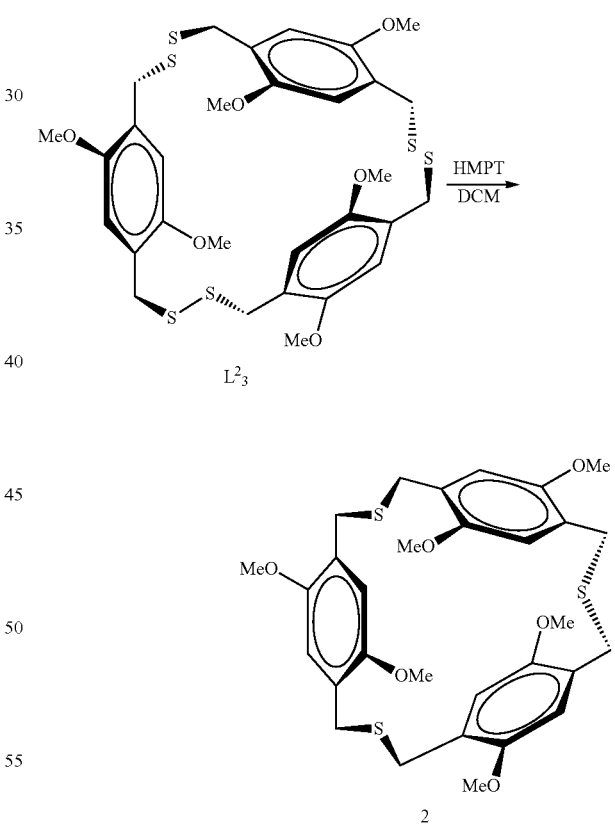

[L²₃] (12.61 mg, 0.018 mmol) was dissolved in 1 mL of CD₂Cl₂ and transferred to an oven-dried NMR tube. HMPT (13.40 μL, 0.074 mmol) was added to the NMR tube, and the tube was shaken vigorously. Reaction is observed to be complete in 4 hours by ¹H NMR giving the desired thioether trimer (2) (72% isolated yield after centrifuge purification). ¹H NMR (300 MHz, CD₂Cl₂): δ=6.523 (s, 6H, C₆H₂), 3.685 (s, 12H, CH₂), 3.506 (s, 18H, CH₃).

Synthesis of 2,11,20-trithia[3.3.3](1,3,5) cyclophane (3)

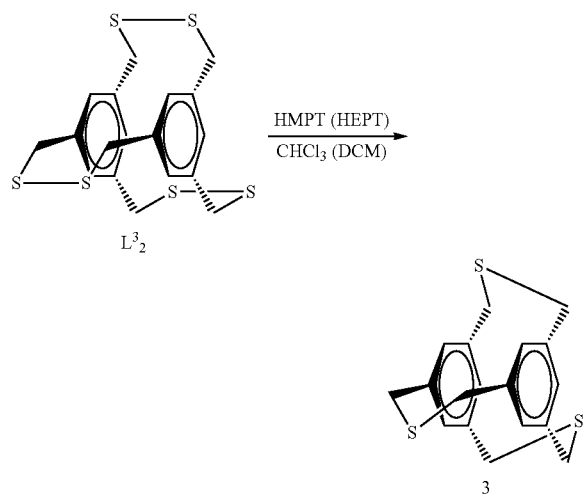

[L³₂] (4.70 mg, 0.011 mmol) was dissolved in 1 mL of degassed CDCl₃ (4A molecular sieve dried) and transferred to an oven-dried NMR tube. HMPT (7.19 µL, 0.441 mmol) was added to the NMR tube, and the tube was shaken vigorously. Reaction is observed to be complete in two hours by ¹H NMR at 100% conversion to desired thiacyclophane dimer 3 (92% isolated yield after centrifuge purification). ¹H NMR (600 MHz, CDCl₃): δ=6.9 (s, 6H, C₆H₃), 3.83 (s, 12H, CH₂).

Synthesis of [3.3.3](1,3,5) thiatetrahedrophane (5)

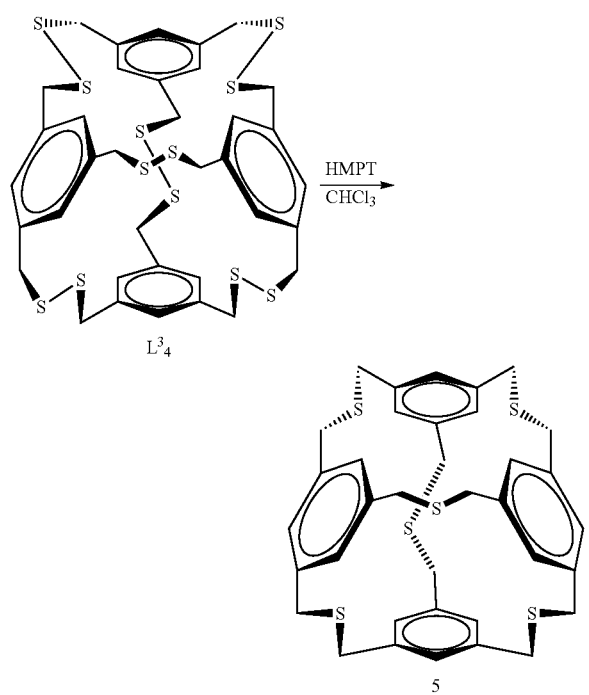

10 mL of CDCl₃ dried under 4 Å molecular sieves was added to [L³₄] (22 mg, 0.026 mmol) in an acid-washed, oven-dried glass vial. The vial was sonicated until the solution was evenly dispersed as a cloudy white mixture. HMPT (28 µL, 0.155 mmol) was added to the vial in which the solution alters from cloudy in appearance to clear and colorless within 15 minutes. The reaction was left unmoved and without agitation at ambient temperature for 16 hours then concentrated down. In a separate synthesis with a 4.55 mM solution, the reaction was left for 4 hours without agitation. The white solid was sonicated with deionized water and then transferred to a centrifuge tube. To remove any remaining HMPA, the product was washed 3× with deionized water by centrifugation: the solid was dispersed in water and centrifuged down. The aqueous supernatant was pipetted off the product pellet. This centrifugation wash was repeated two more times to thoroughly remove any residual water-soluble HMPA. The white solid was then dissolved in chloroform, dried with Na₂SO₄ and concentrated to give the final crystalline solid (94.5% isolated yield). (500 MHz, CDCl₃): δ=6.830 (s, 12H, C₆H₃), 3.487 (s, 24H, CH₂). ¹³C{¹H} NMR (125 MHz, CDCl₃): δ=138.151, 127.752, 36.808 ppm.

Synthesis of [2.2.21](1,3,5) tetrahedrophane-hexa-ene (Scheme 2)

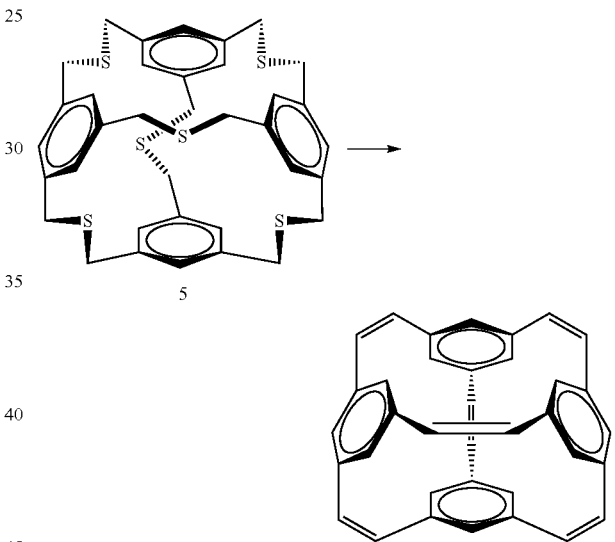

2 mL of 5 (15.8 mg, 0.024 mmol) in dry tetrahydrofuran (THF) was added dropwise to a solution of n-butyllithium (0.155 mmol) in 1 mL dry THF while stirring in a salt ice bath. The dark reddish purple solution stirred under nitrogen until the ice had melted (about 2 hours) and was then treated with 0.5 mL of non-dried THF. On a new ice bath, methyl iodide (9.07 µL, 0.156 mmol) was added slowly and stirred for an additional ten minutes. The reaction mixture was quenched with 0.5 mL of deionized water, poured into 5 mL of water and the product was extracted with chloroform. The organic extract was dried with Na₂SO₄, filtered, concentrated and dried in vacuo overnight to give a rearranged product that was used without further purification. (40% yield).

To the vial of crude rearranged product, the substrate (6.78 mg, 0.009 mmol) was dissolved in 1 mL of dry dichloromethane (DCM) and transferred to oven-dried glass vial with stir bar. Borch reagent ((MeO)₂CHBF₄) (0.05 mL) was added dropwise over ten minutes with cooling in ice, and the reaction was stirred under nitrogen for six hours, resulting in a dark red precipitate forming. The reaction mixture was then concentrated down and mixed with 2.5 mL of ethyl acetate, stirred overnight and then dried in vacuo giving the dimethyl sulfonium salt as a brown oil.

The dimethyl sulfonium salt was then re-dissolved in 2 mL of dry THF and added dropwise to a solution of potassium tert-butoxide (12 equivalents) in 1 mL dry THF on an ice bath. The solution rapidly turned from brown to yellow. The reaction was quenched with saturated NH$_4$Cl (0.3 mL) after 16 hours and poured into a separatory funnel. The mixture was extracted three times with chloroform, the chloroform fractions combined and washed with H$_2$O and brine. The solution was then dried with Na$_2$SO$_4$, filtered and concentrated to give the unsaturated hydrocarbon cyclophane.

Synthesis of trisulfone[3.3.3]-paracyclophane

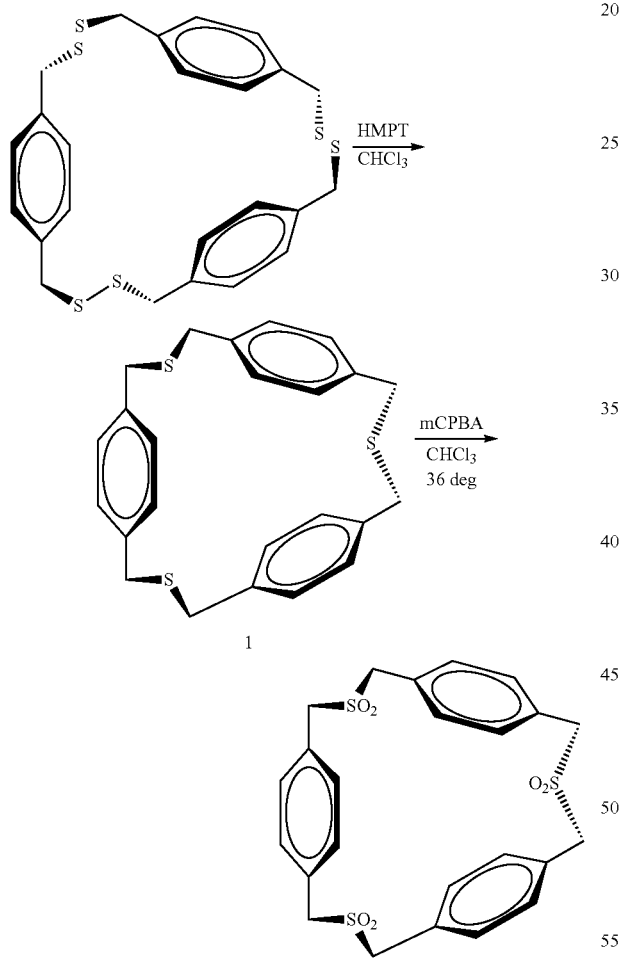

Figure 2:
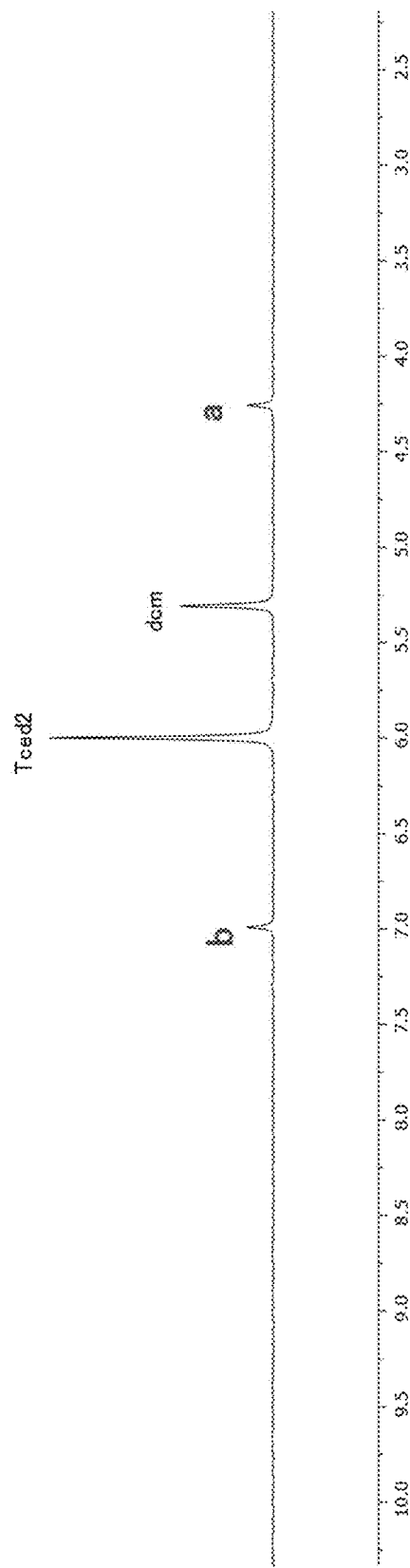
FIG. 2 is a proton NMR spectrum of trisulfone[3.3.3]-paracyclophane.

To a 20 mL oven-dried vial of 1 (9.17 mg, 0.018 mmol) in 3 mL dry chloroform, mcPBA (9.90 μL, 0.054 mmol) was quickly added and the solution was stirred under nitrogen at 36° C. for 16 hours. Reaction became cloudy within ten minutes of stirring. The solid precipitate was filtered and dried as a fine, white powder (56% isolated yield). $^1$H NMR (300 MHz, CDCl$_3$): δ=6.992 (s, 12H, C$_6$H$_4$) 4.258 (s, 12H, CH$_2$). FIG. 2 provides a $^1$H NMR spectra. With respect to FIG. 2, peak 'a' represents the methylene protons, and peak 'b' is the aromatic protons. The other two peaks are solvent peaks, from dichloromethane (dcm) and tetrachloroethane (Tced2).

Results and Discussion

Recently it was demonstrated that the self-assembly of pnictogen thiolate structures promoted the rapid synthesis of discrete disulfide complexes over the formation of insoluble oligomers when oxidized with iodine (Scheme 4). By exploitation of disulfides' dynamic covalent behavior, the role of an external additive (e.g. SbCl$_3$) has now been discovered to be more relevant than initially surmised. The directing behavior of SbCl$_3$ exhibited impressive resistance to insoluble polymer formation, long reaction times, and low selectivity for different ligand systems. Using this method of self-assembly, the acquisition of previously unattainable disulfide cyclophanes are now possible including trimers, tetramers, pentamers, hexamers and tetrahedra. From the cyclic disulfide, facile desulfurization with a phosphoramide provided a direct route to thiacyclophanes. This method offered an efficient, high yielding alternative to traditional, non-selective approaches to heterocyclophane synthesis. Herein are disclosed applications of the new methodology to the synthesis of both known and entirely new cyclophanes.

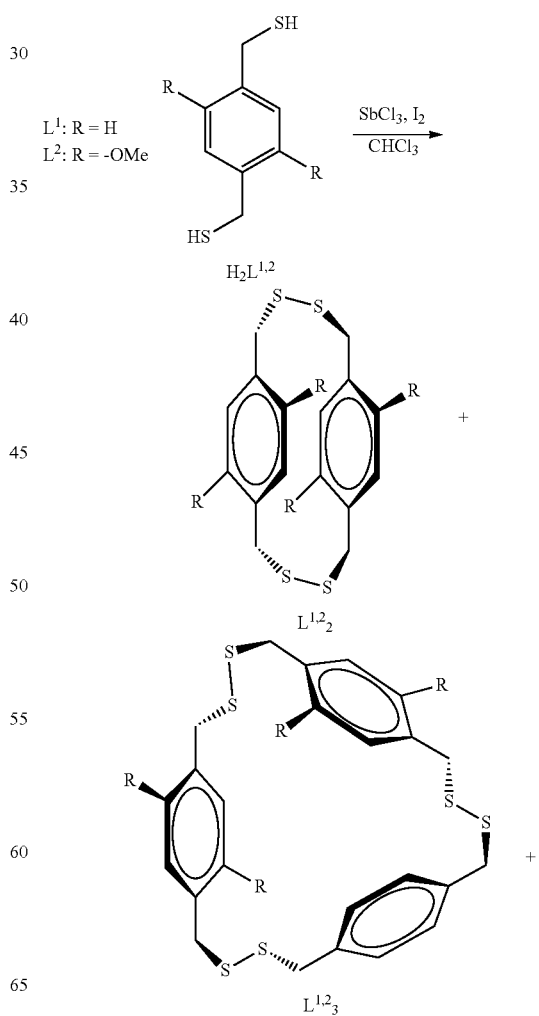

Scheme 4

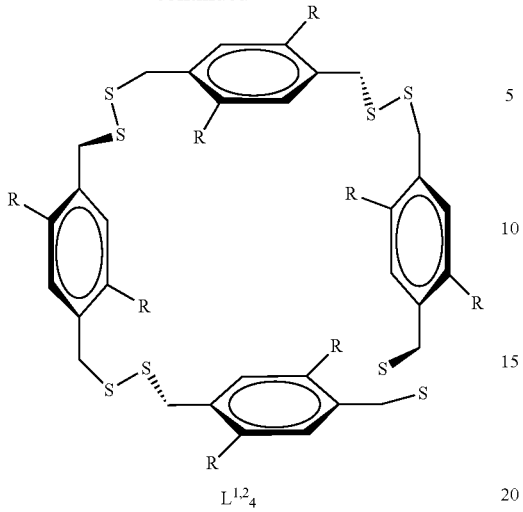

$L^{1,2}{}_4$

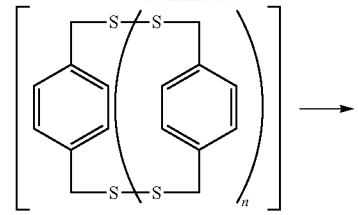

n = 1 [$L^2{}_2$]
n = 2 [$L^2{}_3$]
n = 3 [$L^2{}_4$]

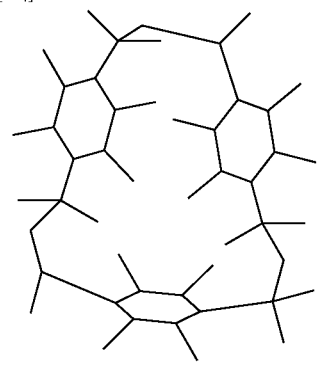

Previously, the self-assembly of disulfide macrocycles had primarily been used to form kinetic dimers or complexes which required guest inclusion. Using benzylic thiols and a catalyst, such as a pnictogen catalyst, a number of macrocyclic structures have been cleanly synthesized. Sulfur extrusion with stoichiometric phosphoramide led to the more stable oligothioether rings. This reaction appeared to be general and occurred in high yield. As an example, the known 2,11,20-trithia[3.3.3](1,3,5)cyclophane 3 was prepared by exposing tridisulfide [4.4.4](1,3,5)cyclophane [$L^3{}_2$] to a stoichiometric amount of hexamethylphosphoramide, HMPT (or hexaethylphosphoramide, HEPT), for 1.5 hours at 25° C. in quantitative yield (see synthesis, above). Over two steps, this gave a yield of 92%, a vast improvement over the previously reported 5.3% yield by condensation of 1,3,5-tris(bromomethyl)benzene with 1,3,5-tris(mercaptomethyl)benzene [$H_3L^3$]. Surprisingly, no evidence of ring opening products was observed. Without being bound to a particular theory, a mechanism for this reaction was proposed to occur through an ion paired thiophosphonium and free thiolate formed by nucleophilic attack of the phosphoramide. In the case of these larger structures, the more activated HMPT was required to prevent polymerization. This was likely due to the speed of the reaction of free thiolate recombining to eliminate a neutral thiophosphoramide. In addition to a stepwise approach where the disulfide was purified first, a one-pot reaction was also successful (Scheme 5), and by using [$H_3L^3$], SbCl$_3$, I$_2$ and phosphoramide thiacyclophane 3 was formed by the one pot method, as seen by 1H-NMR spectroscopy.

Scheme 5

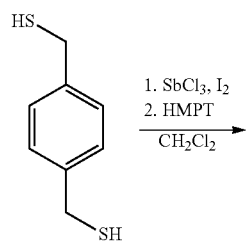

1. SbCl$_3$, I$_2$
2. HMPT
CH$_2$Cl$_2$

Figure 3:
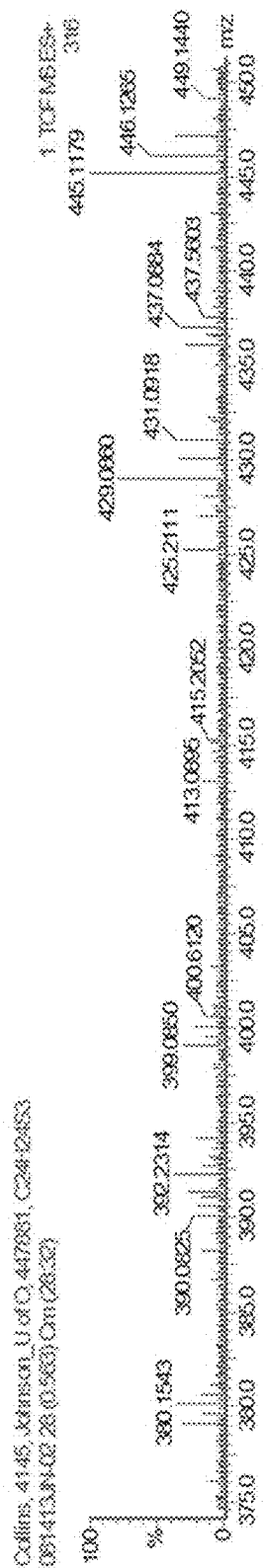
FIG. 3 is a mass spectrum of trithia[3.3.3]-paracyclophane.
Figure 4:
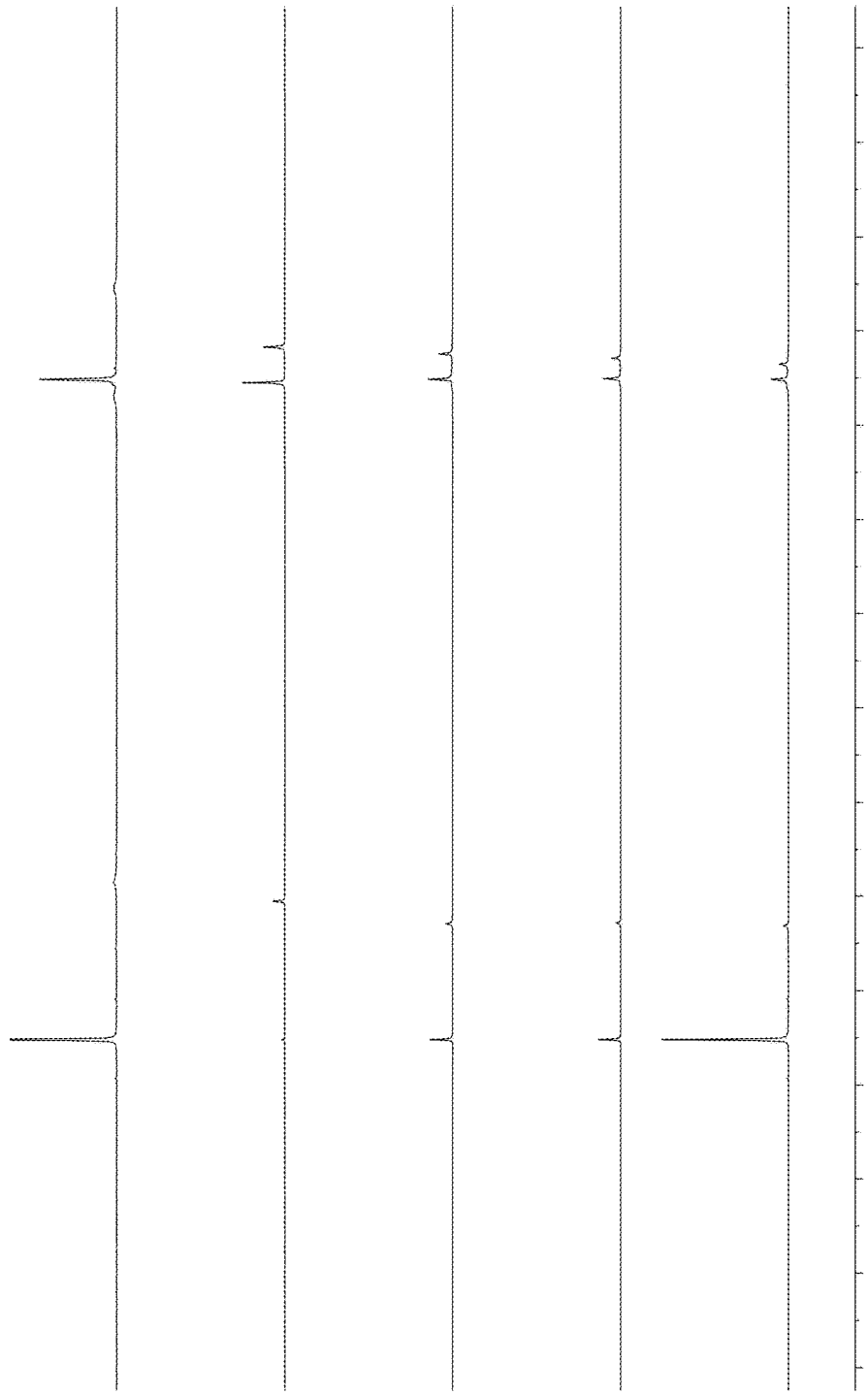
FIG. 4 is a diagram providing stacked NMR spectra of $[L^2{}_2]$ (top), $[L^2{}_3]$, $[L^2{}_4]$, $[L^2{}_5]$, and $[L^2{}_6]$ (bottom).

Following the successful synthesis of 3, a previously synthetically-inaccessible thiacyclophane was constructed, where the lack of selectivity of the classical coupling methods had previously prevented its formation. From [$L^1{}_3$], the desulfurization with HMPT in chloroform gave 1 at 100% conversion by 1H-NMR after 6 days. The desulfurization of the unsubstituted trithiaparacyclophane 1 exhibited slower product conversion than 3, and would not go to completion in dichloromethane or in the presence of a weaker phosphine, HEPT. The crude product, an iridescent white solid, was purified by trituration with water to remove any residual phosphine oxide and separated using centrifugation. This purification method was found to give the highest isolated yield serving as an optimal protocol over separatory funnel extraction or chromatography. Crystals suitable for x-ray diffraction were grown by vapor diffusion of pentanes in chloroform or slow evaporation. Mirroring the trisubstituted ligand one-pot reaction, a mixture of [$H_3L^1$], SbCl$_3$, I$_2$ and phosphoramide gave 1, as evidenced by a crude 1H-NMR and mass spectrometry (FIG. 3). In the interest of developing a functional group-tolerant cyclophane procedure, the 1,4-dimethoxy-2,5-bis(mercaptomethyl)benzene ligand [$H_3L^2$] served as an ideal precursor since demethylation in many host molecules (for example, calixarene) is customary. Iodine oxidation using SbCl$_3$ similarly underwent selective oxidation to [$L^2{}_2$] (dimer), [$L^2{}_3$] (trimer), [$L^2{}_4$] (tetramer), [$L^2{}_5$] (pentamer) and [$L^2{}_6$] (hexamer) in a combined 93% isolated yield (Scheme 4—pentamer and hexamer not shown). The spectral data of the structures, confirmed by 1H-NMR, were simple, indicating high symmetry of molecules (FIG. 4). The aromatic protons exhibited an upfield shift as the macrocycle decreased in size due to shielding effects by benzene rings that were in face-to-face relation. This ligand system was permissive toward higher concentrations and a wider variety of organic solvents due to the enhanced solubility of the methoxy functional groups in solution. Unlike the unsubstituted adducts, the formation of higher ordered [$L^2$] disulfide-based cyclophanes (i.e. tetramer, pentamer, hexamer, etc.)

required longer reaction times. The conversion to larger cyclic disulfides increased after 16-24 hours at ambient temperature. Additionally, this slow conversion to higher ordered cyclophanes like trimers, tetramers, pentamers and hexamers was mediated by the amount of $SbCl_3$, concentration, and/or choice of solvent. The thioether 2 was prepared by desulfurization of $[L^2{}_3]$ with HMPT in 4 hours in dichloromethane or 2 hours in chloroform.

Thiatetrahedrophane

The preparation of highly bridged cyclophanes has previously suffered from lengthy and tedious syntheses requiring stepwise modification and addition of each bridge. Larger capsule-like molecules with similar structural features such as cubes and tetrahedra have been synthesized. However, being limited synthetically stands as the largest obstacle to the ability to fully investigate the properties of these complex, highly strained systems.

Figure 5:
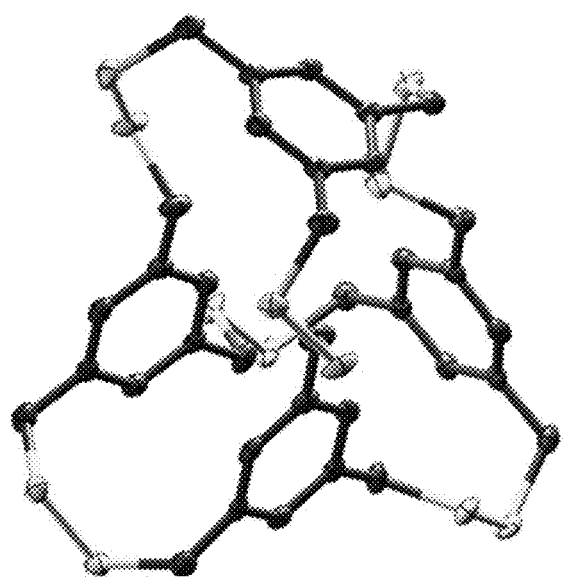
FIG. 5 a single crystal X-ray structure representation of tetrahedron $[L^3{}_4]$.

Using a self-assembly strategy, multi-substituted ligands were employed to allow the synthesis of higher ordered structures like tetrahedra. Pnictogen-activated oxidation of a trisubstituted thiol ligand $[H_3L^3]$ with iodine gave a clean distribution of disulfide dimer $[L^3{}_2]$ and a distorted tetrahedron $[L^3{}_4]$ in a combined isolated 98.5% yield after purification (Scheme 6). FIG. 5 shows the single crystal X-ray structure representation of tetrahedron $[L^3{}_4]$, with the hydrogen atoms and solvents of crystallization omitted for clarity.

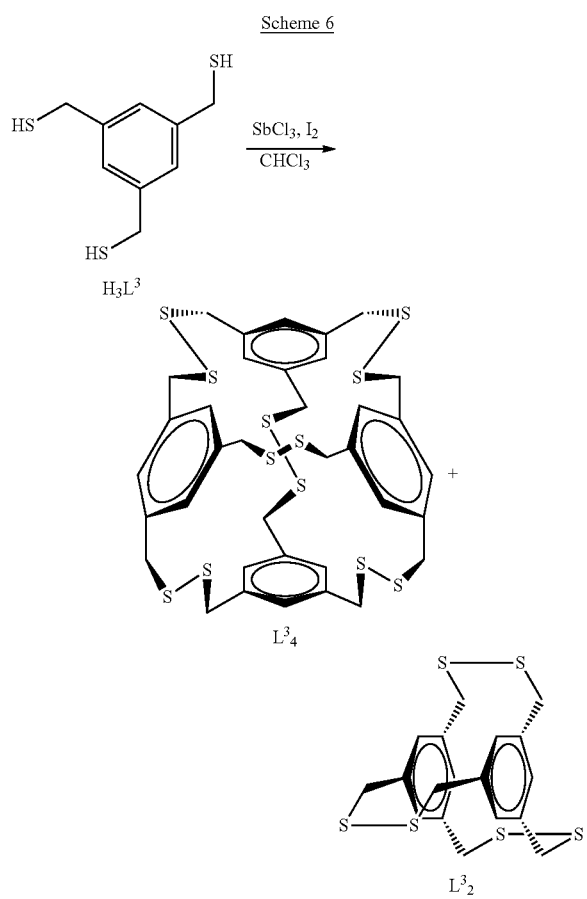

Scheme 6

Figure 6:
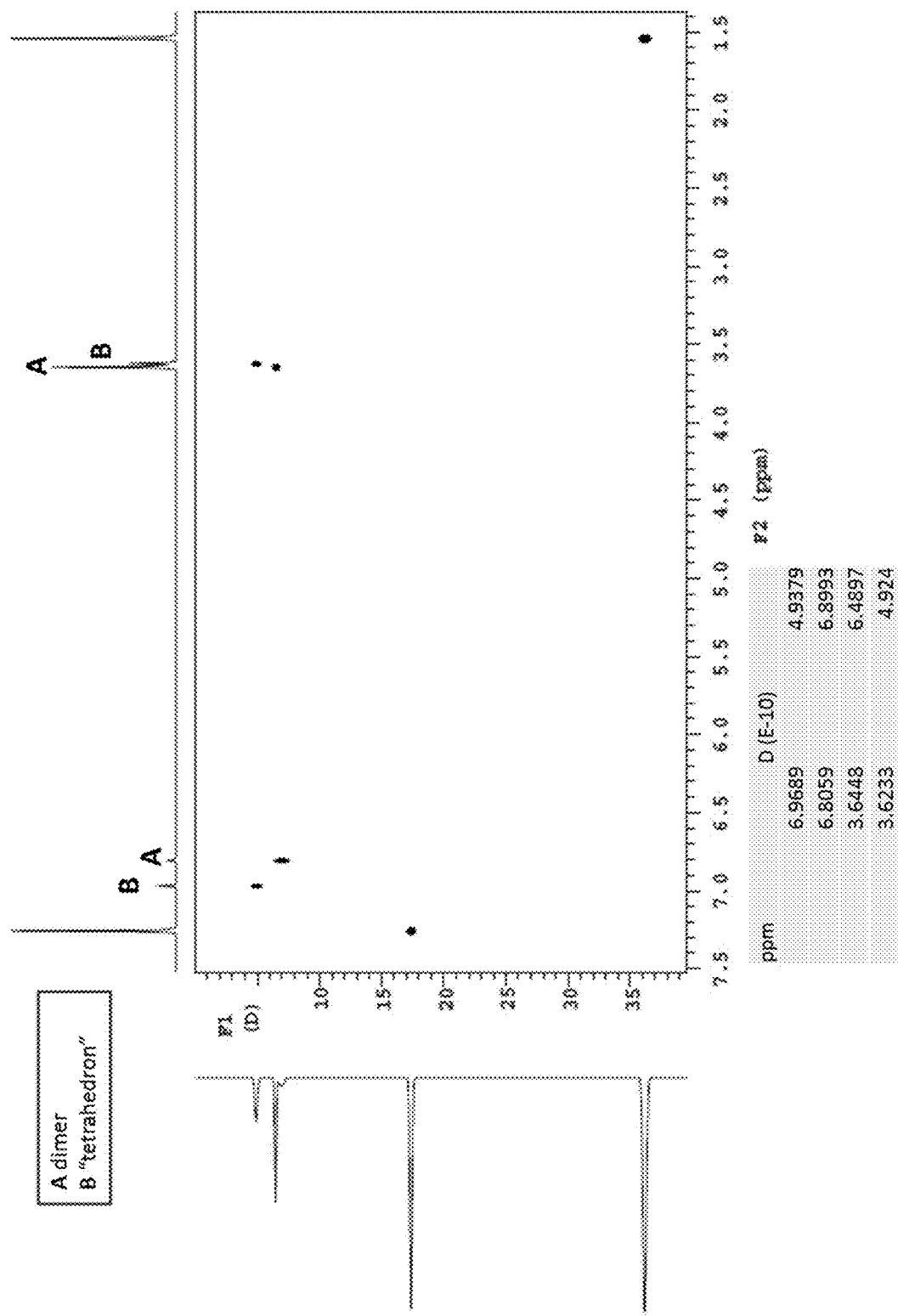
FIG. 6 is a Diffusion-Ordered Spectroscopy (DOSY) NMR spectrum of a crude reaction mixture of $[L^3{}_2]$ (A; dimer) and $[L^3{}_4]$ (B; tetrahedron) in a crude reaction mixture in $CDCl_3$.

These species were initially evidenced by diffusion-ordered NMR spectroscopy where the diffusion coefficients for the dimer and tetrahedron differ: dimer diffuses faster at 6.69e-10 m²/s versus tetramer at 4.93e-10 m²/s (FIG. 6).

Control reactions using only iodine and $H_3L^3$ revealed the pnictogen is required for selective conversion to $L^3$ disulfide complexes without sluggish reaction times. In addition, the presence of $SbCl_3$ influences the $[L^3{}_2]:[L^3{}_4]$ ratio altering it from 1:1 to 2:3 by adding 6 equivalents of $SbCl_3$ to a 2 mM control solution. Similar to many supramolecular systems, the solvent choice and the concentration of its components regulated the formation of the individual cyclic disulfides. Oxidation of the tri-substituted thiol gave a lowered isolated yield of disulfide cyclophanes when performed in dichloromethane, such that oligomeric sulfonyl iodide transition intermediates precipitated out of solution before the conversion to product was complete. When performed in chloroform, no precipitation was observed due its ability to solubilize or perhaps template any charged or metal-coordinated transition intermediates. These solvent effects were prominent in the oxidation of disubstituted ligand $[L^1]$ as well (Scheme 4). When the pnictogen-assisted iodine oxidation was performed in acetone, dimer formation was favored over trimer and trimer was favored over tetramer. In tetrahydrofuran, the dimer:trimer:tetramer ratio was in reverse relative to acetone (Table 1), suggesting THF facilitated the conversion to higher ordered structures, unlike acetone.

TABLE 1

Distribution of discrete disulfide macrocycles by oxidation of $[H_2L^1]$ performed at 2 mM concentration (6 equivalents $I_2$, ⅔ equivalents pnictogen trichloride)

| Solvent | Dimer | Trimer | Tetramer |
|---|---|---|---|
| $CDCl_3$ | 18 | 64 | 18 |
| $TCE-d_2$ | 19 | 66 | 15 |
| $C_6D_6$ | 18 | 64 | 18 |
| Toluene-$d_8$ | 32 | 53 | 15 |
| $THF-d_8$ | 8 | 35 | 57 |
| $(CD_3)_2CO$ | 61 | 30 | 9 |

Figure 7:
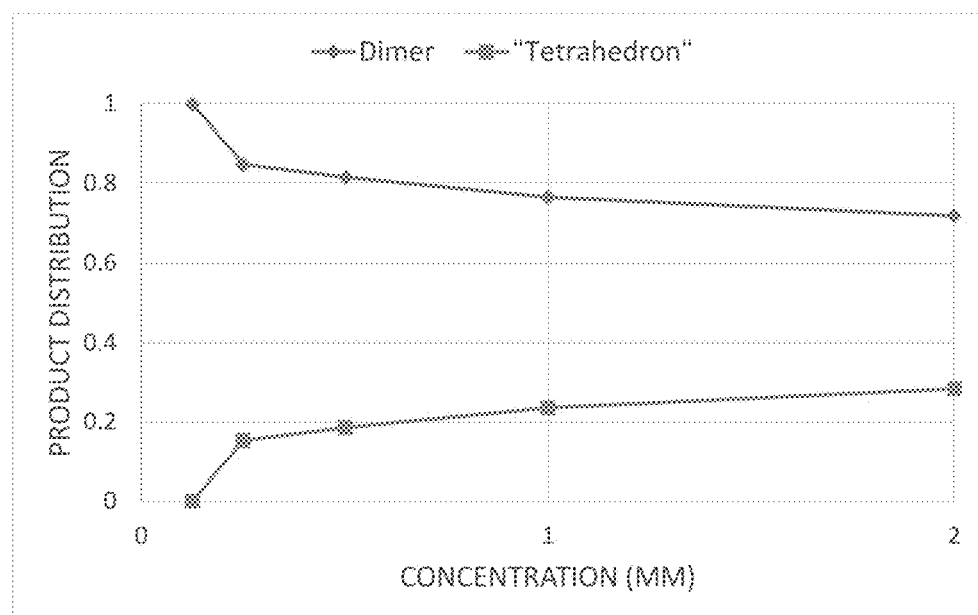
FIG. 7 is a graph of product distribution versus concentration, illustrating the product distribution of $[L^3{}_2]$ dimer and $[L^3{}_4]$ tetrahedron as a function of starting dithiol concentration, with each reaction run in $CDCl_3$ with stoichiometric amounts of antimony trichloride and iodine.

In addition to solvent interactions, formation the larger species (tetrahedron) was enhanced with longer reaction times resulting in superior yields. Likewise, increasing the equivalents of $SbCl_3$ appeared to show analogous results. The selectivity at low concentration showed $[L^3{}_2]$ formed preferentially whereas at high concentration $[L^3{}_4]$ tetrahedron was the dominant product species. This suggested that intramolecular disulfide formation was disfavored relative to the formation of $[L^3{}_4]$ (FIG. 7). The scope and limitations of the activating behavior of $SbCl_3$ and reaction conditions are currently being investigated.

Figure 8:
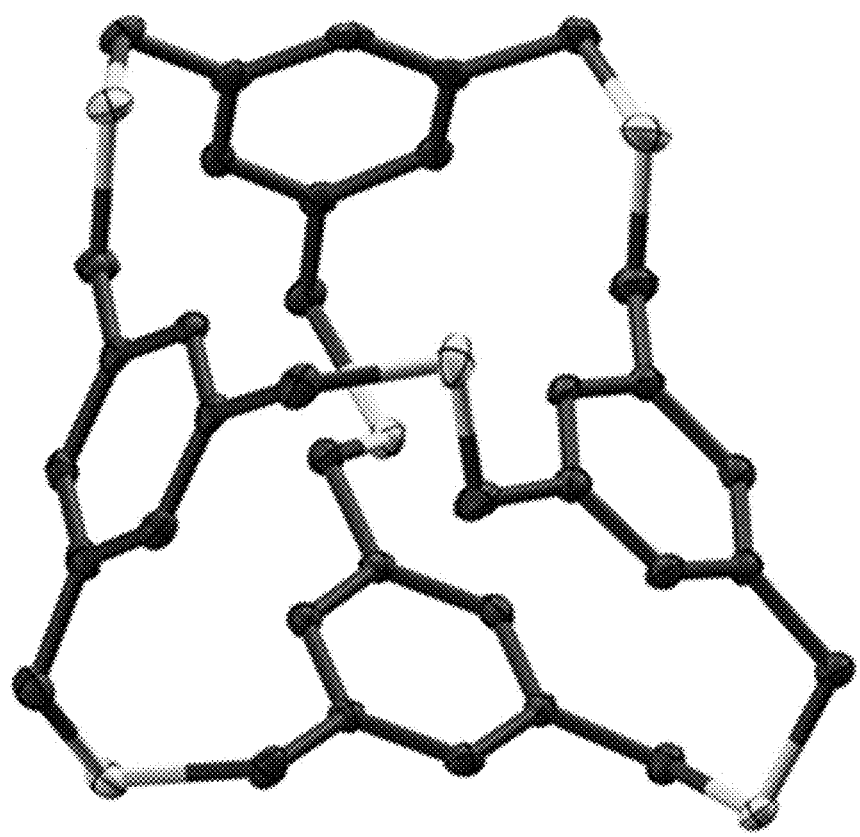
FIG. 8 is a single crystal X-ray structure representation of thiatetrahedrophane 5.

The thiatetrahedrophane 5 proceeded by desulfurization with a phosphoramide at ambient temperature in 1 hour (Scheme 7). The molecule was confirmed by spectral data via 1H-NMR, exhibiting time-averaged tetrahedral symmetry. The loss of a sulfur atom decreased the size of the cyclic structure only slightly and the aromatic and methylene singlets displayed a small, yet expected upfield shift relative to its disulfide analog in $CDCl_3$. Diffraction grade crystals were grown by vapor diffusion of pentanes into chloroform or solvent evaporation. Both $[L^3{}_4]$ and 5 capsules exhibited robust chemical stability and did not show decomposition over time or with exposure to light and silica gel. FIG. 8 provides a single crystal X-ray structure representation of thiatetrahedrophane 5.

Scheme 7

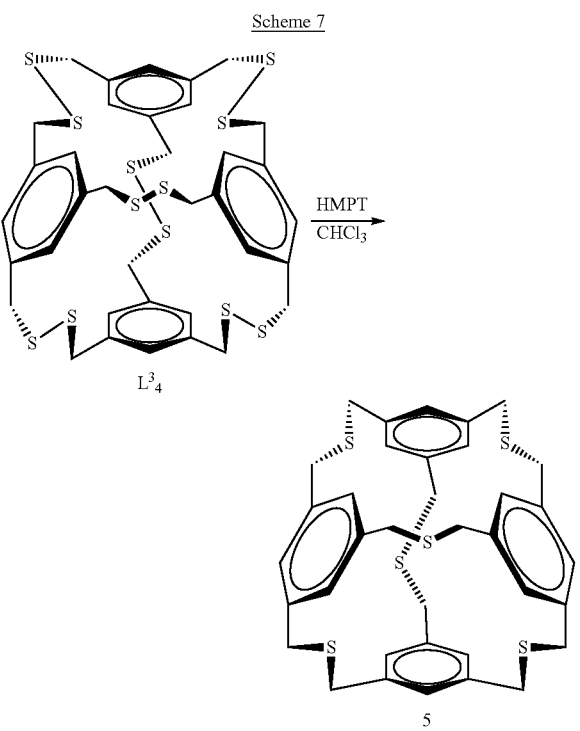

$L^3_4$

5

Analysis of the Molecular structures

As seen in FIG. 1, the previously unknown trithioether 1 was not coplanar such that the benzene rings are in a "face conformation" in the solid state, as commonly seen in paracyclophanes, in which the arenes are perpendicular to the molecular plane and methylene protons are in the equatorial position. In thioether 1 the C—S—C angles were 90.69°, 98.58°, and 103.55° and the average ring distance between the two closest benzene rings was 3.968 Å, too large a distance for π-π interactions.

The $^1$H-NMR spectra of the disulfide [$L^3_4$] and thioether 5 were consistent with a molecule in solution with tetrahedral symmetry. However, the crystal structure [$L^3_4$] folded in on itself to avoid the entropic cost of a large void in the solid state (FIG. 5). [$L^3_4$] crystallized in the P2$_1$/c space group and displayed small dihedral bond angle strain with an average C—S—S—C angle of 104.18°.

5 crystallized in the P2$_1$/n space group and cocrystallized with chloroform molecules of solvation. (FIG. 8) Similarly to [$L^3_4$], the thiatetrahedrophane collapsed in on itself thus avoiding unfavorable void space. The C—S—C angles of the thioether bonds within the cyclophane slightly deviated from ideal (average angle 101.125°).

The synthesis of tri-fold disulfide cyclophanes via self-assembly is an opposing representation to the reactivity described for thiol-disulfide interchange shown by Whitesides, who proposed three-fold cyclic bis(disulfides) are not thermodynamically stable, but kinetic species with respect to polymer when oxidized with iodine. Whitesides' computational studies predicted [$L^3_2$] to be seriously strained and thus not to form. Whitesides later published a high dilution, Wurtz coupling preparation of [$L^3_2$] at 68% yield characterized, exclusively by $^1$H-NMR, and noted its insolubility in most organic solvents (only sparingly soluble in benzene or toluene). However, surprisingly, the highly crystalline [$L^3_2$] synthesized by the disclosed method, was soluble in polar organic solvents like methylene chloride, as well as benzene. Without being bound to a particular theory, it has been suggested that Whitesides' Wurtz coupling to the dimer may have included insoluble polymers that affected Whitesides' ability to collect mass spectrometry and grow single crystals.

CONCLUSION

Disclosed herein is a selective, high yielding alternative to traditional cyclophane synthesis by the use of a metal additive, such as a pnictogen additive, to direct the self-assembly of discrete disulfide cyclophanes. Using a supramolecular approach eliminated the need for caustic, temperature-sensitive methods by limiting the rapid formation of unfavorable insoluble oligomers. This dynamic covalent methodology allowed the synthesis of formerly inaccessible, higher ordered species such as trimers, tetramers, pentamers, hexamers and tetrahedra to be performed cleanly in high yield. These disulfide complexes served as excellent precursors to their thioether and hydrocarbon analogues, by treating them with sulfur extrusion agents. This supramolecular approach served as a powerful strategy because new cyclophanes can be made in those cases where strain and complex design were previously difficult to conceive or did not possess enough selectivity to be formed via classical coupling techniques. This strategy is of particular interest to the future synthetic design of many heterocycles like calixarenes, cryptands and spherands, as well as toward the myriad of applications for which cyclophanes are utilized such as polymer-based materials, catalysis such as asymmetric catalysis, insulators, protecting barriers in chemical deposition processes and host-guest chemistry.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound, having a formula II

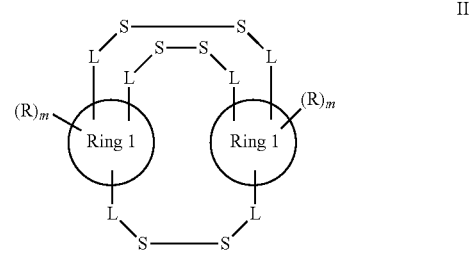

wherein:
   ring 1 is aryl or heteroaryl;
   each R independently is carboxyl ester, aminocarbonyl, alkyl, alkoxy, NO$_2$, sulfonyl, protected amine, aryl, heteroaryl, or halogen;
   m independently is from 0 to 3;
   each L independently is alkyl, aralkyl, or heteroaralkyl comprising one or more heteroatoms selected from N, O or S; and
   wherein if ring 1 is phenyl, and each L is CH$_2$, then m is not 0.

2. The compound of claim 1, wherein the compound has a formula

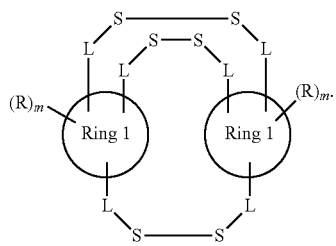

3. The compound of claim 1, wherein m is greater than 0.
4. The compound of claim 1, wherein each R independently is heteroaliphatic.
5. The compound of claim 4, wherein each R is methoxy.
6. The compound of claim 1, wherein each L independently is aliphatic or aralkyl.
7. The compound of claim 6, wherein at least one L is CH$_2$.
8. The compound of claim 6, wherein at least one L is benzyl.
9. The compound of claim 1, wherein ring 1 is phenyl or triazinyl.
10. The compound of claim 1, wherein the

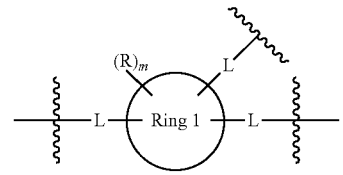

moiety is selected from

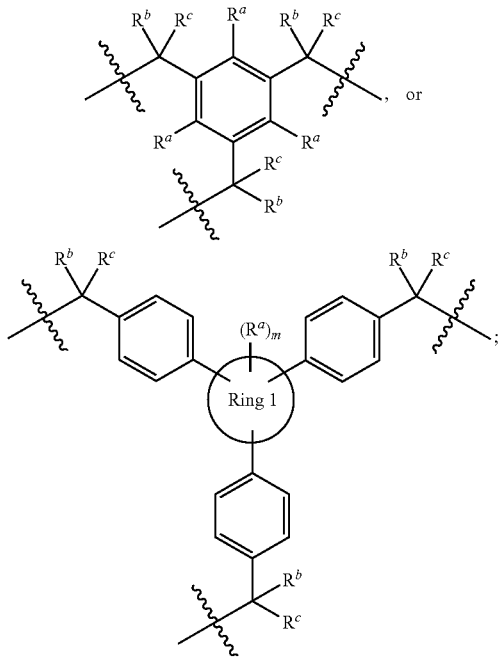

each R$^a$ independently is hydrogen, carboxyl ester, aminocarbonyl, alkyl, alkoxy, NO$_2$, sulfonyl, protected amine, aryl, heteroaryl, or halogen;
each R$^b$ independently is hydrogen, or alkyl; and
each R$^c$ independently is hydrogen, hydrogen, or alkyl.

11. The compound of claim 10, wherein each R$^b$ and R$^c$ is hydrogen.
12. The compound of claim 10, wherein each R$^a$ is hydrogen or alkoxy.
13. The compound of claim 10, wherein each R$^a$, R$^b$ and R$^c$ is hydrogen.
14. The compound of claim 10, wherein ring 1 is phenyl.
15. The compound of claim 10, wherein ring 1 is triazinyl.
16. The compound of claim 10, wherein the

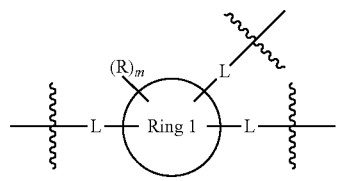

moiety is

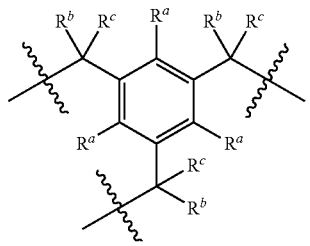

and R$^a$ is methoxy.

17. The compound of claim 10, wherein the

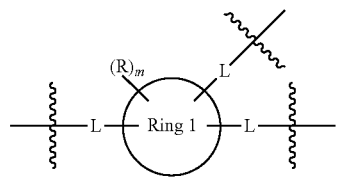

moiety is

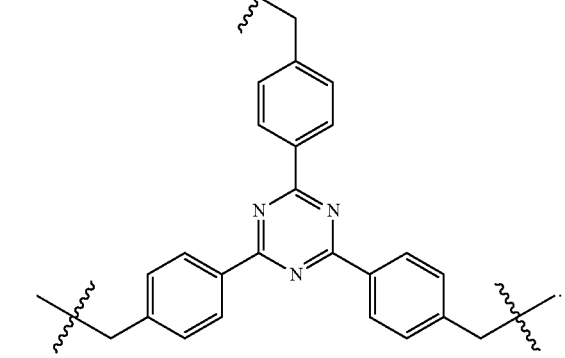

18. The compound of claim 1, wherein the compound is selected from
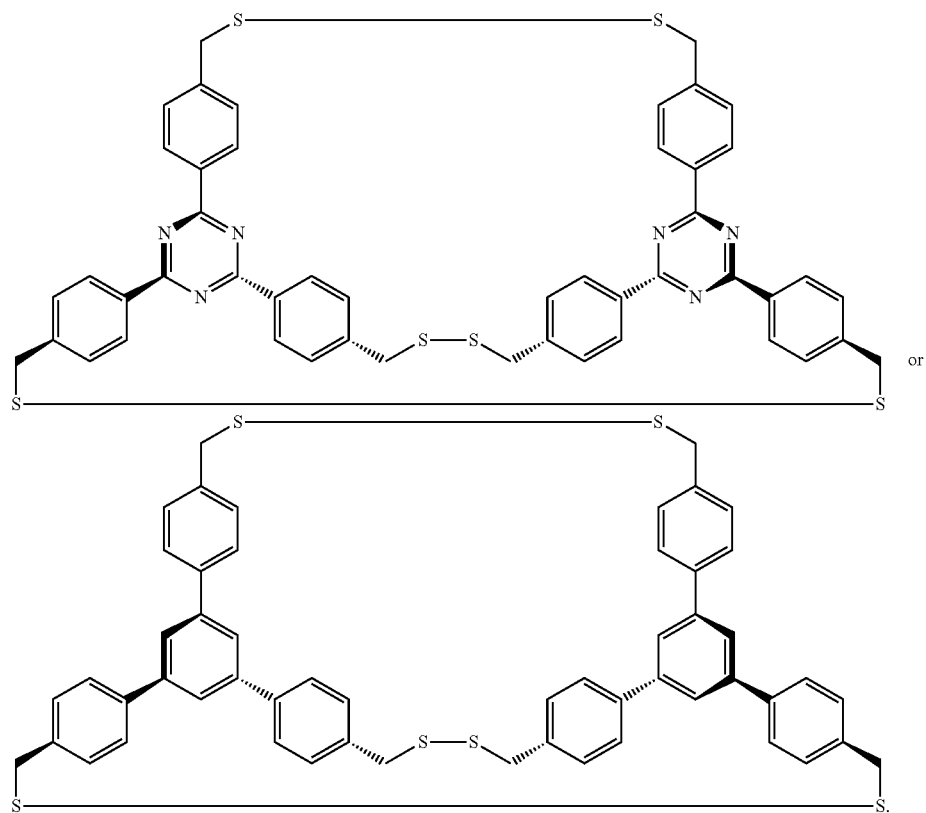
or